US010266863B2

(12) United States Patent
Koetsier et al.

(10) Patent No.: US 10,266,863 B2
(45) Date of Patent: Apr. 23, 2019

(54) ENZYMATIC ACTIVITY OF LYTIC POLYSACCHARIDE MONOOXYGENASE

(71) Applicant: Genencor International B.V., Leiden (NL)

(72) Inventors: Martijn Johannes Koetsier, Wageningen (NL); Jacob Visser, Wageningen (NL); Sandra Wilhelmina Agnes Hinz, Wageningen (NL); Mirjam Anna Kabel, Wageningen (NL); Matthias Frommhagen, Rhenen (NL); Harm Gruppen, Wageningen (NL)

(73) Assignee: Genencor International B.V., Leiden (NL)

( * ) Notice: Subject to any disclaimer, the term of this patent is extended or adjusted under 35 U.S.C. 154(b) by 0 days.

(21) Appl. No.: 15/556,844

(22) PCT Filed: Mar. 11, 2016

(86) PCT No.: PCT/EP2016/055354
§ 371 (c)(1),
(2) Date: Sep. 8, 2017

(87) PCT Pub. No.: WO2016/142536
PCT Pub. Date: Sep. 15, 2016

(65) Prior Publication Data
US 2018/0051305 A1 Feb. 22, 2018

(30) Foreign Application Priority Data

Mar. 11, 2015 (EP) .................................. 15158572

(51) Int. Cl.
*C12P 19/00* (2006.01)
*C12P 19/02* (2006.01)
*C12P 19/12* (2006.01)
*A21D 8/04* (2006.01)
*C12P 19/04* (2006.01)
*A21D 10/00* (2006.01)
*C12N 9/02* (2006.01)

(52) U.S. Cl.
CPC .............. *C12P 19/02* (2013.01); *A21D 8/042* (2013.01); *A21D 10/005* (2013.01); *A21D 10/007* (2013.01); *C12N 9/0083* (2013.01); *C12P 19/00* (2013.01); *C12P 19/04* (2013.01); *C12P 19/12* (2013.01); *C12Y 114/99* (2013.01)

(58) Field of Classification Search
None
See application file for complete search history.

(56) References Cited

U.S. PATENT DOCUMENTS 6,015,707 A  1/2000 Emalfarb et al.
6,573,086 B1  6/2003 Emalfarb et al.

FOREIGN PATENT DOCUMENTS

WO      2009033071 A2    3/2009
WO      WO2012/068236    *  5/2012

OTHER PUBLICATIONS

GenBank: Accession No. AAA34212 (Year: 1993).*
International Search Report, PCT Application No. PCT/EP2016/055354, dated Jul. 25, 2016.
Written Opinion, PCT Application No. PCT/EP2016/055354, dated Sep. 15, 2016.
Agger et al., Discovery of LPMO Activity on Hemicelluloses Shows the Importance of Oxidative Processes in Plant Cell Wall Degradation, PNAS, vol. 111, No. 17 (2014), pp. 6287-6292.
Beeson et al., Cellulose Degradation by Polysaccharide Monooxygenases, Annu. Rev. Biochem., vol. 84 (2015), pp. 923-946.
Bey et al., Cello-Oligosaccharide Oxidation Reveals Differences Between Two Lytic Polysaccharide Monooxygenases (Family GH61) From Podospora Anserina, Applied and Environmental Microbiology, vol. 79, No. 2 (2013), pp. 488-496.
Busk et al., Classification of Fungal and Bacterial Lytic Polysaccharide Monooxygenases, BMC Genomics, vol. 16 (2015), pp. 1-13.
Frommhagen et al., Discovery of the Combined Oxidative Cleavage of Plant Xylan and Cellulose by a New Fungal Polysaccharide Monooxygenase, Biotechnol. Biofuels, 8:101, pp. 1-12, published online Jul. 17, 2015.
Hemsworth et al., Recent Insights Into Copper-Containing Lytic Polysaccharide Mono Oxygenases, Current Opinion in Structural Biology, vol. 23 (2013), pp. 660-668.
Hinz et al., Hemicellulase Production in Chrysosporium Lucknowense C1, Journal of Cereal Science, vol. 50 (2009), pp. 318-323.
Levasseur et al., Expansion of the Enzymatic Repertoire of the Cazy Database to Integrate Auxiliary Redox Enzymes, Biotechnology for Biofuels, vol. 6, No. 41 (2013), pp. 1-14.
Morgenstern et al., Fungal Cellulose Degradation by Oxidative Enzymes: From Dysfunctional GH61 Family to Powerful Lytic Polysaccharide Monooxygenase Family, Briefings in Functional Genomics, vol. 13, No. 6 (2014), pp. 471-481.

(Continued)

Primary Examiner — Rebecca E Prouty

(57) ABSTRACT

The present invention is in the area of enzymes for (hemi-)cellulose degradation and/or modification, more in particular the degradation and/or modification of xylan. The invention is based on a newly discovered enzymatic activity of a class of lytic polysaccharide monooxygenases (LPMOs), i.e. oxidative cleavage of xylan in addition to oxidative cleavage of cellulose. The present invention therefore relates to a method for degrading and/or modifying xylan in a xylan-comprising substrate, a method for preparing a product from a xylan-comprising substrate, a kit of parts, a liquid, paste or solid formulation, and a xylan-comprising composition, comprising said LPMO. The invention further relates to a use of said LPMO, said kit of parts, said formulation and/or said composition, in a method of the invention.

13 Claims, 13 Drawing Sheets

Specification includes a Sequence Listing.

(56) References Cited

OTHER PUBLICATIONS

Van Gool et al., Screening for Distinct Xylan Degrading Enzymes in Complex Shake Flask Fermentation Supernatants, Bioresource Technology, vol. 102 (2011), pp. 6039-6047.
Martine Van Gool, Targeted Discovery and Functional Characterisation of Complex-Xylan Degrading Enzymes, PHD Thesis, Wageningen University, Wageningen, NL (2012), pp. 1-224.

\* cited by examiner

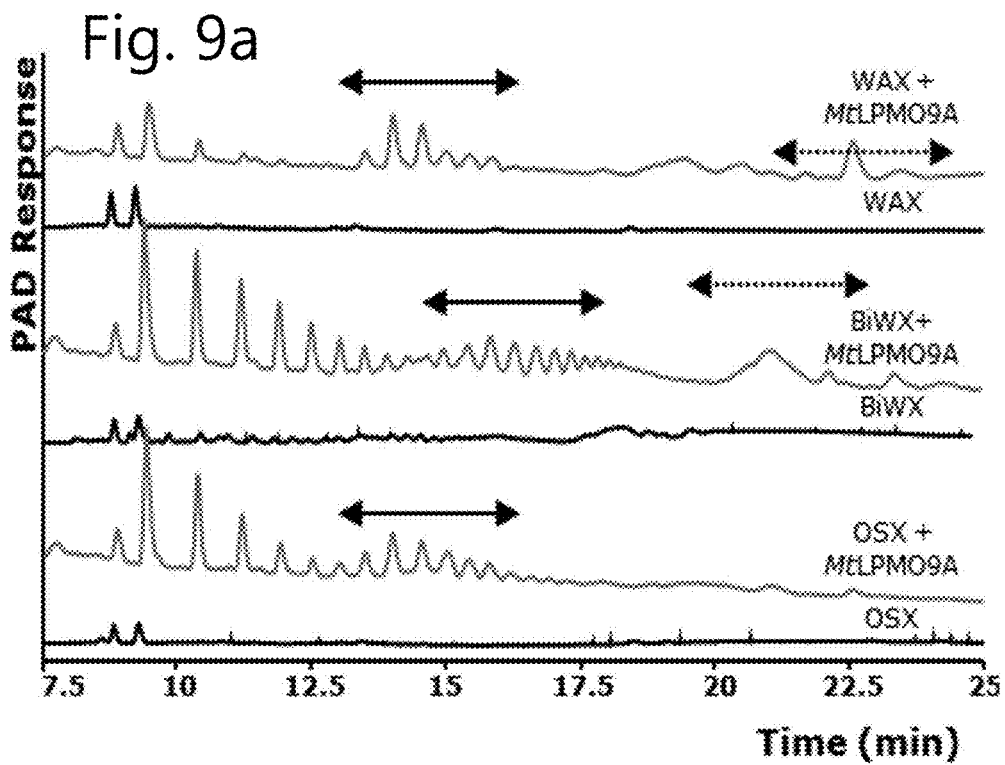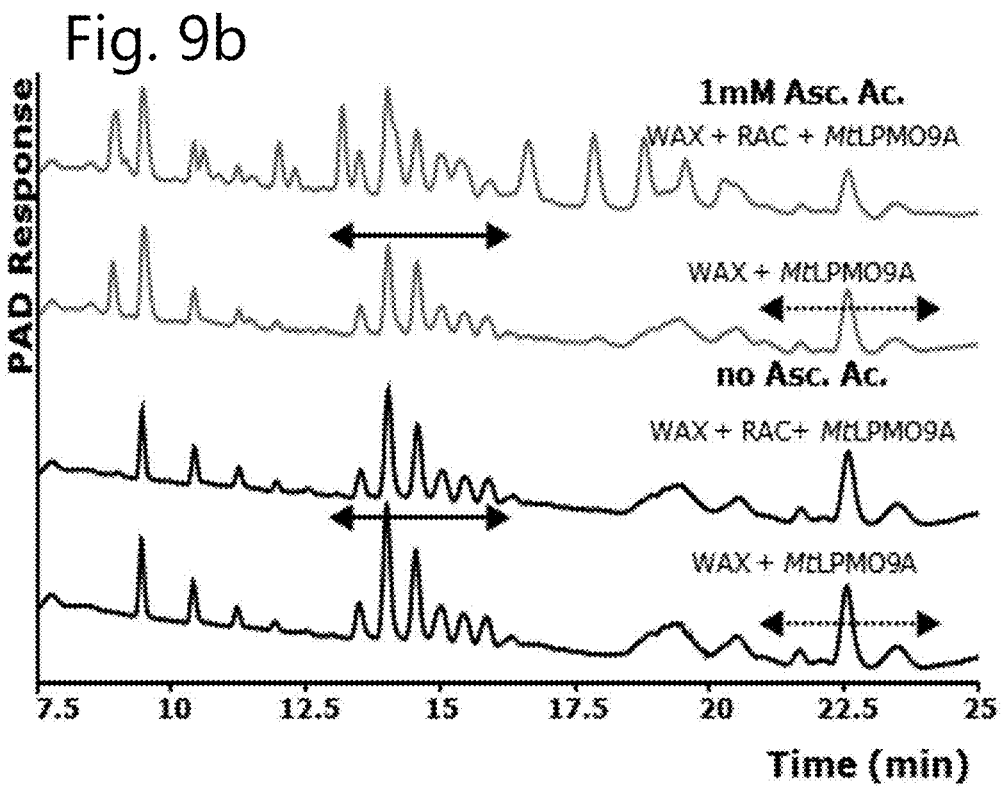

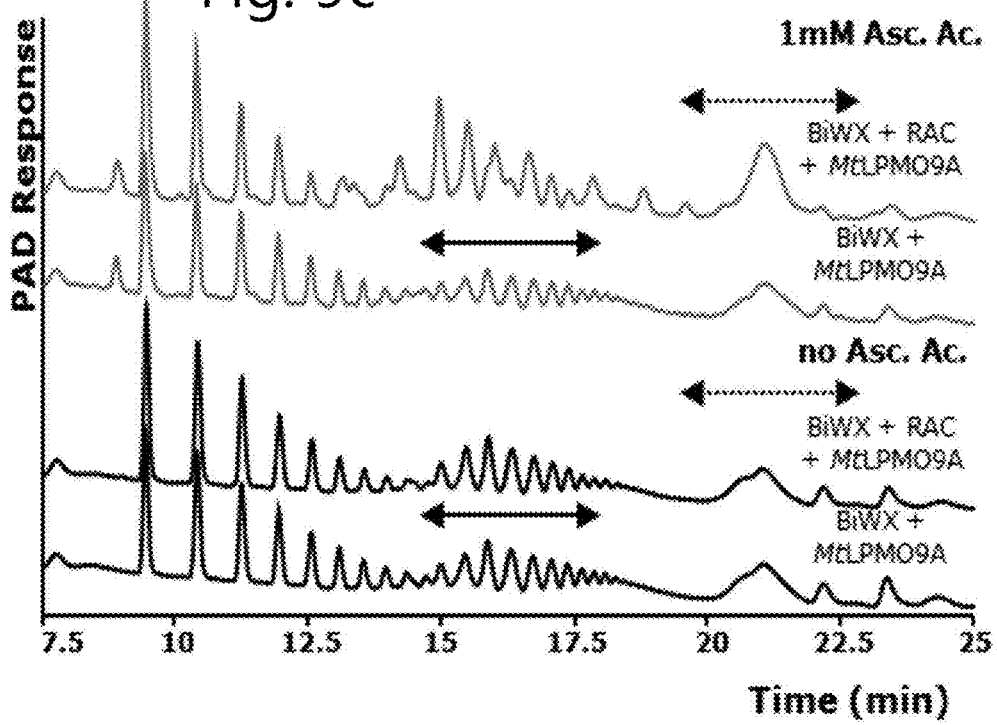
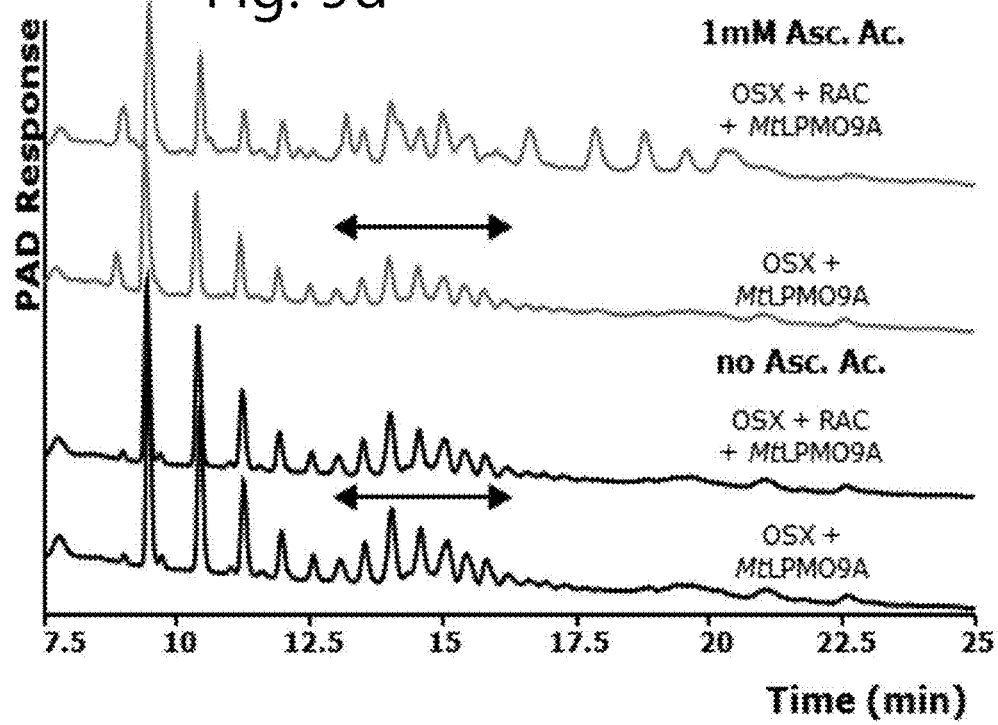

SEQUENCE LISTING

<160> NUMBER OF SEQ ID NOS: 32

<210> SEQ ID NO 1
<211> LENGTH: 208
<212> TYPE: PRT

<213> ORGANISM: Myceliophthora thermophila

<400> SEQUENCE: 1

His Tyr Thr Leu Pro Arg Val Gly Thr Gly Ser Asp Trp Gln His Val
1               5                   10                  15

Arg Arg Ala Asp Asn Trp Gln Asn Asn Gly Phe Val Gly Asp Val Asn
            20                  25                  30

Ser Glu Gln Ile Arg Cys Phe Gln Ala Thr Pro Ala Gly Ala Gln Asp
        35                  40                  45

Val Tyr Thr Val Gln Ala Gly Ser Thr Val Thr Tyr His Ala Asn Pro
    50                  55                  60

Ser Ile Tyr His Pro Gly Pro Met Gln Phe Tyr Leu Ala Arg Val Pro
65                  70                  75                  80

Asp Gly Gln Asp Val Lys Ser Trp Thr Gly Glu Gly Ala Val Trp Phe
                85                  90                  95

Lys Val Tyr Glu Glu Gln Pro Gln Phe Gly Ala Gln Leu Thr Trp Pro
            100                 105                 110

Ser Asn Gly Lys Ser Ser Phe Glu Val Pro Ile Pro Ser Cys Ile Arg
        115                 120                 125

Ala Gly Asn Tyr Leu Leu Arg Ala Glu His Ile Ala Leu His Val Ala
    130                 135                 140

Gln Ser Gln Gly Gly Ala Gln Phe Tyr Ile Ser Cys Ala Gln Leu Gln
145                 150                 155                 160

Val Thr Gly Gly Gly Ser Thr Glu Pro Ser Gln Lys Val Ser Phe Pro
                165                 170                 175

Gly Ala Tyr Lys Ser Thr Asp Pro Gly Ile Leu Ile Asn Ile Asn Tyr
            180                 185                 190

Pro Val Pro Thr Ser Tyr Gln Asn Pro Gly Pro Ala Val Phe Arg Cys
        195                 200                 205

<210> SEQ ID NO 2
<211> LENGTH: 225
<212> TYPE: PRT
<213> ORGANISM: Myceliophthora thermophila

<400> SEQUENCE: 2

Met Leu Thr Thr Thr Phe Ala Leu Leu Thr Ala Ala Leu Gly Val Ser
1               5                   10                  15

Ala His Tyr Thr Leu Pro Arg Val Gly Thr Gly Ser Asp Trp Gln His
            20                  25                  30

Val Arg Arg Ala Asp Asn Trp Gln Asn Asn Gly Phe Val Gly Asp Val
        35                  40                  45

Asn Ser Glu Gln Ile Arg Cys Phe Gln Ala Thr Pro Ala Gly Ala Gln
    50                  55                  60

Asp Val Tyr Thr Val Gln Ala Gly Ser Thr Val Thr Tyr His Ala Asn
65                  70                  75                  80

Pro Ser Ile Tyr His Pro Gly Pro Met Gln Phe Tyr Leu Ala Arg Val
                85                  90                  95

Pro Asp Gly Gln Asp Val Lys Ser Trp Thr Gly Glu Gly Ala Val Trp
            100                 105                 110

Phe Lys Val Tyr Glu Glu Gln Pro Gln Phe Gly Ala Gln Leu Thr Trp
        115                 120                 125

Pro Ser Asn Gly Lys Ser Ser Phe Glu Val Pro Ile Pro Ser Cys Ile
    130                 135                 140

Arg Ala Gly Asn Tyr Leu Leu Arg Ala Glu His Ile Ala Leu His Val

-continued

```
            145                 150                 155                 160
Ala Gln Ser Gln Gly Gly Ala Gln Phe Tyr Ile Ser Cys Ala Gln Leu
                    165                 170                 175

Gln Val Thr Gly Gly Gly Ser Thr Glu Pro Ser Gln Lys Val Ser Phe
                180                 185                 190

Pro Gly Ala Tyr Lys Ser Thr Asp Pro Gly Ile Leu Ile Asn Ile Asn
                195                 200                 205

Tyr Pro Val Pro Thr Ser Tyr Gln Asn Pro Gly Pro Ala Val Phe Arg
210                 215                 220

Cys
225

<210> SEQ ID NO 3
<211> LENGTH: 459
<212> TYPE: PRT
<213> ORGANISM: Thielavia terrestris

<400> SEQUENCE: 3

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
                20                  25                  30

His Pro Lys Leu Thr Thr Tyr Lys Cys Thr Lys Ser Gly Gly Cys Val
            35                  40                  45

Ala Gln Asp Thr Ser Val Val Leu Asp Trp Asn Tyr Arg Trp Met His
        50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
                100                 105                 110

Met Asn Gln Tyr Met Pro Ser Ser Gly Gly Tyr Ile Ser Val Ser
            115                 120                 125

Pro Arg Leu Tyr Leu Leu Asp Ser Asp Gly Glu Tyr Val Met Leu Lys
        130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
                180                 185                 190

Cys Asp Ala Gln Cys Pro Val Gln Thr Trp Arg Asn Gly Thr Leu Asn
            195                 200                 205

Thr Ser His Gln Gly Phe Cys Cys Asn Glu Ile Asp Ile Leu Glu Gly
        210                 215                 220

Asn Ser Arg Ala Asn Ala Leu Thr Pro His Ser Cys Thr Gly Thr Ala
225                 230                 235                 240

Cys Asp Ser Ala Gly Cys Ser Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Arg Asn Phe
        275                 280                 285
```

```
Val Gly Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Arg Asn Asp Asn Ser Gln Tyr Met Asn Trp Leu
                340                 345                 350

Asp Ser Gly Asn Ala Gly Arg Cys Ser Ser Thr Glu Gly Asn Pro Ser
                355                 360                 365

Asn Ile Leu Pro Asn Asn Pro Asn Thr His Phe Val Phe Ser Asn Ile
    370                 375                 380

Cys Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
                420                 425                 430

Ala Ile Gly Cys Ser Gly Cys Lys Thr Cys Thr Ser Gly Thr Thr Cys
                435                 440                 445

Gln Tyr Ser Asn Asp Tyr Tyr Ser Gln Cys Leu
    450                 455

<210> SEQ ID NO 4
<211> LENGTH: 828
<212> TYPE: PRT
<213> ORGANISM: Myceliophthora thermophila

<400> SEQUENCE: 4

Met Arg Thr Ser Ser Arg Leu Ile Gly Ala Leu Ala Ala Ala Leu Leu
1               5                   10                  15

Pro Ser Ala Leu Ala Gln Asn Asn Ala Pro Val Thr Phe Thr Asp Pro
                20                  25                  30

Asp Ser Gly Ile Thr Phe Asn Thr Trp Gly Leu Ala Glu Asp Ser Pro
                35                  40                  45

Gln Thr Lys Gly Gly Phe Thr Phe Gly Val Ala Leu Pro Ser Asp Ala
    50                  55                  60

Leu Thr Thr Asp Ala Lys Glu Phe Ile Gly Tyr Leu Lys Cys Ala Arg
65                  70                  75                  80

Asn Asp Glu Ser Gly Trp Cys Gly Val Ser Leu Gly Gly Pro Met Thr
                85                  90                  95

Asn Ser Leu Leu Ile Ala Ala Trp Pro His Glu Asp Thr Val Tyr Thr
                100                 105                 110

Ser Leu Arg Phe Ala Thr Gly Tyr Ala Met Pro Asp Val Tyr Gln Gly
                115                 120                 125

Asp Ala Glu Ile Thr Gln Val Ser Ser Val Asn Ser Thr His Phe
    130                 135                 140

Ser Leu Ile Phe Arg Cys Glu Asn Cys Leu Gln Trp Ser Gln Ser Gly
145                 150                 155                 160

Ala Thr Gly Gly Ala Ser Thr Ser Asn Gly Val Leu Val Leu Gly Trp
                165                 170                 175

Val Gln Ala Phe Ala Asp Pro Gly Asn Pro Thr Cys Pro Asp Gln Ile
                180                 185                 190

Thr Leu Glu Gln His Asp Asn Gly Met Gly Ile Trp Gly Ala Gln Leu
                195                 200                 205
```

```
Asn Ser Asp Ala Ala Ser Pro Ser Tyr Thr Glu Trp Ala Ala Gln Ala
    210                 215                 220

Thr Lys Thr Val Thr Gly Asp Cys Gly Gly Pro Thr Glu Thr Ser Val
225                 230                 235                 240

Val Gly Val Pro Val Pro Thr Gly Val Ser Phe Asp Tyr Ile Val Val
                    245                 250                 255

Gly Gly Gly Ala Gly Gly Ile Pro Ala Ala Asp Lys Leu Ser Glu Ala
                260                 265                 270

Gly Lys Ser Val Leu Leu Ile Glu Lys Gly Phe Ala Ser Thr Ala Asn
            275                 280                 285

Thr Gly Gly Thr Leu Gly Pro Glu Trp Leu Gly His Asp Leu Thr
    290                 295                 300

Arg Phe Asp Val Pro Gly Leu Cys Asn Gln Ile Trp Val Asp Ser Lys
305                 310                 315                 320

Gly Ile Ala Cys Glu Asp Thr Asp Gln Met Ala Gly Cys Val Leu Gly
                325                 330                 335

Gly Gly Thr Ala Val Asn Ala Gly Leu Trp Phe Lys Pro Tyr Ser Leu
                340                 345                 350

Asp Trp Asp Tyr Leu Phe Pro Ser Gly Trp Lys Tyr Lys Asp Val Gln
            355                 360                 365

Pro Ala Ile Asn Arg Ala Leu Ser Arg Ile Pro Gly Thr Asp Ala Pro
        370                 375                 380

Ser Thr Asp Gly Lys Arg Tyr Tyr Gln Gln Gly Phe Asp Val Leu Ser
385                 390                 395                 400

Lys Gly Leu Ala Gly Gly Gly Trp Thr Ser Val Thr Ala Asn Asn Ala
                405                 410                 415

Pro Asp Lys Lys Asn Arg Thr Phe Ser His Ala Pro Phe Met Phe Ala
            420                 425                 430

Gly Gly Glu Arg Asn Gly Pro Leu Gly Thr Tyr Phe Gln Thr Ala Lys
        435                 440                 445

Lys Arg Ser Asn Phe Lys Leu Trp Leu Asn Thr Ser Val Lys Arg Val
    450                 455                 460

Ile Arg Gln Gly Gly His Ile Thr Gly Val Glu Val Glu Pro Phe Arg
465                 470                 475                 480

Asp Gly Gly Tyr Gln Gly Ile Val Pro Val Thr Lys Val Thr Gly Arg
                485                 490                 495

Val Ile Leu Ser Ala Gly Thr Phe Gly Ser Ala Lys Ile Leu Leu Arg
                500                 505                 510

Ser Gly Ile Gly Pro Asn Asp Gln Leu Gln Val Val Ala Ala Ser Glu
            515                 520                 525

Lys Asp Gly Pro Thr Met Ile Ser Asn Ser Ser Trp Ile Asn Leu Pro
    530                 535                 540

Val Gly Tyr Asn Leu Asp Asp His Leu Asn Thr Asp Thr Val Ile Ser
545                 550                 555                 560

His Pro Asp Val Val Phe Tyr Asp Phe Tyr Glu Ala Trp Asp Asn Pro
                565                 570                 575

Ile Gln Ser Asp Lys Asp Ser Tyr Leu Asn Ser Arg Thr Gly Ile Leu
            580                 585                 590

Ala Gln Ala Ala Pro Asn Ile Gly Pro Met Phe Trp Glu Glu Ile Lys
        595                 600                 605

Gly Ala Asp Gly Ile Val Arg Gln Leu Gln Trp Thr Ala Arg Val Glu
    610                 615                 620
```

```
Gly Ser Leu Gly Ala Pro Asn Gly Lys Thr Met Thr Met Ser Gln Tyr
625                 630                 635                 640

Leu Gly Arg Gly Ala Thr Ser Arg Gly Arg Met Thr Ile Thr Pro Ser
            645                 650                 655

Leu Thr Thr Val Val Ser Asp Val Pro Tyr Leu Lys Asp Pro Asn Asp
        660                 665                 670

Lys Glu Ala Val Ile Gln Gly Ile Ile Asn Leu Gln Asn Ala Leu Lys
    675                 680                 685

Asn Val Ala Asn Leu Thr Trp Leu Phe Pro Asn Ser Thr Ile Thr Pro
690                 695                 700

Arg Gln Tyr Val Asp Ser Met Val Val Ser Pro Ser Asn Arg Arg Ser
705                 710                 715                 720

Asn His Trp Met Gly Thr Asn Lys Ile Gly Thr Asp Asp Gly Arg Lys
            725                 730                 735

Gly Gly Ser Ala Val Val Asp Leu Asn Thr Lys Val Tyr Gly Thr Asp
            740                 745                 750

Asn Leu Phe Val Ile Asp Ala Ser Ile Phe Pro Gly Val Pro Thr Thr
        755                 760                 765

Asn Pro Thr Ser Tyr Ile Val Thr Ala Ser Glu His Ala Ser Ala Arg
770                 775                 780

Ile Leu Ala Leu Pro Asp Leu Thr Pro Val Pro Lys Tyr Gly Gln Cys
785                 790                 795                 800

Gly Gly Arg Glu Trp Ser Gly Ser Phe Val Cys Ala Asp Gly Ser Thr
            805                 810                 815

Cys Gln Met Gln Asn Glu Trp Tyr Ser Gln Cys Leu
            820                 825

<210> SEQ ID NO 5
<211> LENGTH: 787
<212> TYPE: PRT
<213> ORGANISM: Myceliophthora thermophila

<400> SEQUENCE: 5

Met Lys Leu Leu Ser Arg Val Gly Ala Thr Ala Leu Ala Ala Thr Leu
1               5                   10                  15

Ser Leu Gln Gln Cys Ala Ala Gln Met Thr Glu Gly Thr Tyr Thr Asp
                20                  25                  30

Glu Ala Thr Gly Ile Gln Phe Lys Thr Trp Thr Ala Ser Glu Gly Ala
            35                  40                  45

Pro Phe Thr Phe Gly Leu Thr Leu Pro Ala Asp Ala Leu Glu Lys Asp
    50                  55                  60

Ala Thr Glu Tyr Ile Gly Leu Leu Arg Cys Gln Ile Thr Asp Pro Ala
65                  70                  75                  80

Ser Pro Ser Trp Cys Gly Ile Ser His Gly Ser Gly Gln Met Thr
                85                  90                  95

Gln Ala Leu Leu Leu Val Ala Trp Ala Ser Glu Asp Thr Val Tyr Thr
            100                 105                 110

Ser Phe Arg Tyr Ala Thr Gly Tyr Thr Leu Pro Gly Leu Tyr Thr Gly
        115                 120                 125

Asp Ala Lys Leu Thr Gln Ile Ser Ser Ser Val Ser Glu Asp Ser Phe
    130                 135                 140

Glu Val Leu Phe Arg Cys Glu Asn Cys Phe Ser Trp Asp Gln Asp Gly
145                 150                 155                 160

Thr Lys Gly Asn Val Ser Thr Ser Asn Gly Asn Leu Val Leu Gly Arg
                165                 170                 175
```

```
Ala Ala Ala Lys Asp Gly Val Thr Gly Pro Thr Cys Pro Asp Thr Ala
            180                 185                 190

Glu Phe Gly Phe His Asp Asn Gly Phe Gly Gln Trp Gly Ala Val Leu
        195                 200                 205

Glu Gly Ala Thr Ser Asp Ser Tyr Glu Glu Trp Ala Lys Leu Ala Thr
    210                 215                 220

Thr Thr Pro Glu Thr Thr Cys Asp Gly Thr Gly Pro Gly Asp Lys Glu
225                 230                 235                 240

Cys Val Pro Ala Pro Glu Asp Thr Tyr Asp Tyr Ile Val Val Gly Ala
                245                 250                 255

Gly Ala Gly Gly Ile Thr Val Ala Asp Lys Leu Ser Glu Ala Gly His
            260                 265                 270

Lys Val Leu Leu Ile Glu Lys Gly Pro Pro Ser Thr Gly Leu Trp Asn
        275                 280                 285

Gly Thr Met Lys Pro Glu Trp Leu Glu Ser Thr Asp Leu Thr Arg Phe
    290                 295                 300

Asp Val Pro Gly Leu Cys Asn Gln Ile Trp Val Asp Ser Ala Gly Ile
305                 310                 315                 320

Ala Cys Thr Asp Thr Asp Gln Met Ala Gly Cys Val Leu Gly Gly Gly
                325                 330                 335

Thr Ala Val Asn Ala Gly Leu Trp Trp Lys Pro His Pro Ala Asp Trp
            340                 345                 350

Asp Glu Asn Phe Pro Glu Gly Trp Lys Ser Ser Asp Leu Ala Asp Ala
        355                 360                 365

Thr Glu Arg Val Phe Lys Arg Ile Pro Gly Thr Ser His Pro Ser Gln
    370                 375                 380

Asp Gly Lys Leu Tyr Arg Gln Glu Gly Phe Glu Val Ile Ser Lys Gly
385                 390                 395                 400

Leu Ala Asn Ala Gly Trp Lys Glu Ile Ser Ala Asn Glu Ala Pro Ser
                405                 410                 415

Glu Lys Asn His Thr Tyr Ala His Thr Glu Phe Met Phe Ser Gly Gly
            420                 425                 430

Glu Arg Gly Gly Pro Leu Ala Thr Tyr Leu Ala Ser Ala Ala Glu Arg
        435                 440                 445

Ser Asn Phe Asn Leu Trp Leu Asn Thr Ala Val Arg Arg Ala Val Arg
    450                 455                 460

Ser Gly Ser Lys Val Thr Gly Val Glu Leu Glu Cys Leu Thr Asp Gly
465                 470                 475                 480

Gly Phe Ser Gly Thr Val Asn Leu Asn Glu Gly Gly Val Ile Phe
                485                 490                 495

Ser Ala Gly Ala Phe Gly Ser Ala Lys Leu Leu Leu Arg Ser Gly Ile
            500                 505                 510

Gly Pro Glu Asp Gln Leu Glu Ile Val Ala Ser Ser Lys Asp Gly Glu
        515                 520                 525

Thr Phe Thr Pro Lys Asp Glu Trp Ile Asn Leu Pro Val Gly His Asn
    530                 535                 540

Leu Ile Asp His Leu Asn Thr Asp Leu Ile Ile Thr His Pro Asp Val
545                 550                 555                 560

Val Phe Tyr Asp Phe Tyr Ala Ala Trp Asp Glu Pro Ile Thr Glu Asp
                565                 570                 575

Lys Glu Ala Tyr Leu Asn Ser Arg Ser Gly Ile Leu Ala Gln Ala Ala
            580                 585                 590
```

```
Pro Asn Ile Gly Pro Met Met Trp Asp Gln Val Thr Pro Ser Asp Gly
            595                 600                 605

Ile Thr Arg Gln Phe Gln Trp Thr Cys Arg Val Glu Gly Asp Ser Ser
    610                 615                 620

Lys Thr Asn Ser Thr His Ala Met Thr Leu Ser Gln Tyr Leu Gly Arg
625                 630                 635                 640

Gly Val Val Ser Arg Gly Arg Met Gly Ile Thr Ser Gly Leu Ser Thr
                645                 650                 655

Thr Val Ala Glu His Pro Tyr Leu His Asn Asn Gly Asp Leu Glu Ala
            660                 665                 670

Val Ile Gln Gly Ile Gln Asn Val Val Asp Ala Leu Ser Gln Val Ala
        675                 680                 685

Asp Leu Glu Trp Val Leu Pro Pro Asp Gly Thr Val Ala Asp Tyr
    690                 695                 700

Val Asn Ser Leu Ile Val Ser Pro Ala Asn Arg Arg Ala Asn His Trp
705                 710                 715                 720

Met Gly Thr Ala Lys Leu Gly Thr Asp Asp Gly Arg Ser Gly Gly Thr
                725                 730                 735

Ser Val Val Asp Leu Asp Thr Lys Val Tyr Gly Thr Asp Asn Leu Phe
            740                 745                 750

Val Val Asp Ala Ser Val Phe Pro Gly Met Ser Thr Gly Asn Pro Ser
        755                 760                 765

Ala Met Ile Val Ile Val Ala Glu Gln Ala Ala Gln Arg Ile Leu Ala
    770                 775                 780

Leu Arg Ser
785

<210> SEQ ID NO 6
<211> LENGTH: 577
<212> TYPE: PRT
<213> ORGANISM: Myceliophthora thermophila

<400> SEQUENCE: 6

Met Gln Val Ala Ser Lys Leu Val Ala Val Thr Gly Gly Ala Leu Ala
1               5                   10                  15

Leu Trp Leu His Pro Val Ala Ala Gln Glu Gly Cys Thr Asn Ile Ser
            20                  25                  30

Ser Thr Glu Thr Tyr Asp Tyr Ile Val Val Gly Ser Gly Ala Gly Gly
        35                  40                  45

Ile Pro Val Ala Asp Arg Leu Ser Glu Ala Gly His Lys Val Leu Leu
    50                  55                  60

Ile Glu Lys Gly Pro Pro Ser Thr Gly Arg Trp Gly Gly Ile Met Lys
65                  70                  75                  80

Pro Glu Trp Leu Ile Gly Thr Asn Leu Thr Arg Phe Asp Val Pro Gly
                85                  90                  95

Leu Cys Asn Gln Ile Trp Ala Asp Pro Thr Gly Ala Ile Cys Thr Asp
            100                 105                 110

Val Asp Gln Met Ala Gly Cys Met Leu Gly Gly Gly Thr Ala Val Asn
        115                 120                 125

Ala Gly Leu Trp Trp Lys Pro His Pro Ala Asp Trp Asp Val Asn Phe
    130                 135                 140

Pro Glu Gly Trp His Ser Glu Asp Met Ala Glu Ala Thr Glu Arg Val
145                 150                 155                 160

Phe Glu Arg Ile Pro Gly Thr Ile Thr Pro Ser Met Asp Gly Lys Arg
                165                 170                 175
```

```
Tyr Leu Ser Gln Gly Phe Asp Met Leu Gly Ser Leu Glu Ala Ala
            180                 185                 190

Gly Trp Glu Tyr Leu Val Pro Asn Glu His Pro Asp Arg Lys Asn Arg
        195                 200                 205

Thr Tyr Gly His Ser Thr Phe Met Tyr Ser Gly Glu Arg Gly Gly
    210                 215                 220

Pro Leu Ala Thr Tyr Leu Val Ser Ala Val Gln Arg Glu Gly Phe Thr
225                 230                 235                 240

Leu Trp Met Asn Thr Thr Val Thr Arg Ile Ile Arg Glu Gly His
                245                 250                 255

Ala Thr Gly Val Glu Val Gln Cys Ser Asn Ser Glu Ala Gly Gln Ala
                260                 265                 270

Gly Ile Val Pro Leu Thr Pro Lys Thr Gly Arg Val Ile Val Ser Ala
            275                 280                 285

Gly Ala Phe Gly Ser Ala Lys Leu Leu Phe Arg Ser Gly Ile Gly Pro
        290                 295                 300

Lys Asp Gln Leu Asn Ile Val Lys Asn Ser Thr Asp Gly Pro Ser Met
305                 310                 315                 320

Ile Ser Glu Asp Gln Trp Ile Glu Leu Pro Val Gly Tyr Asn Leu Asn
                325                 330                 335

Asp His Val Gly Thr Asp Ile Glu Ile Ala His Pro Asp Val Val Phe
                340                 345                 350

Tyr Asp Tyr Tyr Gly Ala Trp Asp Glu Pro Ile Val Glu Asp Thr Glu
            355                 360                 365

Arg Tyr Val Ala Asn Arg Thr Gly Pro Leu Ala Gln Ala Ala Pro Asn
        370                 375                 380

Ile Gly Pro Ile Phe Trp Glu Thr Ile Lys Gly Ser Asp Gly Val Ser
385                 390                 395                 400

Arg His Leu Gln Trp Gln Ala Arg Val Glu Gly Lys Leu Asn Thr Ser
                405                 410                 415

Met Thr Ile Thr Gln Tyr Leu Gly Thr Gly Ser Arg Ser Arg Gly Arg
                420                 425                 430

Met Thr Ile Thr Arg Arg Leu Asn Thr Val Val Ser Thr Pro Pro Tyr
                435                 440                 445

Leu Arg Asp Glu Tyr Asp Arg Glu Ala Val Ile Gln Gly Ile Ala Asn
450                 455                 460

Leu Arg Glu Ser Leu Lys Gly Val Ala Asn Leu Thr Trp Ile Thr Pro
465                 470                 475                 480

Pro Ser Asn Val Thr Val Glu Asp Phe Val Asp Ser Ile Pro Ala Thr
                485                 490                 495

Pro Ala Arg Arg Cys Ser Asn His Trp Ile Gly Thr Ala Lys Ile Gly
            500                 505                 510

Leu Asp Asp Gly Arg Glu Gly Gly Thr Ser Val Val Asp Leu Asn Thr
        515                 520                 525

Lys Val Tyr Gly Thr Asp Asn Ile Phe Val Val Asp Ala Ser Ile Phe
    530                 535                 540

Pro Gly His Ile Thr Gly Asn Pro Ser Ala Ile Val Ile Ala Ala
545                 550                 555                 560

Glu Tyr Ala Ala Ala Lys Ile Leu Ala Leu Pro Ala Pro Glu Asp Ala
                565                 570                 575

Ala
```

<210> SEQ ID NO 7
<211> LENGTH: 675
<212> TYPE: DNA
<213> ORGANISM: Artificial
<220> FEATURE:
<223> OTHER INFORMATION: cDNA encoding MtLPMO9A

<400> SEQUENCE: 7

| | | |
|---|---|---|
| atgctgacaa caaccttcgc cctcctgacg gccgctctcg gcgtcagcgc ccattatacc | 60 |
| ctccccaggg tcgggaccgg ttccgactgg cagcacgtgc ggcgggctga caactggcaa | 120 |
| aacaacggct cgtcggcga cgtcaactcg gagcagatca ggtgcttcca ggcgaccct | 180 |
| gccggcgccc aagacgtcta cactgttcag gcgggatcga ccgtgaccta ccacgccaac | 240 |
| cccagtatct accaccccgg ccccatgcag ttctacctgg cccgcgttcc ggacggacag | 300 |
| gacgtcaagt cgtggaccgg cgagggtgcc gtgtggttca aggtgtacga ggagcagcct | 360 |
| caatttggcg cccagctgac ctggcctagc aacggcaaga gctcgttcga ggttcctatc | 420 |
| cccagctgca ttcgggcggg caactacctc ctccgcgctg agcacatcgc cctgcacgtt | 480 |
| gcccaaagcc agggcggcgc ccagttctac atctcgtgcg cccagctcca ggtcactggt | 540 |
| ggcggcagca ccgagccttc tcagaaggtt tccttcccgg tgcctacaa gtccaccgac | 600 |
| cccggcattc ttatcaacat caactacccc gtccctacct cgtaccagaa tccgggtccg | 660 |
| gctgtcttcc gttgc | 675 |

<210> SEQ ID NO 8
<211> LENGTH: 963
<212> TYPE: DNA
<213> ORGANISM: Myceliophthora thermophila

<400> SEQUENCE: 8

| | | |
|---|---|---|
| agcggcgttc tgaaaaggag gaacagaact aacgaagacg acccaagcat accaaggtcg | 60 |
| tgttgattag caccccgat tcttccagtt ctttccgcca tctgcaatgc tgacaacaac | 120 |
| cttcgccctc ctgacggccg ctctcggcgt cagcgcccat ataccctcc ccagggtcgg | 180 |
| gaccggttcc gactggcagc acgtgcggcg ggctgacaac tggcaaaaca acggcttcgt | 240 |
| cggcgacgtc aactcggagc agatcaggtg cttccaggcg acccctgccg gcgcccaaga | 300 |
| cgtctacact gttcaggcgg gatcgaccgt gacctaccac gccaacccca gtatctacca | 360 |
| ccccggcccc atgcagttct acctggcccg cgttccggac ggacaggacg tcaagtcgtg | 420 |
| gaccggcgag ggtgccgtgt ggttcaaggt gtacgaggag cagcctcaat ttggcgccca | 480 |
| gctgacctgg cctagcaacg gtgcgttgat cattttcctt cttcttcctt ctttcttccg | 540 |
| ttgcatatgc taactgttct cttgcttgca ggcaagagct cgttcgaggt tcctatcccc | 600 |
| agctgcattc gggcgggcaa ctacctcctc cgcgctgagc atcgccct gcacgttgcc | 660 |
| caaagccagg gcggcgccca gttctacatc tcgtgcgccc agctccaggt cactggtggc | 720 |
| ggcagcaccg agccttctca gaaggtttcc ttcccgggtg cctacaagtc caccgacccc | 780 |
| ggcattctta tcaacatcaa ctaccccgtc cctacctcgt accagaatcc gggtccggct | 840 |
| gtcttccgtt gctaagcggg cacaacaagg gaattggaac ggggcaatgg gggcgggctg | 900 |
| gagccgcctg cgtccttgtt ttcttaccct cgccgttcgt acgaatcagg gccaagcaaa | 960 |
| aca | 963 |

<210> SEQ ID NO 9
<211> LENGTH: 1380
<212> TYPE: DNA

<213> ORGANISM: Artificial
<220> FEATURE:
<223> OTHER INFORMATION: cDNA encoding TvEG I

<400> SEQUENCE: 9

```
atggcgccct cagttacact gccgttgacc acggccatcc tggccattgc ccggctcgtc      60
gccgcccagc aaccgggtac cagcaccccc gaggtccatc ccaagttgac aacctacaag     120
tgtacaaagt ccgggggggtg cgtggcccag gacacctcgg tggtccttga ctggaactac     180
cgctggatgc acgacgcaaa ctacaactcg tgcaccgtca acgcggcgt caacaccacg      240
ctctgccccg acgaggcgac ctgtggcaag aactgcttca tcgagggcgt cgactacgcc     300
gcctcgggcg tcacgacctc gggcagcagc ctcaccatga accagtacat gcccagcagc     360
tctggcggct acatcagcgt ctctcctcgg ctgtatctcc tggactctga cggtgagtac     420
gtgatgctga agctcaacgg ccaggagctg agcttcgacg tcgacctctc tgctctgccg     480
tgtggagaga acggctcgct ctacctgtct cagatggacg agaacggggg cgccaaccag     540
tataacacgg ccgtgccaa ctacgggagc ggctactgcg atgctcagtg ccccgtccag      600
acatggagga acggcaccct caacactagc caccagggct tctgctgcaa cgagattgat     660
atcctggagg gcaactcgag ggcgaatgcc ttgaccccct cactcttgca gggcacggcc     720
tgcgactctg ccggttgcag cttcaacccc tatggcagcg gctacaaaag ctactacggc     780
cccggagata ccgttgacac ctccaagacc ttcaccatca tcacccagtt caacacggac     840
aacggctcgc cctcgcgcaa ctttgtgggc atcacccgca agtaccagca aaacggcgtc     900
gacatcccca gcgcccagcc cggcggtgac accatctcgt cctgcccgtc cgcctcagcc     960
tacggcggcc tcgccaccat gggcaaggcc ctgagcagcg gcatggtgct cgtgttcagc    1020
attcggaacg acaacagcca gtacatgaac tggctcgaca cggcaacgc cggccgctgc    1080
agcagcaccg agggcaaccc atccaacatc ctgcccaaca accccaacac gcacttcgtc    1140
ttctccaaca tctgctgggg agacattggg tctactacga actcgactgc cccccgccc     1200
ccgcctgcgt ctagcacgac gttctcgact acacggagga gctcgacgac ttcgagcagc    1260
ccgagctgca cgcagactca ctgggggcag tgcggtgcca ttgggtgcag cgggtgcaag    1320
acgtgcacgt cgggcactac gtgccagtat agcaacgact actactcgca atgcctttag    1380
```

<210> SEQ ID NO 10
<211> LENGTH: 337
<212> TYPE: PRT
<213> ORGANISM: Myceliophthora thermophila

<400> SEQUENCE: 10

```
Met Lys Phe Leu Asp Val Leu Leu Gly Ala Ala Ala Ser Ser Ala
1               5                   10                  15

Leu Ala Ala Pro Thr Cys Thr Thr Lys Thr Lys Arg Ala Gly Lys Phe
            20                  25                  30

Lys Phe Val Gly Val Asn Gln Ser Cys Ala Glu Phe Gly Gln Asp Thr
        35                  40                  45

Leu Pro Gly Gln Leu Asn Lys His Tyr Thr Trp Pro Ala Lys Ser Ser
    50                  55                  60

Ile Asp Thr Leu Leu Ala Thr Gly Met Asn Thr Ile Arg Ile Pro Phe
65                  70                  75                  80

Met Met Glu Arg Leu Ile Pro Asn Gln Leu Thr Gly Thr Val Asn Glu
                85                  90                  95

Thr Tyr Ser Ala Gly Leu Ile Asp Thr Val Ser Tyr Val Thr Ser Lys
```

```
              100                 105                 110
Gly Ala Tyr Ala Val Ile Asp Pro His Asn Phe Gly Arg Tyr Tyr Thr
            115                 120                 125

Gln Val Ile Thr Asp Val Glu Gly Phe Lys Ala Trp Trp Thr Thr Thr
130                 135                 140

Ala Gly Leu Phe Ala Asp Asn Asp Lys Val Ile Phe Asp Thr Asn Asn
145                 150                 155                 160

Glu Tyr His Asp Met Asp Gln Ser Leu Val Val Asn Leu Asn Gln Ala
                165                 170                 175

Ala Ile Asp Gly Ile Arg Ala Ala Gly Ala Thr Ser Gln Tyr Ile Phe
            180                 185                 190

Ile Glu Gly Asn Ser Trp Thr Gly Ala Trp Thr Trp Val Ser Ser Gly
        195                 200                 205

Asn Gly Glu Ser Leu Leu Asn Leu Ser Asp Pro Glu Gly Asp Asp Lys
    210                 215                 220

Leu Ile Tyr Glu Met His Gln Tyr Leu Asp Glu Asp Gly Ser Gly Thr
225                 230                 235                 240

His Glu Gln Cys Val Ser Gly Thr Ile Gly Arg Glu Arg Leu Gln Ala
                245                 250                 255

Ala Thr Glu Trp Leu Lys Ala Asn Gly Lys Lys Ala Ile Leu Gly Glu
            260                 265                 270

Thr Ala Gly Gly Ala Asn Asp Gln Cys Ile Ser Ala Leu Thr Gly Met
        275                 280                 285

Leu Ser Phe Met Glu Glu Asn Ser Asp Val Trp Gln Gly Trp Leu Trp
    290                 295                 300

Trp Ala Ala Gly Pro Trp Trp Ala Asp Tyr Met Tyr Ser Ile Glu Pro
305                 310                 315                 320

Pro Ser Gly Thr Ala Tyr Thr Lys Val Leu Pro Ser Leu Gln Pro Tyr
                325                 330                 335

Ile
```

<210> SEQ ID NO 11
<211> LENGTH: 1014
<212> TYPE: DNA
<213> ORGANISM: Artificial
<220> FEATURE:
<223> OTHER INFORMATION: cDNA encoding MtEG VIII

<400> SEQUENCE: 11

```
atgaagttcc tcgacgtcct tctcggtgcc gcagctgcca gctcggccct ggcagcgccg      60
acttgcacaa ccaagacaaa gcgcgcgggc aagttcaagt ttgtcggcgt caaccagtcc     120
tgcgccgagt ttggccagga cacgctcccg ggccagctca acaagcacta ccctggccg     180
gccaagtcga gcattgatac actcctcgcc accggaatga acaccattcg catcccgttt     240
atgatggagc gtcttatccc caaccaactg acgggaaccg tcaacgaaac gtactccgcg     300
gggcttatcg ataccgtttc ctacgtcacg agcaagggag cctatgctgt cattgacccc     360
cataacttcg gccggtacta cacgcaagtc atcaccgacg tcgaaggctt caaggcctgg     420
tggacgacca cggccgggct gtttgccgac aacgacaagg tcatcttcga caccaacaac     480
gagtaccacg acatggacca atcgctcgtt gtcaatctga accaggccgc catcgacggc     540
atccgggccg ccggcgccac ctcgcagtac atctttatcg agggcaactc gtggacgggc     600
gcatggacct gggtctcctc gggcaacggc gagtccctgc tgaacctgtc ggacccggag     660
ggcgacgaca agctcatcta cgagatgcac cagtacctgg acgaggacgg gtcgggcacg     720
```

| | |
|---|---:|
| cacgagcagt gcgtctcggg caccatcggc cgggagcgcc tccaggcggc gaccgagtgg | 780 |
| ctcaaggcca acggcaagaa ggccatcctg ggcgagacgg ccggcggcgc caacgaccag | 840 |
| tgcatctcgg ccctgaccgg catgctctcc ttcatggagg agaactcgga cgtctggcag | 900 |
| ggctggctct ggtgggctgc cggtccctgg tgggccgact acatgtactc gattgagccg | 960 |
| ccgagcggta ccgcgtacac caaggttttg cccagcctcc agccttatat ctga | 1014 |

<210> SEQ ID NO 12
<211> LENGTH: 2000
<212> TYPE: DNA
<213> ORGANISM: Myceliophthora thermophila

<400> SEQUENCE: 12

| | |
|---|---:|
| gccccgggc gcgttccgag ttgaatgaat gagcgggtta atatagtaaa gatctgcgct | 60 |
| ataacctggt ctcgagcgcg gagccaacct ttccgagcac gcatcttgat aatgagtaaa | 120 |
| cccccttcaa caaacttgtg aaagagctac ctatagctgg acatataaat ctgcaatggc | 180 |
| catctcagaa agggacccca tgcggaaccg ttggtgcagc aggaagcggt ttactttctg | 240 |
| tcgacaacca actcaaccat gaagttcctc gacgtccttc tcggtgccgc agctgccagc | 300 |
| tcggccctgg cagcgccgac ttgcacaacc aagacaaagc gcgcgggcaa gttcaagttt | 360 |
| gtcggcgtca ccagtcctg cgccgagttt ggccaggaca cgctcccggg ccagctcaac | 420 |
| aagcactaca cctggccggc caagtcgagc attgatgtaa gtgtctttga acttcgagct | 480 |
| accatgacga aaaaggaaca atggaagtaa ccaggctttc gaaaatcaga cactcctcgc | 540 |
| caccggaatg aacaccattc gcatcccgtt tatgatgtag gactgagtgc cctttccgct | 600 |
| tcgctttaca agtaaagagg gcacacattg ctgacaacgg gttgcaggga gcgtcttatc | 660 |
| cccaaccaac tgacgggaac cgtcaacgaa acgtactccg cggggcttat cgatgtatga | 720 |
| aacagacata gagcttctca agaacggggg gccggaattt gctgaccgga atttcagacc | 780 |
| gtttcctacg tcacgagcaa gggagcctat gctgtcattg accccataa cttcggtacg | 840 |
| accagcttac aatgaccatg tcttgggacc gtggcagaca agctaaccaa gacttgctcc | 900 |
| accaaatttc acaggccggt actacacgca agtcatcacc gacgtcgaag gcttcaaggc | 960 |
| ctggtggacg accacggccg ggctgtttgc cgacaacgac aaggtcatct tcgacaccaa | 1020 |
| caacgagtac cacgacatgg accaatcgct cgttgtcaat ctgaaccagg ccgccatcga | 1080 |
| cggcatccgg ccgccggcg ccacctcgca gtacatcttt atcgagggca actcgtggac | 1140 |
| gggcgcatgg acctgggtac gaacacggat ttctgatccg gatatttata ttgattttat | 1200 |
| gattttgttt ttttggaccg gtgtaatagc agctgacaat catgtcattt ccaggtctcc | 1260 |
| tcgggcaacg gcgagtccct gctgaacctg tcggacccgg agggcgacga caagctcatc | 1320 |
| tacgagatgc accagtacct ggacgaggac gggtcgggca cgcacgagca gtgcgtctcg | 1380 |
| ggcaccatcg gccgggagcg cctccaggcg gcgaccgagt ggctcaaggc caacggcaag | 1440 |
| aaggccatcc tgggcgagac ggccggcggc gccaacgacc agtgcatctc ggccctgacc | 1500 |
| ggcatgctct ccttcatgga ggagaactcg gacgtctggc agggctggct ctggtgggct | 1560 |
| gccggtccct ggtgggccga ctacatgtac tcgatgtgag tgttttctta ttttcttct | 1620 |
| ctcatttcat tccttttctga agatcttgtt ttttttccc tccctgtcta acctcgctta | 1680 |
| gtgagccgcc gagcggtacc gcgtacacca aggttttgcc cagcctccag ccttatatct | 1740 |
| gagctcggtc ggttctgcaa acgttgcgga gcggaagaag attccactgt tggggttgat | 1800 | cacaaagata ctgagcctta agtgtacttt acttcatcag ggtagatgaa atcgagcaag    1860 atacatacag ttccctgaga gctatggtcc ttacgtcacg tcactcaact gaggacccaa    1920 attgcccgag tcttaatcca aagagtactc cgtaccgcta ccagggcgat gactcctgta    1980 aattacactg ataatacaaa                                                2000

<210> SEQ ID NO 13
<211> LENGTH: 389
<212> TYPE: PRT
<213> ORGANISM: Myceliophthora thermophila

<400> SEQUENCE: 13

Met Lys Ser Ser Ile Leu Ala Ser Val Phe Ala Thr Gly Ala Val Ala
1               5                   10                  15

Gln Ser Gly Pro Trp Gln Gln Cys Gly Gly Ile Gly Trp Gln Gly Ser
            20                  25                  30

Thr Asp Cys Val Ser Gly Tyr His Cys Val Tyr Gln Asn Asp Trp Tyr
        35                  40                  45

Ser Gln Cys Val Pro Gly Ala Ala Ser Thr Thr Leu Gln Thr Ser Thr
    50                  55                  60

Thr Ser Arg Pro Thr Ala Thr Ser Thr Ala Pro Pro Ser Ser Thr Thr
65                  70                  75                  80

Ser Pro Ser Lys Gly Lys Leu Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
        115                 120                 125

Asn Ile Phe Arg Ile Asp Phe Ser Met Glu Arg Leu Val Pro Asn Gln
    130                 135                 140

Leu Thr Ser Ser Phe Asp Glu Gly Tyr Leu Arg Asn Leu Thr Glu Val
145                 150                 155                 160

Val Asn Phe Val Thr Asn Ala Gly Lys Tyr Ala Val Leu Asp Pro His
                165                 170                 175

Asn Tyr Gly Arg Tyr Tyr Gly Asn Val Ile Thr Asp Thr Asn Ala Phe
            180                 185                 190

Arg Thr Phe Trp Thr Asn Leu Ala Lys Gln Phe Ala Ser Asn Ser Leu
        195                 200                 205

Val Ile Phe Asp Thr Asn Asn Glu Tyr Asn Thr Met Asp Gln Thr Leu
    210                 215                 220

Val Leu Asn Leu Asn Gln Ala Ala Ile Asp Gly Ile Arg Ala Ala Gly
225                 230                 235                 240

Ala Thr Ser Gln Tyr Ile Phe Val Glu Gly Asn Ala Trp Ser Gly Ala
                245                 250                 255

Trp Ser Trp Asn Thr Thr Asn Thr Asn Met Ala Ala Leu Thr Asp Pro
            260                 265                 270

Gln Asn Lys Ile Val Tyr Glu Met His Gln Tyr Leu Asp Ser Asp Ser
        275                 280                 285

Ser Gly Thr His Ala Glu Cys Val Ser Ser Asn Ile Gly Ala Gln Arg
    290                 295                 300

Val Val Gly Ala Thr Gln Trp Leu Arg Ala Asn Gly Lys Leu Gly Val
305                 310                 315                 320

Leu Gly Glu Phe Ala Gly Gly Ala Asn Ala Val Cys Gln Gln Ala Val
                325                 330                 335

```
Thr Gly Leu Leu Asp His Leu Gln Asp Asn Ser Asp Val Trp Leu Gly
                340                 345                 350

Ala Leu Trp Trp Ala Ala Gly Pro Trp Trp Gly Asp Tyr Met Tyr Ser
            355                 360                 365

Phe Glu Pro Pro Ser Gly Thr Gly Tyr Val Asn Tyr Asn Ser Ile Leu
        370                 375                 380

Lys Lys Tyr Leu Pro
385

<210> SEQ ID NO 14
<211> LENGTH: 373
<212> TYPE: PRT
<213> ORGANISM: Myceliophthora thermophila

<400> SEQUENCE: 14

Gln Ser Gly Pro Trp Gln Gln Cys Gly Gly Ile Gly Trp Gln Gly Ser
1               5                   10                  15

Thr Asp Cys Val Ser Gly Tyr His Cys Val Tyr Gln Asn Asp Trp Tyr
                20                  25                  30

Ser Gln Cys Val Pro Gly Ala Ala Ser Thr Thr Leu Gln Thr Ser Thr
            35                  40                  45

Thr Ser Arg Pro Thr Ala Thr Ser Thr Ala Pro Pro Ser Ser Thr Thr
        50                  55                  60

Ser Pro Ser Lys Gly Lys Leu Lys Trp Leu Gly Ser Asn Glu Ser Gly
65                  70                  75                  80

Ala Glu Phe Gly Glu Gly Asn Tyr Pro Gly Leu Trp Gly Lys His Phe
                85                  90                  95

Ile Phe Pro Ser Thr Ser Ala Ile Gln Thr Leu Ile Asn Asp Gly Tyr
                100                 105                 110

Asn Ile Phe Arg Ile Asp Phe Ser Met Glu Arg Leu Val Pro Asn Gln
            115                 120                 125

Leu Thr Ser Ser Phe Asp Glu Gly Tyr Leu Arg Asn Leu Thr Glu Val
        130                 135                 140

Val Asn Phe Val Thr Asn Ala Gly Lys Tyr Ala Val Leu Asp Pro His
145                 150                 155                 160

Asn Tyr Gly Arg Tyr Tyr Gly Asn Val Ile Thr Asp Thr Asn Ala Phe
                165                 170                 175

Arg Thr Phe Trp Thr Asn Leu Ala Lys Gln Phe Ala Ser Asn Ser Leu
            180                 185                 190

Val Ile Phe Asp Thr Asn Asn Glu Tyr Asn Thr Met Asp Gln Thr Leu
        195                 200                 205

Val Leu Asn Leu Asn Gln Ala Ala Ile Asp Gly Ile Arg Ala Ala Gly
    210                 215                 220

Ala Thr Ser Gln Tyr Ile Phe Val Glu Gly Asn Ala Trp Ser Gly Ala
225                 230                 235                 240

Trp Ser Trp Asn Thr Thr Asn Thr Asn Met Ala Ala Leu Thr Asp Pro
                245                 250                 255

Gln Asn Lys Ile Val Tyr Glu Met His Gln Tyr Leu Asp Ser Asp Ser
            260                 265                 270

Ser Gly Thr His Ala Glu Cys Val Ser Ser Asn Ile Gly Ala Gln Arg
        275                 280                 285

Val Val Gly Ala Thr Gln Trp Leu Arg Ala Asn Gly Lys Leu Gly Val
    290                 295                 300

Leu Gly Glu Phe Ala Gly Gly Ala Asn Ala Val Cys Gln Gln Ala Val
305                 310                 315                 320
```

Thr Gly Leu Leu Asp His Leu Gln Asp Asn Ser Asp Val Trp Leu Gly
                325                 330                 335

Ala Leu Trp Trp Ala Ala Gly Pro Trp Trp Gly Asp Tyr Met Tyr Ser
            340                 345                 350

Phe Glu Pro Pro Ser Gly Thr Gly Tyr Val Asn Tyr Asn Ser Ile Leu
        355                 360                 365

Lys Lys Tyr Leu Pro
    370

<210> SEQ ID NO 15
<211> LENGTH: 1170
<212> TYPE: DNA
<213> ORGANISM: Artificial
<220> FEATURE:
<223> OTHER INFORMATION: cDNA encoding MtEG II

<400> SEQUENCE: 15

| | | |
|---|---|---|
| atgaagtcct ccatcctcgc cagcgtcttc gccacgggcg ccgtggctca aagtggtccg | 60 |
| tggcagcaat gtggtggcat cggatggcaa ggatcgaccg actgtgtgtc gggttaccac | 120 |
| tgcgtctacc agaacgattg gtacagccag tgcgtgcctg gcgcggcgtc gacaacgctc | 180 |
| cagacatcta ccacgtccag gcccaccgcc accagcaccg cccctccgtc gtccaccacc | 240 |
| tcgcctagca agggcaagct caagtggctc ggcagcaacg agtcgggcgc cgagttcggg | 300 |
| gagggcaact accccggcct ctggggcaag cacttcatct tcccgtcgac ttcggcgatt | 360 |
| cagacgctca tcaatgatgg atacaacatc ttccggatcg acttctcgat ggagcgtctg | 420 |
| gtgcccaacc agttgacgtc gtccttcgac gagggctacc tccgcaacct gaccgaggtg | 480 |
| gtcaacttcg tgacgaacgc gggcaagtac gccgtcctgg acccgcacaa ctacggccgg | 540 |
| tactacggca acgtcatcac ggacacgaac gcgttccgga ccttctggac caacctggcc | 600 |
| aagcagttcg cctccaactc gctcgtcatc ttcgacacca caacgagta caacacgatg | 660 |
| gaccagaccc tggtgctcaa cctcaaccag gccgccatcg acggcatccg ggccgccggc | 720 |
| gcgacctcgc agtacatctt cgtcgagggc aacgcgtgga cgggggcctg gagctggaac | 780 |
| acgaccaaca ccaacatggc cgccctgacg gacccgcaga acaagatcgt gtacgagatg | 840 |
| caccagtacc tcgactcgga cagctcgggc acccacgccg agtgcgtcag cagcaacatc | 900 |
| ggcgcccagc gcgtcgtcgg agccaccag tggctccgcg ccaacggcaa gctcggcgtc | 960 |
| ctcggcgagt tcgccggcgg cgccaacgcc gtctgccagc aggccgtcac cggcctcctc | 1020 |
| gaccacctcc aggacaacag cgacgtctgg ctgggtgccc tctggtgggc cgccggtccc | 1080 |
| tggtggggcg actacatgta ctcgttcgag cctccttcgg gcaccggcta tgtcaactac | 1140 |
| aactcgatcc taaagaagta cttgccgtaa | 1170 |

<210> SEQ ID NO 16
<211> LENGTH: 1616
<212> TYPE: DNA
<213> ORGANISM: Myceliophthora thermophila

<400> SEQUENCE: 16

| | | |
|---|---|---|
| atgaagtcct ccatcctcgc cagcgtcttc gccacgggcg ccgtggctca aagtggtccg | 60 |
| tggcagcaat gtggtggcat cggatggcaa ggatcgaccg actgtgtgtc gggttaccac | 120 |
| tgcgtctacc agaacgattg gtacagccag tgcgtgcctg gcgcggcgtc gacaacgctc | 180 |
| cagacatcta ccacgtccag gcccaccgcc accagcaccg cccctccgtc gtccaccacc | 240 |

```
tcgcctagca  agggcaagct  caagtggctc  ggcagcaacg  agtcgggcgc  cgagttcggg   300
gagggcaact  accccggcct  ctggggcaag  cacttcatct  tcccgtcgac  ttcggcgatt   360
caggtacggc  caataataat  atattattat  agcaggcagg  agggagcagg  agaagaaggg   420
aggggcaggt  ggccaacaat  cggaagaaga  ccgggaggca  ctgaccgttg  attcctttgt   480
gtaatagacg  ctcatcaatg  atggatacaa  catcttccgg  atcgacttct  cgatggagcg   540
tctggtgccc  aaccagttga  cgtcgtcctt  cgacgagggc  tacctccgca  acctgaccga   600
ggtggtcaac  ttcgtgacga  acgcgggcaa  gtacgccgtc  ctggacccgc  acaactacgg   660
ccggtactac  ggcaacgtca  tcacggacac  gaacgcgttc  cggaccttct  ggaccaacct   720
ggccaagcag  ttcgcctcca  actcgctcgt  catcttcgac  accaacaacg  agtacaacac   780
gatggaccag  accctggtgc  tcaacctcaa  ccaggccgcc  atcgacggca  tccgggccgc   840
cggcgcgacc  tcgcagtaca  tcttcgtcga  gggcaacgcg  tggagcgggg  cctggagctg   900
gaacacgacc  aacaccaaca  tggccgcccct  gacggacccg  cagaacaaga  tcgtgtacga   960
gatgcaccag  tacctcgact  cggacagctc  gggcacccac  gccgagtgcg  tcagcagcaa  1020
catcggcgcc  cagcgcgtcg  tcggagccac  ccagtggctc  cgcgccaacg  gcaagctcgg  1080
cgtcctcggc  gagttcgccg  gcggcgccaa  cgccgtctgc  cagcaggccg  tcaccggcct  1140
cctcgaccac  ctccaggaca  cagcgacgt   ctggctgggt  gccctctggt  gggccgccgg  1200
tccctggtgg  ggcgactaca  tgtactcgtt  cggtaagttt  ctcccttgtt  cttggctttc  1260
cccccagtaa  gggagtcagg  caacatgccc  aagaccggct  cggcttcgct  tcaaggcgtt  1320
cgttgtacac  actgaagagt  tccaacttcc  accctgttc   gtgtcctccg  atcagcttcg  1380
acggggtgaa  gggggaaggg  atttgggagt  gaggtggagg  tcaaaaggag  ggatatcccc  1440
agatctccaa  aaacgccct   gagccaacaa  cagcctctgg  ggtcaaaatg  ggcgccaacc  1500
atacggtcat  tcactcagga  cacctgctaa  cgcgtctctt  ttttttgttt  ccagagcctc  1560
cttcgggcac  cggctatgtc  aactacaact  cgatcctaaa  gaagtacttg  ccgtaa       1616
```

<210> SEQ ID NO 17
<211> LENGTH: 456
<212> TYPE: PRT
<213> ORGANISM: Myceliophthora thermophila

<400> SEQUENCE: 17

```
Met Gly Arg Gly Ala Ala Phe Leu Gly Leu Ala Ser Leu Leu Val Gly
 1               5                  10                  15

Ala Ala Lys Ala Gln Thr Pro Gly Glu Gly Glu Glu Val His Pro Gln
            20                  25                  30

Ile Thr Thr Tyr Arg Cys Thr Lys Ala Asp Gly Cys Glu Glu Lys Thr
        35                  40                  45

Asn Tyr Ile Val Leu Asp Ala Leu Ser His Pro Val His Gln Val Asp
    50                  55                  60

Asn Pro Tyr Asn Cys Gly Asp Trp Gly Gln Lys Pro Asn Glu Thr Ala
65                  70                  75                  80

Cys Pro Asp Leu Glu Ser Cys Ala Arg Asn Cys Ile Met Asp Pro Val
                85                  90                  95

Ser Asp Tyr Gly Arg His Gly Val Ser Thr Asp Gly Thr Ser Leu Arg
           100                 105                 110

Leu Lys Gln Leu Val Gly Gly Asn Val Val Ser Pro Arg Val Tyr Leu
       115                 120                 125

Leu Asp Glu Thr Lys Glu Arg Tyr Glu Met Leu Lys Leu Thr Gly Asn
```

```
                130                 135                 140
Glu Phe Thr Phe Asp Val Asp Ala Thr Lys Leu Pro Cys Gly Met Asn
145                 150                 155                 160

Ser Ala Leu Tyr Leu Ser Glu Met Asp Ala Thr Gly Ala Arg Ser Glu
                165                 170                 175

Leu Asn Pro Gly Gly Ala Thr Phe Gly Thr Gly Tyr Cys Asp Ala Gln
            180                 185                 190

Cys Tyr Val Thr Pro Phe Ile Asn Gly Leu Gly Asn Ile Glu Gly Lys
                195                 200                 205

Gly Ala Cys Cys Asn Glu Met Asp Ile Trp Glu Ala Asn Ala Arg Ala
            210                 215                 220

Gln His Ile Ala Pro His Pro Cys Ser Lys Ala Gly Pro Tyr Leu Cys
225                 230                 235                 240

Glu Gly Ala Glu Cys Glu Phe Asp Gly Val Cys Asp Lys Asn Gly Cys
                245                 250                 255

Ala Trp Asn Pro Tyr Arg Val Asn Val Thr Asp Tyr Tyr Gly Glu Gly
            260                 265                 270

Ala Glu Phe Arg Val Asp Thr Thr Arg Pro Phe Ser Val Val Thr Gln
            275                 280                 285

Phe Arg Ala Gly Gly Asp Ala Gly Gly Lys Leu Glu Ser Ile Tyr
290                 295                 300

Arg Leu Phe Val Gln Asp Gly Arg Val Ile Glu Ser Tyr Val Val Asp
305                 310                 315                 320

Lys Pro Gly Leu Pro Pro Thr Asp Arg Met Thr Asp Glu Phe Cys Ala
                325                 330                 335

Ala Thr Gly Ala Ala Arg Phe Thr Glu Leu Gly Ala Met Glu Ala Met
            340                 345                 350

Gly Asp Ala Leu Thr Arg Gly Met Val Leu Ala Leu Ser Ile Trp Trp
            355                 360                 365

Ser Glu Gly Asp Asn Met Asn Trp Leu Asp Ser Gly Glu Ala Gly Pro
            370                 375                 380

Cys Asp Pro Asp Glu Gly Asn Pro Ser Asn Ile Ile Arg Val Gln Pro
385                 390                 395                 400

Asp Pro Glu Val Val Phe Ser Asn Leu Arg Trp Gly Glu Ile Gly Ser
                405                 410                 415

Thr Tyr Glu Ser Ala Val Asp Gly Pro Val Gly Lys Gly Lys Gly Lys
            420                 425                 430

Gly Lys Gly Lys Ala Pro Ala Gly Asp Gly Asn Gly Lys Glu Lys Ser
            435                 440                 445

Asn Gly Lys Arg Phe Arg Phe
450                 455

<210> SEQ ID NO 18
<211> LENGTH: 436
<212> TYPE: PRT
<213> ORGANISM: Myceliophthora thermophila

<400> SEQUENCE: 18

Gln Thr Pro Gly Glu Gly Glu Val His Pro Gln Ile Thr Thr Tyr
1               5                   10                  15

Arg Cys Thr Lys Ala Asp Gly Cys Glu Glu Lys Thr Asn Tyr Ile Val
                20                  25                  30

Leu Asp Ala Leu Ser His Pro Val His Gln Val Asp Asn Pro Tyr Asn
            35                  40                  45
```

```
Cys Gly Asp Trp Gly Gln Lys Pro Asn Glu Thr Ala Cys Pro Asp Leu
 50                  55                  60
Glu Ser Cys Ala Arg Asn Cys Ile Met Asp Pro Val Ser Asp Tyr Gly
 65                  70                  75                  80
Arg His Gly Val Ser Thr Asp Gly Thr Ser Leu Arg Leu Lys Gln Leu
                 85                  90                  95
Val Gly Gly Asn Val Val Ser Pro Arg Val Tyr Leu Leu Asp Glu Thr
            100                 105                 110
Lys Glu Arg Tyr Glu Met Leu Lys Leu Thr Gly Asn Glu Phe Thr Phe
        115                 120                 125
Asp Val Asp Ala Thr Lys Leu Pro Cys Gly Met Asn Ser Ala Leu Tyr
    130                 135                 140
Leu Ser Glu Met Asp Ala Thr Gly Ala Arg Ser Glu Leu Asn Pro Gly
145                 150                 155                 160
Gly Ala Thr Phe Gly Thr Gly Tyr Cys Asp Ala Gln Cys Tyr Val Thr
                165                 170                 175
Pro Phe Ile Asn Gly Leu Gly Asn Ile Glu Gly Lys Gly Ala Cys Cys
            180                 185                 190
Asn Glu Met Asp Ile Trp Glu Ala Asn Ala Arg Ala Gln His Ile Ala
        195                 200                 205
Pro His Pro Cys Ser Lys Ala Gly Pro Tyr Leu Cys Glu Gly Ala Glu
    210                 215                 220
Cys Glu Phe Asp Gly Val Cys Asp Lys Asn Gly Cys Ala Trp Asn Pro
225                 230                 235                 240
Tyr Arg Val Asn Val Thr Asp Tyr Tyr Gly Glu Gly Ala Glu Phe Arg
                245                 250                 255
Val Asp Thr Thr Arg Pro Phe Ser Val Val Thr Gln Phe Arg Ala Gly
            260                 265                 270
Gly Asp Ala Gly Gly Lys Leu Glu Ser Ile Tyr Arg Leu Phe Val
        275                 280                 285
Gln Asp Gly Arg Val Ile Glu Ser Tyr Val Val Asp Lys Pro Gly Leu
    290                 295                 300
Pro Pro Thr Asp Arg Met Thr Asp Glu Phe Cys Ala Ala Thr Gly Ala
305                 310                 315                 320
Ala Arg Phe Thr Glu Leu Gly Ala Met Glu Ala Met Gly Asp Ala Leu
                325                 330                 335
Thr Arg Gly Met Val Leu Ala Leu Ser Ile Trp Trp Ser Glu Gly Asp
            340                 345                 350
Asn Met Asn Trp Leu Asp Ser Gly Glu Ala Gly Pro Cys Asp Pro Asp
        355                 360                 365
Glu Gly Asn Pro Ser Asn Ile Ile Arg Val Gln Pro Asp Pro Glu Val
    370                 375                 380
Val Phe Ser Asn Leu Arg Trp Gly Glu Ile Gly Ser Thr Tyr Glu Ser
385                 390                 395                 400
Ala Val Asp Gly Pro Val Gly Lys Gly Lys Gly Lys Gly Lys Gly Lys
                405                 410                 415
Ala Pro Ala Gly Asp Gly Asn Gly Lys Glu Lys Ser Asn Gly Lys Arg
            420                 425                 430
Phe Arg Arg Phe
        435

<210> SEQ ID NO 19
<211> LENGTH: 1368
<212> TYPE: DNA
```

<213> ORGANISM: Artificial
<220> FEATURE:
<223> OTHER INFORMATION: cDNA encoding MtEG I

<400> SEQUENCE: 19

```
atgggtcgcg gcgctgcttt cctaggcctc gcctcgctcc tcgtgggcgc ggccaaggcc      60
cagacgcccg gcgagggcga ggaggtgcac ccgcagatca cgacgtaccg ctgcaccaag     120
gcggacgggt gcgaggagaa gaccaactac atcgtgctgg acgccctatc gcacccggtc     180
caccaggtcg acaacccgta caactgcggc gactggggcc agaagcccaa cgagacggcc     240
tgcccggacc tcgagtcgtg cgccaggaac tgcatcatgg acccggtctc ggactacggc     300
cggcacgggg tctcgaccga cggcacctcg ctgcgcctca gcagctagt cggcggcaac     360
gtcgtcagcc cgcgcgtcta cctgctcgac gagaccaagg agcgctacga gatgctcaag     420
ctgaccggca acgagttcac ctttgacgtc gacgccacca gctgccctg cggcatgaac     480
agcgccctct acctctccga gatggacgcc accggcgccc ggagcgagct caacccgggc     540
ggcgccacct ttggcaccgg ctactgcgac gcccagtgct acgtcacccc cttcatcaac     600
ggcctcggca acatcgaggg caagggcgcg tgctgcaacg agatggatat ctgggaggcc     660
aacgcgcggg cgcagcacat cgcgccgcac ccgtgcagca aggcggggcc gtacctgtgc     720
gagggcgccg agtgcgagtt cgacggcgtg tgcgacaaga acggctgcgc ctggaacccg     780
taccgggtca acgtgacgga ctactacggc gagggcgccg agttcagggt ggacacgacc     840
cggcccttct cggtcgtcac gcagttccgc gccggcggcg acgcgggggg cggcaagctc     900
gagagcatct accggctctt cgtccaggac ggcagggtga tcgagtcgta cgtcgtcgac     960
aagcccggcc tgcccccgac ggaccgcatg acggacgagt tctgcgccgc caccggcgcc    1020
gcccgcttca cggagctcgg cgccatggag gccatgggcg acgccctgac gcgcggcatg    1080
gtcctcgccc tcagcatctg gtggagcgag ggcgacaaca tgaactggct cgactcgggc    1140
gaggccggcc cctgcgaccc ggacgagggc aacccgtcca acatcatccg cgtccagccc    1200
gacccggagg tcgtcttcag caacctgcgc tggggcgaga tcggctcaac ctacgagtcc    1260
gccgtcgacg gccccgtcgg caagggcaag gcaagggca agggcaaggc tcccgccggc    1320
gacggcaacg ggaaggagaa gagcaatggc aagcgcttca ggaggttc                 1368
```

<210> SEQ ID NO 20
<211> LENGTH: 2507
<212> TYPE: DNA
<213> ORGANISM: Myceliophthora thermophila

<400> SEQUENCE: 20

```
ctatataaag gtacttacag ataaaatccc caggttgaca gcccttcga gcataagaat      60
ccaggtccta tagtggccgg ctcgaagccc agatttgagc cctattgaga ataactatat    120
ggcactggat gaaggattgg cttgaacatc gctacgatgt ttaatcgctg agtcttacag    180
ggcttcgact ggctgttctg gaggcgtggg aggcagtccc ccccgagttt cttcagtgcc    240
tggcacactc aatgcctcga cggctagcaa aaaccagggg ggagagactg gtattgata     300
cttctgtatt atagaaattt gtattgggtt ggttgtacct agacttcttg ctacttttc    360
tgatttgcgt tagttgtggg gcatgtatcg cactaggatt aataatgctg aagaggtgt     420
agagatgttg cgtcgcatgg ccaccgagat ccggcctggc gtcgtgcctt gcagctcgca    480
cgatgcgcgc gacgatgcgg gacacccctc ccccctcccc cctcccccct acattaggag    540
gggatccggg gccgctgccc gttttccgtc ttggtattcc cggctgacac aacggttctc    600
```

```
cagagtgata accgaggcac accagtagca gtccacgatg gcacggcagg ggatacattc      660
cgcccggaac aacccaagat ctgggaatcc cagtgacgac cccggggtcc tccggggtcc      720
cccgatttcg tctgaaccga cgaactggaa ggaggcgagc cttggaacga tgggggatat      780
gatatatatt aagatgcaac attctctccc tccctcctct ctctctccct ccccccctct      840
ctcctcctct tccctcctc  cccgccgttc tctctccatg agcctcaatt cttgctccga      900
gcgcggtgta tttcccccac gaggaattga caaaagaaaa agaaaaagac aagactctcg      960
agaacgatgg gtcgcggcgc tgctttccta ggcctcgcct cgctcctcgt gggcgcggcc     1020
aaggcccaga cgcccggcga gggcgaggag gtgcacccgc agatcacgac gtaccgctgc     1080
accaaggcgg acgggtgcga ggagaagacc aactacatcg tgctggacgc cctatcgcac     1140
ccggtccacc aggtcgacaa cccgtacaac tgcggcgact ggggccagaa gcccaacgag     1200
acggcctgcc cggacctcga gtcgtgcgcc aggaactgca tcatggaccc ggtctcggac     1260
tacgccggc  acggggtctc gaccgacggc acctcgctgc gcctcaagca gctagtcggc     1320
ggcaacgtcg tcagcccgcg cgtctacctg ctcgacgaga ccaaggagcg ctacgagatg     1380
ctcaagctga ccggcaacga gttcaccttt gacgtcgacg ccaccaagct gccctgcggc     1440
atgaacagcg ccctctacct ctccgagatg gacgccaccg gcgcccggag cgagctcaac     1500
ccgggcggcg ccacctttgg caccggctac tgcgacgccc agtgctacgt cacccccttc     1560
atcaacggcc tcgtacgtat tctcctatta atcttgtttc ttttttcctt ttcttttttt     1620
gatataatag aattaagaag aactcggtgg gctgacatga cacagggcaa catcgagggc     1680
aagggcgcgt gctgcaacga gatggatatc tgggaggcca acgcgcgggc gcagcacatc     1740
gcgccgcacc cgtgcagcaa ggcggggccg tacctgtgcg agggcgccga gtgcgagttc     1800
gacggcgtgt gcgacaagaa cggctgcgcc tggaacccgt accgggtcaa cgtgacggac     1860
tactacggcg agggcgccga gttcagggtg gacacgaccc ggcccttctc ggtcgtcacg     1920
cagttccgcg ccggcggcga cgcggggggc ggcaagctcg agagcatcta ccggctcttc     1980
gtccaggacg gcagggtgat cgagtcgtac gtcgtcgaca gcccggcct  gcccccgacg     2040
gaccgcatga cggacgagtt ctgcgccgcc accggcgccg cccgcttcac ggagctcggc     2100
gccatggagg ccatgggcga cgccctgacg cgcggcatgg tcctcgccct cagcatctgg     2160
tggagcgagg gcgacaacat gaactggctc gactcgggcg aggccggccc ctgcgacccg     2220
gacgagggca accgtccaa  catcatccgc gtccagcccg accggaggt  cgtcttcagc     2280
aacctgcgct ggggcgagat cggctcaacc tacgagtccg ccgtcgacgg gcccgtcggc     2340
aagggcaagg gcaagggcaa gggcaaggct cccgccggcg acggcaacgg gaaggagaag     2400
agcaatggca agcgcttcag gaggttctga gcaaccttga tattattttt ttcttcttt    2460
ccttcaccag ttaattagtt gcctttgatt agaaagagag agagaaa                  2507
```

<210> SEQ ID NO 21
<211> LENGTH: 247
<212> TYPE: PRT
<213> ORGANISM: Myceliophthora thermophila

<400> SEQUENCE: 21

Met Gln Pro Phe Leu Leu Leu Phe Leu Ser Ser Val Thr Ala Ala Ser
1               5                   10                  15

Pro Leu Thr Ala Leu Asp Lys Arg Gln Gln Ala Thr Leu Cys Glu Gln
            20                  25                  30

```
Tyr Gly Tyr Trp Ser Gly Asn Gly Tyr Glu Val Asn Asn Asn Trp
            35                  40                  45

Gly Lys Asp Ser Ala Ser Gly His Gln Cys Thr Tyr Val Asp Ser
 50                  55                  60

Ser Ser Ser Ser Gly Val Ala Trp His Thr Thr Trp Gln Trp Glu Gly
 65                  70                  75                  80

Gly Gln Asn Gln Val Lys Ser Phe Ala Asn Cys Gly Leu Gln Val Pro
                 85                  90                  95

Lys Gly Arg Thr Ile Ser Ser Ile Ser Asn Leu Gln Thr Ser Ile Ser
                100                 105                 110

Trp Ser Tyr Ser Asn Thr Asn Ile Arg Ala Asn Val Ala Tyr Asp Leu
            115                 120                 125

Phe Thr Ala Ala Asp Pro Asn His Ala Thr Ser Ser Gly Asp Tyr Glu
130                 135                 140

Leu Met Ile Trp Leu Ala Arg Phe Gly Asp Val Tyr Pro Ile Gly Ser
145                 150                 155                 160

Ser Gln Gly His Val Asn Val Ala Gly Gln Asp Trp Glu Leu Trp Thr
                165                 170                 175

Gly Phe Asn Gly Asn Met Arg Val Tyr Ser Phe Val Ala Pro Ser Pro
            180                 185                 190

Arg Asn Ser Phe Ser Ala Asn Val Lys Asp Phe Phe Asn Tyr Leu Gln
            195                 200                 205

Ser Asn Gln Gly Phe Pro Ala Ser Ser Gln Tyr Leu Leu Ile Phe Gln
            210                 215                 220

Ala Gly Thr Glu Pro Phe Thr Gly Gly Glu Thr Thr Leu Thr Val Asn
225                 230                 235                 240

Asn Tyr Ser Ala Arg Val Ala
                245

<210> SEQ ID NO 22
<211> LENGTH: 232
<212> TYPE: PRT
<213> ORGANISM: Myceliophthora thermophila

<400> SEQUENCE: 22

Ser Pro Leu Thr Ala Leu Asp Lys Arg Gln Gln Ala Thr Leu Cys Glu
 1               5                  10                  15

Gln Tyr Gly Tyr Trp Ser Gly Asn Gly Tyr Glu Val Asn Asn Asn Asn
                20                  25                  30

Trp Gly Lys Asp Ser Ala Ser Gly Gly His Gln Cys Thr Tyr Val Asp
                35                  40                  45

Ser Ser Ser Ser Ser Gly Val Ala Trp His Thr Thr Trp Gln Trp Glu
 50                  55                  60

Gly Gly Gln Asn Gln Val Lys Ser Phe Ala Asn Cys Gly Leu Gln Val
 65                  70                  75                  80

Pro Lys Gly Arg Thr Ile Ser Ser Ile Ser Asn Leu Gln Thr Ser Ile
                 85                  90                  95

Ser Trp Ser Tyr Ser Asn Thr Asn Ile Arg Ala Asn Val Ala Tyr Asp
                100                 105                 110

Leu Phe Thr Ala Ala Asp Pro Asn His Ala Thr Ser Ser Gly Asp Tyr
            115                 120                 125

Glu Leu Met Ile Trp Leu Ala Arg Phe Gly Asp Val Tyr Pro Ile Gly
130                 135                 140

Ser Ser Gln Gly His Val Asn Val Ala Gly Gln Asp Trp Glu Leu Trp
145                 150                 155                 160
```

```
Thr Gly Phe Asn Gly Asn Met Arg Val Tyr Ser Phe Val Ala Pro Ser
            165                 170                 175

Pro Arg Asn Ser Phe Ser Ala Asn Val Lys Asp Phe Phe Asn Tyr Leu
        180                 185                 190

Gln Ser Asn Gln Gly Phe Pro Ala Ser Ser Gln Tyr Leu Leu Ile Phe
    195                 200                 205

Gln Ala Gly Thr Glu Pro Phe Thr Gly Gly Glu Thr Thr Leu Thr Val
210                 215                 220

Asn Asn Tyr Ser Ala Arg Val Ala
225                 230

<210> SEQ ID NO 23
<211> LENGTH: 741
<212> TYPE: DNA
<213> ORGANISM: Artificial
<220> FEATURE:
<223> OTHER INFORMATION: cDNA encoding MtEG III

<400> SEQUENCE: 23
atgcagccgt tctgctctt gttcctctcg tcggtcacgg cggcgagccc cctgacggcg      60
ctcgacaagc ggcagcaggc gacgttgtgc gagcagtacg ctactggtc gggcaacggt     120
tacgaggtca caacaacaa ctggggcaag gattcggcct cgggcggcca tcagtgcacc     180
tacgtcgaca gcagcagctc cagcggcgtc gcctggcaca cgacctggca gtgggaagga     240
ggccagaacc aggtcaagag cttcgccaac tgcggcctgc aggtgcccaa gggcaggacc     300
atctcgtcca tcagcaacct gcagacctcc atctcgtggt cctacagcaa caccaacatc     360
cgcgccaacg tggcctacga cctcttcacc gcggcagacc cgaaccacgc gaccagcagc     420
ggcgactacg agctcatgat ctggctggcg agattcggcg acgtctaccc catcggctcg     480
tcccagggcc acgtcaacgt ggccggccag gactgggagc tgtggacggg cttcaacggc     540
aacatgcggg tctacagctt cgtagcgccc agcccccgca acagcttcag cgccaacgtc     600
aaggacttct tcaactatct ccagtccaac cagggcttcc cggccagcag ccaataccct     660
ctcatcttcc aggcgggcac cgagcccttc accggcggcg agaccaccct taccgtcaac     720
aactactctg caagggttgc t                                              741

<210> SEQ ID NO 24
<211> LENGTH: 1305
<212> TYPE: DNA
<213> ORGANISM: Myceliophthora thermophila

<400> SEQUENCE: 24
cgacaaagac ccgtcagtga ttaataataa ttagtagcag tttctttctt tcaagactca      60
agaatactcc tttccgccat cgtggcagcg tttagattca tcatgcagcc gtttctgctc     120
ttgttcctct cgtcggtcac ggcggcgagc cccctgacgg cgctcgacaa gcggcagcag     180
gcgacgttgt gcgagcagta cggctactgg tcgggcaacg gttacgaggt caacaacaac     240
aactggggca aggattcggc ctcgggcggc catcagtgca cctacgtcga cagcagcagc     300
tccagcggcg tcgcctggca cacgacctgg cagtgggaag gaggccagaa ccaggtcaag     360
agcttcgcca actgcggcct gcaggtgccc aagggcagga ccatctcgtc catcagcaac     420
ctgcagacct ccatctcgtg gtcctacagc aacaccaaca tccgcgccaa cgtggcctac     480
gacctcttca ccgcggcaga cccgaaccac gcgaccagca gcggcgacta cgagctcatg     540
atctggtcag ttttttttt cttttttctt ttcttctctt tcttttctt ttcctttctc     600
```

```
ctgttttatt ttcttatcca ttgcttcgcc ctctttcctt aaccctgctg actctctctt    660
cttgtcaatg atactgtaat aggctggcga gattcggcga cgtctacccc atcggctcgt    720
cccagggcca cgtcaacgtg gccggccagg actgggagct gtggacgggc ttcaacggca    780
acatgcgggt ctacagcttc gtagcgccca gccccgcaa cagcttcagc gccaacgtca     840
aggacttctt caactatctc cagtccaacc agggcttccc ggccagcagc caataccttc    900
tcagtaagga gacgagatct cgaacagcat accatatatg cgtgcggtac aagtgcacta    960
accccctttt ttttcccgtt cgcagtcttc caggcgggca ccgagcccct taccggcggc   1020
gagaccaccc ttaccgtcaa caactactct gcaaggggttg cttaaacagg aaggccgagg   1080
atggccccca aggccgttgc gggttcacga gctctcttct tttcaagtgc tgtacataca   1140
taattagcgt accaagtcat agctgtttgt cagcttcaaa ctaagtgctc gcccacaaaa   1200 gagggggggag gggaaaataa caaattgccg aacgcagtga taagcttctg ggagcgttga   1260
aagcagtcta cagtaggtgg ctgtacgaag gaaaagagtg cctta                   1305
```

<210> SEQ ID NO 25
<211> LENGTH: 225
<212> TYPE: PRT
<213> ORGANISM: Myceliophthora thermophila

<400> SEQUENCE: 25

```
Met His Leu Ser Ala Thr Thr Gly Phe Leu Ala Leu Pro Ala Leu Ala
  1               5                  10                  15

Leu Ala Gln Leu Ser Gly Ser Gly Gln Thr Thr Arg Tyr Trp Asp Cys
                 20                  25                  30

Cys Lys Pro Ser Cys Ala Trp Pro Gly Lys Gly Pro Ser Ser Pro Val
             35                  40                  45

Gln Ala Cys Asp Lys Asn Asp Asn Pro Leu Asn Asp Gly Gly Ser Thr
         50                  55                  60

Arg Ser Gly Cys Asp Ala Gly Ser Ala Tyr Met Cys Ser Ser Gln
 65                  70                  75                  80

Ser Pro Trp Ala Val Ser Asp Glu Leu Ser Tyr Gly Trp Ala Ala Val
                 85                  90                  95

Lys Leu Ala Gly Ser Ser Glu Ser Gln Trp Cys Cys Ala Cys Tyr Glu
            100                 105                 110

Leu Thr Phe Thr Ser Gly Pro Val Ala Gly Lys Lys Met Ile Val Gln
        115                 120                 125

Ala Thr Asn Thr Gly Gly Asp Leu Gly Asp Asn His Phe Asp Leu Ala
    130                 135                 140

Ile Pro Gly Gly Gly Val Gly Ile Phe Asn Ala Cys Thr Asp Gln Tyr
145                 150                 155                 160

Gly Ala Pro Pro Asn Gly Trp Gly Asp Arg Tyr Gly Gly Ile His Ser
                165                 170                 175

Lys Glu Glu Cys Glu Ser Phe Pro Glu Ala Leu Lys Pro Gly Cys Asn
            180                 185                 190

Trp Arg Phe Asp Trp Phe Gln Asn Ala Asp Asn Pro Ser Val Thr Phe
        195                 200                 205

Gln Glu Val Ala Cys Pro Ser Glu Leu Thr Ser Lys Ser Gly Cys Ser
    210                 215                 220

Arg
225
```

<210> SEQ ID NO 26
<211> LENGTH: 207
<212> TYPE: PRT
<213> ORGANISM: Myceliophthora thermophila

<400> SEQUENCE: 26

```
Gln Leu Ser Gly Ser Gly Gln Thr Thr Arg Tyr Trp Asp Cys Cys Lys
1               5                   10                  15

Pro Ser Cys Ala Trp Pro Gly Lys Gly Pro Ser Ser Pro Val Gln Ala
            20                  25                  30

Cys Asp Lys Asn Asp Asn Pro Leu Asn Asp Gly Gly Ser Thr Arg Ser
        35                  40                  45

Gly Cys Asp Ala Gly Gly Ser Ala Tyr Met Cys Ser Ser Gln Ser Pro
    50                  55                  60

Trp Ala Val Ser Asp Glu Leu Ser Tyr Gly Trp Ala Ala Val Lys Leu
65                  70                  75                  80

Ala Gly Ser Ser Glu Ser Gln Trp Cys Cys Ala Cys Tyr Glu Leu Thr
                85                  90                  95

Phe Thr Ser Gly Pro Val Ala Gly Lys Lys Met Ile Val Gln Ala Thr
            100                 105                 110

Asn Thr Gly Gly Asp Leu Gly Asp Asn His Phe Asp Leu Ala Ile Pro
        115                 120                 125

Gly Gly Gly Val Gly Ile Phe Asn Ala Cys Thr Asp Gln Tyr Gly Ala
    130                 135                 140

Pro Pro Asn Gly Trp Gly Asp Arg Tyr Gly Gly Ile His Ser Lys Glu
145                 150                 155                 160

Glu Cys Glu Ser Phe Pro Glu Ala Leu Lys Pro Gly Cys Asn Trp Arg
                165                 170                 175

Phe Asp Trp Phe Gln Asn Ala Asp Asn Pro Ser Val Thr Phe Gln Glu
            180                 185                 190

Val Ala Cys Pro Ser Glu Leu Thr Ser Lys Ser Gly Cys Ser Arg
        195                 200                 205
```

<210> SEQ ID NO 27
<211> LENGTH: 675
<212> TYPE: DNA
<213> ORGANISM: Artificial
<220> FEATURE:
<223> OTHER INFORMATION: cDNA encoding MtEG V

<400> SEQUENCE: 27

```
atgcatctct ccgccaccac cgggttcctc gccctcccgg ccctggccct ggcccagctc      60
tcgggcagcg gccagacgac ccggtactgg gactgctgca agccgagctg cgcctggccc     120
ggcaagggcc cctcgtctcc ggtgcaggcc tgcgacaaga acgacaaccc gctcaacgac     180
ggcggctcca cccggtccgg ctgcgacgcg ggcggcagcg cctacatgtg ctcctcccag     240
agcccctggg ccgtcagcga cgagctgtcg tacggctggg cggccgtcaa gctcgccggc     300
agctccgagt cgcagtggtg ctgcgcctgc tacgagctga ccttcaccag cgggccggtc     360
gcgggcaaga agatgattgt gcaggcgacc aacaccggtg gcgacctggg cgacaaccac     420
tttgacctgg ccatccccgg tggcggtgtc ggtattttca acgcctgcac cgaccagtac     480
ggcgctcccc cgaacggctg gggcgaccgc tacgcggca tccattccaa ggaagagtgc     540
gaatccttcc cggaggccct caagcccggc tgcaactggc gcttcgactg gttccaaaac     600
gccgacaacc cgtcggtcac cttccaggag gtggcctgcc cgtcggagct cacgtccaag     660
agcggctgct cccgt                                                      675
```

<210> SEQ ID NO 28
<211> LENGTH: 1448
<212> TYPE: DNA
<213> ORGANISM: Myceliophthora thermophila

<400> SEQUENCE: 28

```
atatataagt gagagtgttt tttgactgcc ccgggttctg gtagttgaag ggaagttcga      60
tgctctctgc tgtcgtcgct ctcgtcgctc tcgtcggcat cctccatccg tccgcctttg     120
ataacccgct ccccgactca gtcaagacga cgcatacttg gcaccatgca tctctccgcc     180
accaccgggt tcctcgccct ccggccctg gccctggccc agctctcggg cagcggccag      240
acgacccggt actgggactg ctgcaagccg agctgcgcct ggcccggcaa gggcccctcg     300
tctccggtgc aggcctgcga caagaacgac aacccgctca cgacggcgg ctccacccgg      360
tccggctgcg acgcgggcgg cagcgcctac atgtgctcct cccagagccc ctgggccgtc     420
agcgacgagc tgtcgtacgg ctgggcggcc gtcaagctcg ccggcagctc cgagtcgcag     480
tggtgctgcg cctgctacga gctgaccttc accagcgggc cggtcgcggg caagaagatg     540
attgtgcagg cgaccaacac cggtggcgac ctgggcgaca ccactttga cctgccgtg      600
agttgcctcc ccttctcccc ggaccgctca gattagatga gattagactt tgctcgtaaa     660
tcggtccaag attcccgttg actgaccaac aaacatcata cgggcagatc cccggtggcg     720
gtgtcggtat tttcaacggt aagctggtgc ccccggaccc ctccccggac ccctcccct      780
tttcctccag cgagccgagt tgggatcgcg agatcgaga actcacacaa cttctctctc     840
gacagcctgc accgaccagt acggcgctcc cccgaacggc tggggcgacc gctacggcgg     900
catccattcc aaggaagagt gcgaatcctt cccggaggcc ctcaagcccg gctgcaactg     960
gcgcttcgac tggtacgttg ctttgacata ccggaaccca attcctccaa cccccccct    1020
tttctccccc aactccgggg gtagtcggaa tgtcgcgact gacccctattt caggttccaa    1080
aacgccgaca acccgtcggt caccttccag gaggtggcct gccgtcgga gctcacgtcc     1140
aagagcggct gctcccgtta agagggaaga gaggggctg gaaggaccga aagattcaac    1200
ctctgctcct gctggggaag ctcgggcgcg agtgtgaaac tggtgtaaat attgtggcac    1260
acacaagcta ctacagtccg tctcgccgtc cggctaacta gccttgctgc ggatctgtcc   1320
atcttcggtc cgaactgtcc gttgctgttt tggctcggtg cctcatcttc tcccaaccta    1380
gtcaagaatg aatcgtgaga gaggctgaga gagataagat cgacttcaga aatccagggt    1440
tgaaagca                                                              1448
```

<210> SEQ ID NO 29
<211> LENGTH: 381
<212> TYPE: PRT
<213> ORGANISM: Myceliophthora thermophila

<400> SEQUENCE: 29

```
Met Arg Val Ser Ser Leu Val Ala Ala Leu Ala Thr Gly Gly Leu Val
 1               5                  10                  15

Ala Ala Thr Pro Lys Pro Lys Gly Ser Ser Pro Pro Gly Ala Val Asp
            20                  25                  30

Ala Asn Pro Phe Lys Gly Lys Thr Gln Phe Val Asn Pro Ala Trp Ala
        35                  40                  45

Ala Lys Leu Glu Gln Thr Lys Lys Ala Phe Leu Ala Arg Asn Asp Thr
    50                  55                  60
```

Val Asn Ala Ala Lys Thr Glu Lys Val Gln Gln Thr Ser Ser Phe Val
 65                  70                  75                  80

Trp Val Ser Arg Ile Ala Glu Leu Ser Asn Ile Asp Asp Ala Ile Ala
                 85                  90                  95

Ala Ala Arg Lys Ala Gln Lys Lys Thr Gly Arg Arg Gln Ile Val Gly
            100                 105                 110

Leu Val Leu Tyr Asn Leu Pro Asp Arg Asp Cys Ser Ala Gly Glu Ser
        115                 120                 125

Ala Gly Glu Leu Ser Ser Asp Lys Asn Gly Leu Glu Ile Tyr Lys Thr
    130                 135                 140

Glu Phe Val Lys Pro Phe Ala Asp Lys Val Ala Ala Lys Asp Leu
145                 150                 155                 160

Asp Phe Ala Ile Val Leu Glu Pro Asp Ser Leu Ala Asn Leu Val Thr
                165                 170                 175

Asn Leu Gly Ile Glu Phe Cys Ala Asn Ala Ala Pro Val Tyr Arg Glu
            180                 185                 190

Gly Ile Ala Tyr Ala Ile Ser Ser Leu Gln Gln Pro Asn Val His Leu
        195                 200                 205

Tyr Ile Asp Ala Ala His Gly Gly Trp Leu Gly Trp Asp Asp Asn Leu
210                 215                 220

Pro Leu Ala Ala Lys Glu Phe Ala Glu Val Val Lys Leu Ala Gly Glu
225                 230                 235                 240

Gly Lys Lys Ile Arg Gly Phe Val Thr Asn Val Ser Asn Tyr Asn Pro
                245                 250                 255

Phe His Ala Val Arg Glu Asn Phe Thr Glu Trp Ser Asn Ser Trp
            260                 265                 270

Asp Glu Ser His Tyr Ala Ser Ser Leu Thr Pro Phe Leu Glu Lys Glu
        275                 280                 285

Gly Leu Pro Ala Arg Phe Ile Val Asp Gln Gly Arg Val Ala Leu Pro
    290                 295                 300

Gly Ala Arg Lys Glu Trp Gly Glu Trp Cys Asn Val Ala Pro Ala Gly
305                 310                 315                 320

Phe Gly Pro Ala Pro Thr Thr Arg Val Asn Asn Thr Val Val Asp Ala
                325                 330                 335

Leu Val Trp Val Lys Pro Gly Gly Glu Ser Asp Gly Glu Cys Gly Leu
            340                 345                 350

Ala Gly Ala Pro Lys Ala Gly Gln Trp Phe Asp Glu Tyr Ala Gln Met
        355                 360                 365

Leu Val Glu Asn Ala His Pro Ser Val Val His Lys Trp
    370                 375                 380

<210> SEQ ID NO 30
<211> LENGTH: 363
<212> TYPE: PRT
<213> ORGANISM: Myceliophthora thermophila

<400> SEQUENCE: 30

Thr Pro Lys Pro Lys Gly Ser Ser Pro Pro Gly Ala Val Asp Ala Asn
1               5                   10                  15

Pro Phe Lys Gly Lys Thr Gln Phe Val Asn Pro Ala Trp Ala Ala Lys
            20                  25                  30

Leu Glu Gln Thr Lys Lys Ala Phe Leu Ala Arg Asn Asp Thr Val Asn
        35                  40                  45

Ala Ala Lys Thr Glu Lys Val Gln Gln Thr Ser Ser Phe Val Trp Val
    50                  55                  60

```
Ser Arg Ile Ala Glu Leu Ser Asn Ile Asp Asp Ala Ile Ala Ala
 65                  70                  75                  80

Arg Lys Ala Gln Lys Lys Thr Gly Arg Arg Gln Ile Val Gly Leu Val
                 85                  90                  95

Leu Tyr Asn Leu Pro Asp Arg Asp Cys Ser Ala Gly Glu Ser Ala Gly
            100                 105                 110

Glu Leu Ser Ser Asp Lys Asn Gly Leu Glu Ile Tyr Lys Thr Glu Phe
        115                 120                 125

Val Lys Pro Phe Ala Asp Lys Val Ala Ala Lys Asp Leu Asp Phe
130                 135                 140

Ala Ile Val Leu Glu Pro Asp Ser Leu Ala Asn Leu Val Thr Asn Leu
145                 150                 155                 160

Gly Ile Glu Phe Cys Ala Asn Ala Ala Pro Val Tyr Arg Glu Gly Ile
                165                 170                 175

Ala Tyr Ala Ile Ser Ser Leu Gln Gln Pro Asn Val His Leu Tyr Ile
            180                 185                 190

Asp Ala Ala His Gly Gly Trp Leu Gly Trp Asp Asp Asn Leu Pro Leu
        195                 200                 205

Ala Ala Lys Glu Phe Ala Glu Val Val Lys Leu Ala Gly Glu Gly Lys
210                 215                 220

Lys Ile Arg Gly Phe Val Thr Asn Val Ser Asn Tyr Asn Pro Phe His
225                 230                 235                 240

Ala Val Val Arg Glu Asn Phe Thr Glu Trp Ser Asn Ser Trp Asp Glu
                245                 250                 255

Ser His Tyr Ala Ser Ser Leu Thr Pro Phe Leu Glu Lys Glu Gly Leu
            260                 265                 270

Pro Ala Arg Phe Ile Val Asp Gln Gly Arg Val Ala Leu Pro Gly Ala
        275                 280                 285

Arg Lys Glu Trp Gly Glu Trp Cys Asn Val Ala Pro Ala Gly Phe Gly
290                 295                 300

Pro Ala Pro Thr Thr Arg Val Asn Asn Thr Val Val Asp Ala Leu Val
305                 310                 315                 320

Trp Val Lys Pro Gly Gly Glu Ser Asp Gly Cys Gly Leu Ala Gly
                325                 330                 335

Ala Pro Lys Ala Gly Gln Trp Phe Asp Glu Tyr Ala Gln Met Leu Val
            340                 345                 350

Glu Asn Ala His Pro Ser Val Val His Lys Trp
        355                 360

<210> SEQ ID NO 31
<211> LENGTH: 1143
<212> TYPE: DNA
<213> ORGANISM: Artificial
<220> FEATURE:
<223> OTHER INFORMATION: cDNA encoding MtEG VI

<400> SEQUENCE: 31
atgcgcgtct ctagtttggt cgcggccctt gctaccggtg gtcttgtcgc cgccacgcct      60
aagcccaagg ggtcgtcgcc ccctggggcc gtggacgcga accctttcaa gggcaagacg     120
cagttcgtca acccggcatg gcggccaag ctggaacaga ccaaaaaggc gttcctggcc      180
aggaacgaca ccgtcaatgc cgccaagacg gagaaggtcc agcagaccag ctcgttcgtc     240
tgggtctcga ggatcgccga gctctccaac atcgacgacg ccatcgcggc tgcccgcaag     300
gcgcagaaga agacgggcag gaggcagatc gtcggcctgg tgctctacaa ccttccggac     360
```

```
cgcgactgca gcgcgggcga gagcgcgggc gagctcagca gcgacaagaa cgggctcgag    420
atctacaaga ctgagttcgt caagcccttc gccgacaagg tggcggccgc aaaggacctc    480
gacttcgcca tcgtcctgga gcccgactcg ctggccaacc tggtcaccaa cctgggcatc    540
gagttctgcg ccaacgccgc ccccgtctac cgcgagggca tcgcctatgc catctccagc    600
cttcagcagc aaacgtgca cttgtacatc gatgctgccc acggcggctg gctcggctgg    660
gacgacaacc tgccgctggc cgccaaggag tttgccgagg tggtcaagct tgccggcgag    720
ggcaagaaga tccgcggctt cgtcaccaac gtgtccaact acaacccctt ccacgccgtc    780
gtgcgcgaga actttaccga gtggagcaac tcgtgggacg agtctcacta cgcctcctcg    840
ctcacaccgt tcctcgagaa agaggggctg ccggcacgct tcatcgtcga ccagggtcgc    900
gttgccctcc cggagcccg caaggagtgg ggtgaatggt gcaacgtggc acccgccgga    960
tttggccccg cgcccacgac cagggtcaac aacaccgtcg tcgatgctct cgtctgggtc   1020
aagcctggcg gcgagagcga cggcgagtgt ggcttggctg gcgcccccaa ggccggccag   1080
tggttcgacg agtacgccca gatgctggtc gagaatgccc accgtctgt cgtccacaag   1140
tgg                                                                 1143

<210> SEQ ID NO 32
<211> LENGTH: 1658
<212> TYPE: DNA
<213> ORGANISM: Myceliophthora thermophila

<400> SEQUENCE: 32
aggaacgggg aggaggaggg cttggttagg gtcgcgttcg tttggagatt gctgagctct     60
gagccttcgg tccttggatc cctgcggtcc ccggtctcct ctctctctct ctctctctct    120
ctctctctct cttcttccca cgctcgttcg acagacgcct ccccttcttc gctctccttt    180
ccctcgcacg tagcacacta atagtgcacc atgcgcgtct ctagtttggt cgcggccctt    240
gctaccggtg gtcttgtcgc cgccacgcct aagcccaagg ggtcgtcgcc ccctggggcc    300
gtggacgcga acccttttcaa gggcaagacg cagttcgtca acccggcatg ggcggccaag    360
ctggaacaga ccaaaaaggc gttcctggcc aggaacgaca ccgtcaatgc cgccaagacg    420
gagaaggtcc agcagaccag ctcgttcgtc tgggtctcga ggatcgccga gctctccaac    480
atcgacgacg ccatcgcggc tgcccgcaag gcgcagaaga agacgggcag gaggcagatc    540
gtcggcctgg tgctctacaa ccttccggac cgcgactgca gcgcgggcga gagcgcgggc    600
gagctcagca gcgacaagaa cgggctcgag atctacaaga ctgagttcgt caagcccttc    660
gccgacaagg tggcggccgc aaaggacctc gacttcgcca tcgtcctgga gcccgactcg    720
ctggccaacc tggtcaccaa cctgggcatc gagttctgcg ccaacgccgc ccccgtctac    780
cgcgagggca tcgcctatgc catctccagc cttcagcagc aaacgtgca cttgtacatc    840
gatgctgccc acggcggctg gctcggctgg gacgacaacc tgccgctggc cgccaaggag    900
tttgccgagg tggtcaagct tgccggcgag ggcaagaaga tccgcggctt cgtcaccaac    960
gtgtccaact acaacccctt ccacgccgtc gtgcgcgaga actttaccga gtggagcaac   1020
tcgtgggacg agtctcacta cgcctcctcg ctcacaccgt tcctcgagaa agaggggctg   1080
ccggcacgct tcatcgtcga ccagggtcgc gttgccctcc cggagcccg caaggagtgg   1140
tgagtttcga ccagattgac cctcgaccca tgcaccgag attgctgacg attgaattgc   1200
gtgtcccgtc ccccaggggt gaatggtgca acgtggcacc cgccggattt ggccccgcgc   1260
```

```
ccacgaccag ggtcaacaac accgtcgtcg atgctctcgt ctgggtcaag cctggcggcg         1320
agagcgacgg cgagtgtggc ttggctggcg cccccaaggc cggccagtgg ttcgacgagt         1380
acgcccagat gctggtcgag aatgcccacc cgtctgtcgt ccacaagtgg tagataaatt         1440
ttggagtccg agaagggtcc cagatagact tttgttttaa aacaaaatgc aaggtgtcga         1500
cagatactgg cttaacatta accaagcacc atgaacatga cttgtcaaca tattgataca         1560
ttccgctgct ttcccatacg tgctctcagg tctcagggat caaatggata ggtcggtaat         1620
gcaaaacgat ccattggata tccagaagag agaaaaaa                                 1658
```

ENZYMATIC ACTIVITY OF LYTIC POLYSACCHARIDE MONOOXYGENASE

CROSS-REFERENCE TO RELATED APPLICATIONS

This application is the National Stage application of International Application No. PCT/EP/16/55354, filed on Mar. 11, 2016, which is related to and claims the benefit of priority to European Patent Application No. EP15158572.6, filed on Mar. 11, 2015, both of which are incorporated by reference in their entireties.

SEQUENCE LISTING

The content of the electronically submitted sequence listing in ASCII text (File Name: NB36011WOPCT$_{13}$ Seql-st.txt; Size 85,895 bytes) is incorporated by reference in its entirety.

FIELD OF THE INVENTION

The present invention is in the area of enzymes for (hemi-)cellulose degradation and/or modification, more in particular the degradation and/or modification of xylan. The invention is based on a newly discovered enzymatic activity of a class of lytic polysaccharide monooxygenases (LPMOs), i.e. oxidative cleavage of xylan in addition to oxidative cleavage of cellulose. The present invention therefore relates to a method for degrading and/or modifying xylan in a xylan-comprising substrate, a method for preparing a product from a xylan-comprising substrate, a kit of parts, a liquid, paste or solid formulation, and a xylan-comprising composition, comprising said LPMO. The invention further relates to a use of said LPMO, said kit of parts, said formulation and/or said composition, in a method of the invention.

BACKGROUND OF THE INVENTION

Effective degradation of plant biomass into monosaccharides, which are useful building blocks for biochemicals or biofuels, requires a variety of hydrolytic and oxidative enzymes. Such enzymes are preferably thermo-tolerant, since the rigidity of the plant cell walls asks for a thermo-assisted pre-treatment as a first step to increase the accessibility of cell wall polysaccharides (1). Commercial enzyme cocktails for plant cell wall degradation mostly comprise enzymes produced by filamentous fungi like *Aspergillus*, *Trichoderma* and *Talaromyces* strains. In addition, the commercially available fungus *Myceliophthora thermophila* C1 is a good candidate for the production of thermo-tolerant carbohydrate-active enzymes (2). Still, improvement of already existing enzyme cocktails is required for the success of enzyme-driven biorefinery processes.

Secondary plant cell walls are built from a matrix of cellulose fibrils, interacting with hemicelluloses and glued together with a network of phenolic lignin (3-5). The majority of hemicelluloses is composed of xylan, mannan, and xylo-glucan building blocks, having backbones of β-(1→4) linked xylosyl residues, β-(1→4) linked mannosyl or β-(1→4) linked glucosyl residues, respectively (6). Such hemicelluloses are strongly associated with cellulose via hydrogen-bonding, especially the ones with a low amount of substitution or a block-wise distribution of substituents (3, 5). The cellulose-associated hemicelluloses block cellulases to reach their target substrate, which is likely to contribute to the defense of the plant against microbial attack. Also, hemicelluloses inhibit the deconstruction of plant polysaccharides by commercial enzymes (7, 8) in the formation of fermentable monosaccharides. Hence, degradation of these cellulose-associated hemicelluloses is essential to improve cellulose hydrolysis from plant biomass. As xylan is the main component of hemicellulose, enzymes degrading xylan play a major role in hemicellulose degradation.

Xylan degrading and/or modifying enzymes are broadly applied in industry, such as in upgrading of animal food, in improving the quality of baking and brewing products, in bleaching and modification soft and hardwood kraft pulp, in paper recycling, in macerating vegetables and fruits, in clarifying cereal solution and fruit juices, and in the production of bio fuel and/or other chemicals from residues produced by agriculture and forestry. However, in many of the practical applications, the use of enzymes for xylan degradation and/or modification is not straightforward; the enzymes must be active in the temperature and pH conditions of the process in which they are used. For instance, formulation of commercial feed using pelleting, extrusion or expansion, often contains steps involving high temperatures (70-180° C.) and requires enzymes that withstand these conditions. Furthermore, bleaching processes, and even the sequence of the steps used in the bleaching process, vary among different pulp mills and therefore provide for specific requirements to the enzymes used in these processes. Because of the heterogeneity and complex chemical nature of plant xylan and the broad and heterogenic nature of the applications, there is thus a continuous need to find new xylan degrading and/or modifying enzyme activity, preferably active in different temperature and pH conditions.

Thus, it is an object of the present invention to provide for new means and methods for modifying and/or degrading xylans. The invention provides a newly discovered enzyme activity of a class of fungal enzymes, i.e. thermo-tolerant lytic polysaccharide monooxygenases (LPMOs). A LPMO of the invention is an auxiliary activity family 9 (AA9) LPMO, previously known as GH61 enzymes. These enzymes are described to have cellulolytic and cellulolytic enhancing activities (Morgenstern et al., 2014, Fungal cellulose degradation by oxidative enzymes: from dysfunctional GH61 family to powerful lytic polysaccharide monooxygenase family, Briefings in Functional Genomics, 13 (6): 421-423). The inventors discovered that the LPMO of the invention not only cleaves celluloses but also cleaves xylans, e.g. in cellulose-associated xylan under formation of oxidised xylo- and gluco-oligomers. In addition, the LPMO displays a synergistic effect when acting together with endoglucanases. The invention further provides methods of using the novel LPMO in a variety of application requiring the cleavage of cellulose and/or xylans.

DESCRIPTION OF THE INVENTION

Definitions

As used herein, the terms "lignin", "lignen", "saccharification", "fermentable sugars", "biomass", "lignocellulosic material", "agricultural biomass", "energy crops", "cellulose" and "hemicellulose" are to be understood herein as defined in WO2013/159005 A2.

As used herein, "oxidoreductase", "oxidase", "monooxygenases", "hydroxylases" "dehydrogenases", "cellobiose dehydrogenase", "cellobiose dehydrogenases", "cellobiose oxidases", "carbohydrase", "glycoside hydrolase", "glycosyl hydrolase", "glycosidase", "endoglucanase", "cellobiohydrolase" and "hemicellulose", "xylanase", "β-mannanase", "endo-1,4-β-mannosidase", "mannan endo-1,6-α-mannosidase", "β-mannosidase", "galactanase", "endo-β-1,6-galactanse", "arabinogalactan endo-1,4-β-galactosidase", "glucoamylase" "β-hexosaminidase", "β-N-acetylglucosaminidase", "α-L-arabinofuranosidase", "α-N-arabinofuranosidase", "α-arabinofuranosidase", "arabinosidase", "arabinofuranosidase", "endo-arabinase", "exo-arabinase", "β-xylosidase", "chitosanase", "exo-polygalacturonase", "acetyl xylan esterase", "acetyl mannan esterase", "ferulic esterase", "ferulic acid esterase", "coumaric acid esterase", "pectate lyase", "pectin lyases", "endo-1,3-β-glucanase", "laminarinase", "lichenase", "glycosidases" and "ligninase" are to be understood herein as defined in WO 2013/159005 A2.

As used herein, reference to an "enzyme" includes full-length naturally occurring or wild-type enzymes or proteins (the terms enzyme and protein are used herein interchangeably) and their glycosylated or otherwise modified forms, fusion proteins, or any fragment or homologue or variant of such an enzyme or protein. Preferably, an enzyme is an isolated enzyme or protein. An isolated enzyme or protein, is to be understood herein as an enzyme or protein (including a polypeptide or peptide) that has been removed from its natural milieu (i.e., that has been subject to human manipulation) and can include purified proteins, partially purified proteins, recombinantly produced proteins, synthetically produced proteins, proteins complexed with lipids, soluble proteins, and isolated proteins associated with other proteins, for example. As such, "isolated" does not reflect the extent to which the protein has been purified. Preferably, an isolated protein is produced recombinantly. In addition, and by way of example, a "*M. thermophila* protein" or "*M. thermophila* enzyme" refers to a protein (generally including a homologue or variant of a naturally occurring protein) from *Myceliophthora thermophila* or to a protein that has been otherwise produced from the knowledge of the structure (e.g., sequence) and preferably the function of a naturally occurring protein from *Myceliophthora thermophila*. In other words, a *M. thermophila* protein includes any protein that has substantially similar structure and function of a naturally occurring *M. thermophila* protein or that is a biologically active (i.e., has biological activity) homologue or variant of a naturally occurring protein from *M. thermophila* as described in detail herein. As such, a *M. thermophila* protein can include purified, partially purified, recombinant, mutated/modified and synthetic proteins.

As used herein, the phrase "biological activity" of a protein refers to any function(s) exhibited or performed by the protein that is ascribed to the naturally occurring form of the protein as measured or observed in vitro or in vivo. A protein fragment preferably comprises a domain of a protein that has the catalytic activity of the full-length enzyme. A protein fragment includes, but is not limited to, a fragment comprising a catalytic domain (CD) and/or a carbohydrate binding module (CBM). For example, a protein fragment may comprise a CD of a protein but not a CBM of the protein or a CBM of a protein but not a CD. Similarly, domains from different proteins may be combined. Protein fragments comprising a CD, CBM or combinations thereof for each protein disclosed herein can be readily produced using standard techniques known in the art.

An enzyme or protein, including a biologically active homologue, variant, or fragment thereof, has at least one characteristic of biological activity of a wild-type, or naturally occurring protein. As discussed above, in general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). The biological activity of a protein as disclosed herein can include an enzyme activity (catalytic activity and/or substrate binding activity), such as oxidases, oxygenases, monoxygenases, Baeyer-Villiger monooxygenases, dioxygenases, peroxidases, dehydrogenases, reductases that catalyze an oxidation-reduction reaction or any other activity disclosed herein. Specific biological activities of the proteins disclosed herein are described in detail herein and in the Examples. Methods of detecting and measuring the biological activity of a protein as disclosed herein include, but are not limited to, the assays described in the Examples section below. Such assays include, but are not limited to, measurement of enzyme activity (e.g., catalytic activity), measurement of substrate binding, and the like. Additional assays and methods for examining the activity of the enzymes are found in U.S. Patent Applications 60/806, 876, 60/970,876, Ser. Nos. 11/487,547, 11/775,777, 11/833, 133, and 12/205,694 and incorporated herein by reference.

It is noted that an enzyme or protein (including homologues or variants) is not required to have a biological activity such as catalytic activity. A protein can be a truncated, mutated or inactive protein, or lack at least one activity of the wild-type enzyme, for example. Inactive proteins may be useful in some screening assays. Methods to measure protein expression levels of a protein include, but are not limited to: western blotting, immunocytochemistry, flow cytometry or other immunologic-based assays; assays based on a property of the protein including but not limited to, ligand binding or interaction with other protein partners.

Modifications of a protein, such as in a homologue or variant, may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action of a protein. Similarly, modifications that result in an increase in protein expression or an increase in the activity of the protein, can be referred to as amplification, overproduction, activation, enhancement, up-regulation or increased action of a protein.

As used herein, the terms "modification," "mutation," and "variant" can be used interchangeably with regard to the modifications/mutations to the amino acid sequence of a *M. thermophila* protein (or nucleotide sequences) described herein.

The term "modification" can also be used to describe post-translational modifications to a protein or peptide including, but not limited to, methylation, farnesylation, carboxymethylation, geranyl geranylation, glycosylation, phosphorylation, acetylation, myristoylation, prenylation, palmitation, and/or amidation. Modification can also include the cleavage of a signal peptide, or methionine, or other portions of the peptide that require cleavage to generate the mature peptide.

As used herein, the terms "homologue" or "variants" are used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to:

changes in one or a few amino acid side chains; changes one or a few amino acids, including deletions (e.g., a truncated version of the protein or peptide), insertions and/or substitutions; changes in stereochemistry of one or a few atoms; and/or minor derivatizations, including but not limited to for example: methylation, glycosylation and phosphorylation. A homologue or variant can have either enhanced, decreased, or substantially similar properties as compared to the naturally occurring protein or peptide. A homologue or variant can include an agonist of a protein or an antagonist of a protein.

Homologues or variants can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Homologous can also be the result of a gene duplication and rearrangement, resulting in a different location. Allelic variants typically encode proteins having similar activity to that of the protein encoded by the gene to which they are being compared. One class of allelic variants can encode the same protein but have different nucleotide sequences due to the degeneracy of the genetic code. Allelic variants can also comprise alterations in the 5' or 3' untranslated regions of the gene (e.g., in regulatory control regions). Allelic variants are well known to those skilled in the art.

Homologues or variants can be produced using techniques known in the art for the production of proteins including, but not limited to, direct modifications to the naturally occurring protein, direct protein synthesis, or modifications to the nucleotide sequence encoding the protein using, for example, classic or recombinant DNA techniques to effect random or targeted mutagenesis.

A modified protein also includes a fusion protein that includes a domain of a protein as disclosed herein (including a homologue or variant) attached to one or more fusion segments, which are typically heterologous in sequence to the protein sequence (i.e., different than protein sequence). Suitable fusion segments in a modified protein include, but are not limited to, segments that can: enhance a protein's stability; provide other desirable biological activity; and/or assist with the purification of the protein (e.g., by affinity chromatography). A suitable fusion segment can be a domain of any size that has the desired function (e.g., imparts increased stability, solubility, action or biological activity; and/or simplifies purification of a protein). Fusion segments can be joined to amino and/or carboxyl termini of the domain of a protein as disclosed herein and can be susceptible to cleavage in order to enable straight-forward recovery of the protein. Fusion proteins are preferably produced by culturing a recombinant cell transfected with a fusion nucleic acid molecule that encodes a protein including the fusion segment attached to either the carboxyl and/or amino terminal end of a domain of a protein as disclosed herein. Accordingly, proteins as disclosed herein also include expression products of gene fusions (for example, used to overexpress soluble, active forms of the recombinant protein), of mutagenized genes (such as genes having codon modifications to enhance gene transcription and translation), and of truncated genes (such as genes having membrane binding modules removed to generate soluble forms of a membrane protein, or genes having signal sequences removed which are poorly tolerated in a particular recombinant host).

A modified protein also includes a protein as disclosed that has been modified by conservative amino acid substitution. "Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

A protein or polypeptide defined as "consisting essentially of" a specified amino acid sequence, is an amino acid sequences described herein produced from at least one, and up to about 20, additional heterologous amino acids flanking each of the C- and/or N-terminal ends of the specified amino acid sequence. Heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleotide sequence encoding the specified amino acid sequence as it occurs in the gene, if such nucleotides in the naturally occurring sequence were translated using standard codon usage for the organism from which the given amino acid sequence is derived. In addition, and solely by way of example, a protein referenced as being derived from is derived from a particular organism, such as a fungus as defined herein above.

Many of the enzymes and proteins disclosed herein may be desirable targets for modification and use in the processes described herein. These proteins have been described in terms of function and amino acid sequence (and nucleotide sequence encoding the same) of representative wild-type proteins. Homologues or variants of a protein encompassed preferably comprise, consist essentially of, or consist of, an amino acid sequence that is at least 35%, 45%, 55%, 65%, 70%, 75%, 80%, 90%, identical, and more preferably at least 95% identical, 96%, 97%, identical, and most preferably at least about 99% identical, or any percent identity between 35% and 99%, in whole integers (i.e., 36%, 37%, etc.), to an amino acid sequence disclosed herein that represents the amino acid sequence of an enzyme or protein disclosed herein (including a biologically active domain of a full-length protein). Preferably, the amino acid sequence of the homologue or variant has a biological activity of the wild-type or reference protein or of a biologically active domain thereof (e.g., a catalytic domain). When denoting mutation positions, the amino acid position of the wild-type is typically used. The wild-type can also be referred to as the "parent". Additionally, any generation before the variant at issue can be a parent.

The minimum size of a protein and/or homologue, variant or fragment is a size sufficient to have biological activity or, when the protein is not required to have such activity, sufficient to be useful for another purpose associated with a protein as disclosed herein, such as for the production of antibodies that bind to a naturally occurring protein. Preferably, the protein disclosed herein is at least 20, 25, 30, 40, 50, 60, 70, 80, 90, 100, 125, 150, 175, 200, 250 amino acids in length, and so on up to a full length of each protein, and including any size in between in increments of one whole integer (one amino acid). There is no limit, other than a practical limit, on the maximum size of such a protein in that the protein can include a portion of a protein or a full-length protein, plus additional sequence (e.g., a fusion protein sequence), if desired.

As used herein, unless otherwise specified, reference to a percent (%) identity refers to an evaluation of homology which is performed using: 1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402); 2) a BLAST 2 alignment (using the parameters described below); 3) PSI-BLAST with the standard default parameters (Position-Specific Iterated BLAST; and/or 4) CAZy homology determined using standard default parameters from the Carbohydrate Active EnZymes database (Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12) and/or applying a similar strategy using databases such as the Foly database (website: foly.esil.univ-mrs.fr) and the PeroxiBase (website: peroxibase.isb-sib.ch).

It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues or variants. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174:247-250. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

Unless otherwise indicated herein, identity with a given SEQ ID NO means identity based on the full length of said sequence (i.e. over its whole length or as a whole).

As used herein, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" or being "100% identical" with a second sequence means that the first sequence exactly matches the second sequence with no gaps between nucleotides or amino acids. A protein as disclosed herein, including a homologue or variant, preferably includes a protein having an amino acid sequence that is sufficiently similar to a natural amino acid sequence that a nucleotide sequence encoding the homologue or variant is capable of hybridizing under moderate, high or very high stringency conditions (described below) to (i.e., with) a nucleic acid molecule encoding the natural protein (i.e., to the complement of the nucleic acid strand encoding the natural amino acid sequence). Preferably, a homologue or variant of a protein is encoded by a nucleic acid molecule comprising a nucleotide sequence that hybridizes under low, moderate, or high stringency conditions to the complement of a nucleotide sequence that encodes a protein comprising, consisting essentially of, or consisting of, an amino acid sequence represented by any of SEQ ID NOs 1-6. Such hybridization conditions are described in detail below.

A nucleotide sequence complement of nucleotide sequence encoding a protein as disclosed herein refers to the nucleotide sequence of the nucleic acid strand that is complementary to the strand, which encodes the protein. It will be appreciated that a double stranded DNA which encodes a given amino acid sequence comprises a single strand DNA and its complementary strand having a sequence that is a complement to the single strand DNA. As such, nucleic acid molecules can be either double-stranded or single-stranded, and include those nucleic acid molecules that form stable hybrids under stringent hybridization conditions with a nucleotide sequence that encodes an amino acid sequence such as the amino acid sequences of SEQ ID NOs 1-6 or a nucleotide sequence of SEQ ID NOs 7-9. Methods to deduce a complementary sequence are known to those skilled in the art. It should be noted that since nucleic acid sequencing technologies are not entirely error-free, the sequences presented herein, at best, represent apparent sequences of the proteins disclosed herein.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Labo-* ratory Manual, Cold Spring Harbor Labs Press, 1989. Sambrook et al., ibid., (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid.

More particularly, moderate stringency hybridization and washing conditions, as referred to herein, refer to conditions which permit isolation of nucleic acid molecules having at least about 70% nucleotide sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleotide sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleotide sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. Preferably, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. Preferably, stringent hybridization conditions for DNA:RNA hybrids include hybridization at an ionic strength of 6×SSC (0.9 M Na$^1$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature (Tm) for molecules larger than about 100 nucleotides, 0% formamide and a G+C content of about 40%. Alternatively, Tm can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated Tm of a particular hybrid, and wash conditions typically include a combination of salt and temperature conditions that are approximately 12-20° C. below the calculated Tm of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

A nucleic acid molecule includes a nucleic acid molecule comprising, consisting essentially of, or consisting of, a nucleotide sequence encoding any of the enzymes or proteins disclosed herein, including a fragment or a homologue or variant of such proteins, described above. Nucleic acid molecules can include a nucleotide sequence that encodes a fragment of a protein that does not have biological activity, and can also include portions of a gene or polynucleotide encoding the protein that are not part of the coding region for the protein (e.g., introns or regulatory regions of a gene encoding the protein). Nucleic acid molecules can include a nucleotide sequence that is useful as a probe or primer (oligonucleotide sequences). Preferably, a nucleic acid molecule is an isolated nucleic acid molecule. As used herein, an isolated nucleic acid molecule is a nucleic acid molecule (polynucleotide) that has been removed from its natural milieu (i.e., that has been subject to human manipulation) and can include DNA, RNA, or derivatives of either DNA or RNA, including cDNA. As such, "isolated" does not reflect the extent to which the nucleic acid molecule has been purified. Although the phrase "nucleic acid molecule" primarily refers to the physical nucleic acid molecule, and the phrase "nucleotide sequence" primarily refers to the sequence of nucleotides on the nucleic acid molecule, the two phrases can be used interchangeably, especially with respect to a nucleic acid molecule, or a nucleotide sequence, being capable of encoding a protein. An isolated nucleic acid molecule can be isolated from its natural source or produced using recombinant DNA technology (e.g., polymerase chain reaction (PCR) amplification, cloning) or chemical synthesis. Nucleic acid molecules or isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a protein or to form stable hybrids under stringent conditions with natural gene isolates. A nucleic acid molecule can include degeneracies. As used herein, nucleotide degeneracy refers to the phenomenon that one amino acid can be encoded by different nucleotide codons. Thus, the nucleotide sequence of a nucleic acid molecule that encodes a protein disclosed herein can vary due to degeneracies. It is noted that a nucleic acid molecule disclosed herein is not required to encode a protein having protein activity. A nucleic acid molecule can encode a truncated, mutated or inactive protein, for example. In addition, nucleic acid molecules disclosed herein are useful as probes and primers for the identification, isolation and/or purification of other nucleic acid molecules. If the nucleic acid molecule is an oligonucleotide, such as a probe or primer, the oligonucleotide preferably ranges from about 5 to about 50 or about 500 nucleotides, more preferably from about 10 to about 40 nucleotides, and most preferably from about 15 to about 40 nucleotides in length.

Reference to a gene includes all nucleotide sequences related to a natural (i.e. wild-type) gene, such as regulatory regions that control production of the protein encoded by that gene (such as, but not limited to, transcription, translation or post-translation control regions) as well as the coding region itself. A gene may be a naturally occurring allelic variant that includes a similar but not identical sequence to the nucleotide sequence encoding a given protein. Allelic variants have been previously described above. Genes can include or exclude one or more introns or any portions thereof or any other sequences or which are not included in the cDNA for that protein. The phrases "nucleic acid molecule" and "gene" can be used interchangeably when the nucleic acid molecule comprises a gene as described above.

Modified genes include natural genes modified by substitution, insertion, and/or deletion of single or multiple nucleotide sequences, which can occur within the coding sequence including exons of regions encoding a polypeptide, or in flanking regions, such as regulatory regions typically upstream (e.g., promoters, enhancers, and related sequences), downstream (e.g., transcriptional termination, and poly(A) signals), or internal regions (e.g., introns) that affect the transcription, translation, and/or activation of a polypeptide or regulatory molecule of interest. Activation of a polypeptide, for example, may require removal of one or more N-terminal, C-terminal, or internal polypeptide regions, and/or post-translational modification of specific amino acid residues, such as by glycosylation, amidation, etc., that may alter the targeting, degradation, catalytic activity, of an enzyme.

Preferably, a nucleic acid molecule as disclosed herein is produced using recombinant DNA technology (e.g., polymerase chain reaction (PCR) amplification, cloning, etc.) or chemical synthesis. Nucleic acid molecules include any nucleic acid molecules and homologues or variants thereof that are part of a gene described herein and/or that encode a protein described herein, including, but not limited to, natural allelic variants and modified nucleic acid molecules (homologues or variants) in which nucleotides have been inserted, deleted, substituted, and/or inverted in such a manner that such modifications provide the desired effect on protein biological activity or on the activity of the nucleic acid molecule. Allelic variants and protein homologues or variants (e.g., proteins encoded by nucleic acid homologues or variants) have been discussed in detail above.

A nucleic acid molecule homologue or variant (i.e., encoding a homologue or variant of a protein disclosed herein) can be produced using a number of methods known to those skilled in the art (see, for example, Sambrook et al.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Another method for modifying a recombinant nucleic acid molecule encoding a protein is gene shuffling (i.e., molecular breeding) (See, for example, U.S. Pat. No. 5,605,793 to Stemmer; Minshull and Stemmer; 1999, Curr. Opin. Chem. Biol. 3:284-290; Stemmer, 1994, P. N. A. S. USA 91:10747-10751). This technique can be used to efficiently introduce multiple simultaneous changes in the protein. Nucleic acid molecule homologues or variants can be selected by hybridization with a gene or polynucleotide, or by screening for the function of a protein encoded by a nucleic acid molecule (i.e., biological activity).

The minimum size of a nucleic acid molecule as disclosed herein is a size sufficient to encode a protein (including a fragment, homologue, or variant of a full-length protein) having biological activity, sufficient to encode a protein comprising at least one epitope which binds to an antibody, or sufficient to form a probe or oligonucleotide primer that is capable of forming a stable hybrid with the complementary sequence of a nucleic acid molecule encoding a natural protein (e.g., under moderate, high, or high stringency conditions). As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule as disclosed herein, in that the nucleic acid molecule can include a portion of a protein encoding sequence, a nucleotide sequence encoding a full-length protein (including a gene), including any length fragment between about 20 nucleotides and the number of nucleotides that make up the full length cDNA encoding a protein, in whole integers (e.g., 20, 21, 22, 23, 24, 25 nucleotides), or multiple genes, or portions thereof. The phrase "consisting essentially of", when used with reference to a nucleotide sequence herein, refers to a nucleotide sequence encoding a specified amino acid sequence that can be flanked by from at least one, and up to as many as about 60, additional heterologous nucleotides at each of the 5 and/or the 3' end of the nucleotide sequence encoding the specified amino acid sequence. The heterologous nucleotides are not naturally found (i.e., not found in nature, in vivo) flanking the nucleotide sequence encoding the specified amino acid sequence as it occurs in the natural gene or do not encode a protein that imparts any additional function to the protein or changes the function of the protein having the specified amino acid sequence.

A nucleic acid molecule as disclosed herein may be a recombinant nucleic acid molecule which comprises the nucleic acid molecule described above which is operatively linked to at least one expression control sequence. More particularly, a recombinant nucleic acid molecule typically comprises a recombinant vector and any one or more of the nucleic acid molecules as described herein. As used herein, a recombinant vector is an engineered (i.e., artificially produced) nucleic acid molecule that is used as a tool for manipulating a nucleotide sequence of choice and/or for introducing such a nucleotide sequence into a host cell. The recombinant vector is therefore suitable for use in cloning, sequencing, and/or otherwise manipulating the nucleotide sequence of choice, such as by expressing and/or delivering the nucleotide sequence of choice into a host cell to form a recombinant cell. Such a vector typically contains nucleotide sequences that are not naturally found adjacent to nucleotide sequence to be cloned or delivered, although the vector can also contain regulatory nucleotide sequences (e.g., promoters, untranslated regions) which are naturally found adjacent to nucleotide sequences disclosed herein or which are useful for expression of the nucleic acid molecules disclosed herein (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant host cell, although it is preferred if the vector remains separate from the genome. The entire vector can remain in place within a host cell, or under certain conditions, the plasmid DNA can be deleted, leaving behind the nucleic acid molecule disclosed herein. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector disclosed herein can contain at least one selectable marker.

A recombinant vector used in a recombinant nucleic acid molecule disclosed herein may be an expression vector. As used herein, the phrase "expression vector" is used to refer to a vector that is suitable for production of an encoded product (e.g., a protein of interest, such as an enzyme as disclosed herein). A nucleotide sequence encoding the product to be produced (e.g., the protein or homologue or variant thereof) may be inserted into a recombinant vector to produce a recombinant nucleic acid molecule. The nucleotide sequence encoding the protein to be produced is inserted into the vector in a manner that operatively links the nucleotide sequence to regulatory sequences in the vector, which enable the transcription and translation of the nucleotide sequence within the recombinant host cell. Typically, a recombinant nucleic acid molecule includes at least one nucleic acid molecule as disclosed herein operatively linked to one or more expression control sequences (e.g., transcription control sequences or translation control sequences). As used herein, the phrase "recombinant molecule" or "recombinant nucleic acid molecule" primarily refers to a nucleic acid molecule or nucleotide sequence operatively linked to a transcription control sequence, but can be used interchangeably with the phrase "nucleic acid molecule", when such nucleic acid molecule is a recombinant molecule as discussed herein. As used herein, the phrase "operatively linked" refers to linking a nucleic acid molecule to an expression control sequence in a manner such that the molecule can be expressed when transfected (i.e., transformed, transduced, transfected, conjugated or conduced) into a host cell. Transcription control sequences are sequences that control the initiation, elongation, or termination of transcription. Particularly important transcription control sequences are those that control transcription initiation, such as promoter, enhancer, operator and repressor sequences. Suitable transcription control sequences include any transcription control sequence that can function in a host cell or organism into which the recombinant nucleic acid molecule is to be introduced. Transcription control sequences may also include any combination of one or more of any of the foregoing.

Recombinant nucleic acid molecules can also contain additional regulatory sequences, such as translation regulatory sequences, origins of replication, and other regulatory sequences that are compatible with the recombinant cell. A recombinant molecule, including those that are integrated into the host cell chromosome, preferably also contains secretory signals (i.e., signal segment nucleotide sequences) to enable an expressed protein to be secreted from the cell that produces the protein. Suitable signal segments include a signal segment that is naturally associated with the protein to be expressed or any heterologous signal segment capable of directing the secretion of the protein as disclosed herein. A recombinant molecule may comprise a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

The term "transfection" is generally used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells or plants and describes an inherited change due to the acquisition of exogenous nucleic acids by the microorganism that is essentially synonymous with the term "transfection." Transfection techniques include, but are not limited to, transformation, particle bombardment, electroporation, microinjection, lipofection, adsorption, infection and protoplast fusion.

One or more recombinant molecules can be used to produce an encoded product (e.g., a protein) disclosed herein. An encoded product may be produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., filamentous fungi or yeast or mushrooms), algal, plant, insect, or animal cell that can be transfected. Host cells can be either untransfected cells or cells that are already transfected with at least one other recombinant nucleic acid molecule. Preferably the host cell is a cultured cell.

Suitable cells (e.g., a host cell or production organism) may include any microorganism (e.g., a bacterium, a protist, an alga, a fungus, or other microbe), and is preferably a bacterium, a yeast or a filamentous fungus. Suitable bacterial genera include, but are not limited to, *Escherichia, Bacillus, Lactobacillus, Pseudomonas* and *Streptomyces*. Suitable bacterial species include, but are not limited to, *Escherichia coli, Bacillus subtilis, Bacillus licheniformis, Bacillus stearothermophilus, Lactobacillus brevis, Pseudomonas aeruginosa* and *Streptomyces lividans*. Suitable genera of yeast include, but are not limited to, *Saccharomyces, Schizosaccharomyces, Candida, Hansenula, Pichia, Kluyveromyces*, and *Phaffia*. Suitable yeast species include, but are not limited to, *Saccharomyces cerevisiae, Schizosaccharomyces pombe, Candida albicans, Hansenula polymorpha, Pichia pastoris, Pichia canadensis, Kluyveromyces marxianus* and *Phaffia rhodozyma*.

Suitable fungal genera include, but are not limited to, *Chrysosporium, Thielavia, Neurospora, Aureobasidium, Filibasidizzm, Piromyces, Corynascus, Cryptococcus, Acremonium, Tolypocladium, Scytalidium, Schizophyllum, Sporotrichum, Penicillium, Gibberella, Myceliophthora, Mucor, Aspergillus, Fusarium, Humicola*, and *Trichoderma, Talaromyces, Rasamsonia* and anamorphs and teleomorphs thereof. Suitable fungal species include, but are not limited to, *Aspergillus niger, Aspergillus oryzae, Aspergillus nidulans, Aspergillus japonicus, Absidia coerulea, Rhizopus oryzae, Myceliophthora thermophila, Neurospora crassa, Neurospora intermedia, Trichoderma reesei, Trichoderma longibrachiatum, Penicillium canescens, Penicillium solitum, Penicillium funiculosum, Myceliophthora thermophila, Acremonium alabamense, Thielavia terrestris, Sporotrichum thermophile, Sporotrichum cellulophilum, Chaetonzium globosum, Corynascus heterothallicus, Talaromyces emersonii, Rasamsonia emersonii* and *Talaromyces flavus*. Preferably, a low cellulose strain is used. Preferably, the host cell is a fungal cell of strain C1 (VKM F-3500 D) or a mutant strain derived therefrom (e.g., UV13-6 (Accession No. VKM F-3632 D); NG7C-19 (Accession No. VKM F-3633 D); UV18-25 (VKM F-3631D), W1L (CBS122189), or W1L#100L (CBS122190)). Preferably, the host strain is a strain with reduced expression of protease and (hemi-) cellulase, more preferably free of protease and (hemi-) cellulase expression. Most preferred, the host strain is W1L#100.1Δpyr5ΔAlp1, also denominated as the LC strain (27). As described in U.S. Pat. No. 6,015,707 or U.S. Pat.

No. 6,573,086 a strain called C1 (Accession No. VKM F-3500 D), was isolated from samples of forest alkaline soil from Sola Lake, Far East of the Russian Federation. This strain was deposited at the All-Russian Collection of Microorganisms of Russian Academy of Sciences (VKM), Bakhurhina St. 8, Moscow, Russia, 113184 (present address Russia, 142290, Moscow Region, Pushchino, pr. Nauki, 5, IBPM), under the terms of the Budapest Treaty on the International Regulation of the Deposit of Microorganisms for the Purposes of Patent Procedure on Aug. 29, 1996, as *Chrysosporium lucknowense* Garg 27K, VKM F-3500 D (by A. P. Sinitsyn, O. N. Okunev, I. V. Solov'eva, V. M. Chernoglasov, M. A. Emalfarb, A. Ben-Bassat; "FermTech" LTD Acad. Kapitsky str. 32-2, Moscow, 117647, Russia). Various mutant strains of C1 have been produced and these strains have also been deposited at the All-Russian Collection of Microorganisms of Russian Academy of Sciences (VKM), Bakhurhina St. 8, Moscow, Russia, 113184, under the terms of the Budapest Treaty on the International Regulation of the Deposit of Microorganisms for the Purposes of Patent Procedure on Sep. 2, 1998 (by O. N. Okunev, A. P. Sinitsyn, V. M. Chemoglasov, and M. A. Emalfarb; "FermTech" LTD, Acad. Kapitsy str., 32-2, Moscow, 117647, Russia) or at the Centraal Bureau voor Schimmelcultures (CBS), Uppsalalaan 8, 3584 CT Utrecht, The Netherlands for the purposes of Patent Procedure on Dec. 5, 2007 (by Dyadic Nederland B. V., Nieuwe Kanaal 7s, 6709 PA Wageningen, Nederland). For example, Strain C1 was mutagenised by subjecting it to ultraviolet light to generate strain UV13-6 (Accession No. VKM F-3632 D; deposited with VKM on Sep. 2, 1998). This strain was subsequently further mutated with N-methyl-N'-nitro-N-nitrosoguanidine to generate strain NG7C-19 (Accession No. VKM F-3633 D; deposited with VKM on Sep. 2, 1998). This latter strain in turn was subjected to mutation by ultraviolet light, resulting in strain UV18-25 (Accession No. VKM F-3631 D; deposited with VKM on Sep. 2, 1998). This strain in turn was again subjected to mutation by ultraviolet light, resulting in strain W1L (Accession No. CBS122189; deposited with CBS Dec. 5, 2007), which was subsequently subjected to mutation by ultraviolet light, resulting in strain W1L#100L (Accession No. CBS122190; deposited with CBS Dec. 5, 2007). Strain C1 was initially classified as a *Chrysosporium lucknowense* based on morphological and growth characteristics of the microorganism, as discussed in detail in U.S. Pat. Nos. 6,015,707, 6,573,086 and patent PCT/NL2010/000045. The C1 strain was subsequently reclassified as *Myceliophthora thermophila* based on genetic tests. *C. luknowense* has also appeared in the literature as *Sporotrichum thermophile*.

Host cells can be either untransfected cells or cells that are already transfected with at least one other recombinant nucleic acid molecule. Encompassed are also any of the genetically modified cells described herein. Suitable host cells include insect cells (most particularly *Drosophila melanogaster* cells, *Spodoptera frugiperda* Sf9 and Sf21 cells and *Trichoplusia* High-Five cells), nematode cells (particularly *C. elegans* cells), avian cells, amphibian cells (particularly *Xenopus laevis* cells), reptilian cells, and mammalian cells (most particularly human, simian, canine, rodent, bovine, or sheep cells, e.g. NIH3T3, CHO (Chinese hamster ovary cell), COS, VERO, BHK, HEK, and other rodent or human cells). One or more protein(s) expressed by a nucleic acid molecule disclosed herein may be produced by culturing a cell that expresses the protein (i.e., a recombinant cell or recombinant host cell) under conditions effective to produce the protein. In some instances, the protein may be recovered, and in others, the cell may be harvested in whole, either of which can be used in a composition. Microorganisms for use as host cells (including recombinant host cells or genetically modified microorganisms) are cultured in an appropriate fermentation medium. An appropriate, or effective, fermentation medium refers to any medium in which a cell disclosed herein, including a genetically modified microorganism (described below), when cultured, is capable of expressing enzymes as disclosed herein and/or of catalyzing the production of (oxidised) xylo- and/or gluco-oligomers. The microorganisms can be cultured by any fermentation process which includes, but is not limited to, batch, fedbatch, cell recycle, and continuous fermentation. In general the fungal strains are grown in fermenters, optionally centrifuged or filtered to remove biomass, and optionally concentrated, formulated, and dried to produce an enzyme(s) or a multi-enzyme composition that is a crude fermentation product. Particularly suitable conditions for culturing filamentous fungi are described, for example, in U.S. Pat. No. 6,015,707 and U.S. Pat. No. 6,573,086, supra.

Depending on the vector and host system used for production, resultant proteins may either remain within the recombinant cell; be secreted into the culture medium; be secreted into a space between two cellular membranes; or be retained on the outer surface of a cell membrane. The phrase "recovering the protein" refers to collecting the whole culture medium containing the protein and need not imply additional steps of separation or purification. Proteins produced can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential precipitation or solubilization. Proteins are preferably retrieved, obtained, and/or used in "substantially pure" form. As used herein, "substantially pure" refers to a purity that allows for the effective use of the protein in any method according to the present invention. For a protein to be useful in any of the methods described herein or in any method utilizing enzymes of the types described herein, it is substantially free of contaminants, other proteins and/or chemicals that might interfere or that would interfere with its use in a method of the present invention (e.g., that might interfere with enzyme activity), or that at least would be undesirable for inclusion with a protein disclosed herein (including homologues and variants) when it is used in a method of the present invention (described in detail below). Preferably, a "substantially pure" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition (e.g., the protein of interest is about 80% of the protein in a solution/composition/buffer), and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99%, weight/weight of the total protein in a given composition.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of posttranslational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites), modification of nucleic acid molecules to correspond to the codon usage of the host cell, and deletion of sequences that destabilize transcripts.

A host cell as defined herein can also be a genetically modified microorganism that has been transfected with one or more nucleic acid molecules disclosed herein. As used herein, a genetically modified microorganism can include a genetically modified bacterium, alga, yeast, filamentous fungus, or other microbe. Such a genetically modified microorganism has a genome that is modified (i.e., mutated or changed) from its normal (i.e., wild-type or naturally occurring) form such that the desired result is achieved (i.e., increased or modified activity and/or production of at least one enzyme or a multi-enzyme composition for the conversion of lignocellulosic material to fermentable sugars). Genetic modification of a microorganism can be accomplished using classical strain development and/or molecular genetic techniques.

Such techniques known in the art and are generally disclosed for microorganisms, for example, in Sambrook et al., 1989, *Molecular Cloning: A Laboratory Manual*, Cold Spring Harbor Labs Press or *Molecular Cloning: A Laboratory Manual*, third edition (Sambrook and Russell, 2001), (jointly referred to herein as "Sambrook"). A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism. A genetically modified microorganism may endogenously contain and express an enzyme or a multi-enzyme composition and the genetic modification can be a genetic modification of one or more of such endogenous enzymes, whereby the modification has some effect on the amount and/or quality of enzyme mixtures produced by the organism of the microorganism (e.g., increased expression of the protein by introduction of promoters or other expression control sequences, or modification of the coding region by homologous recombination to increase the activity of the encoded protein).

A genetically modified microorganism can endogenously contain and express an enzyme for the catalysis of oxidation-reduction reactions, and the genetic modification can be an introduction of at least one exogenous nucleotide sequence (e.g., a recombinant nucleic acid molecule), wherein the exogenous nucleotide sequence encodes at least one additional enzyme useful for the catalysis of oxidation-reduction reactions and/or a protein that improves the efficiency of the target enzyme. The microorganism can also have at least one modification to a gene or genes comprising its endogenous enzyme(s) for the catalysis of oxidation-reduction reactions or an enzyme to aid in the conversion of lignocellulosic material.

The genetically modified microorganism does not necessarily endogenously (naturally) contain an enzyme for the catalysis of oxidation-reduction reactions, but is genetically modified to introduce at least one recombinant nucleic acid molecule encoding at least one enzyme or a multiplicity of enzymes for the catalysis of oxidation-reduction reactions. Such a microorganism can be used in a method of the invention, or as a production microorganism for crude fermentation products, partially purified recombinant enzymes, and/or purified recombinant enzymes, any of which can then be used in a method of the present invention.

Once the proteins (enzymes) are expressed in a host cell, a cell extract that contains the activity to test can be generated. For example, a lysate from the host cell is produced, and the supernatant containing the activity is harvested and/or the activity can be isolated from the lysate. In the case of cells that secrete enzymes into the culture medium, the culture medium containing them can be harvested, and/or the activity can be purified from the culture medium. The extracts/activities prepared in this way can be tested using assays known in the art.

The present invention is not limited to fungi and also contemplates genetically modified organisms such as algae, bacterial, and plants transformed with one or more nucleic acid molecules disclosed herein. The plants may be used for production of the enzymes, and/or as the lignocellulosic material used as a substrate in the methods of the invention. Methods to generate recombinant plants are known in the art. For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119.

The most widely utilized method for introducing an expression vector into plants is based on the natural transformation system of *Agrobacterium*. See, for example, Horsch et al., *Science* 227:1229 (1985). Descriptions of *Agrobacterium* vector systems and methods for *Agrobacterium*-mediated gene transfer are provided by numerous references, including Gruber et al., supra, Miki et al., supra, Moloney et al., *Plant Cell Reports* 8:238 (1989), and U.S. Pat. Nos. 4,940,838 and 5,464,763.

Another generally applicable method of plant transformation is microprojectile-mediated transformation, see e.g., Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992). Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant*

Cell Physiol. 23:451 (1982). Electroporation of protoplasts and whole cells and tissues have also been described. Donn et al., In Abstracts of VIIth International Congress on Plant Cell and Tissue Culture IAPTC, A2-38, p. 53 (1990); D'Halluin et al., Plant Cell 4:1495-1505 (1992) and Spencer et al., Plant Mol. Biol. 24:51-61 (1994).

Encompassed herein are genetically modified organisms that comprise at least one nucleic acid molecule encoding at least one enzyme as disclosed herein, in which the activity of the enzyme is downregulated. The downregulation may be achieved, for example, by introduction of inhibitors (chemical or biological) of the enzyme activity, by manipulating the efficiency with which those nucleic acid molecules are transcribed, the efficiency with which the resultant transcripts are translated, and the efficiency of post-translational modifications, or by "knocking out" the endogenous copy of the gene. A "knock out" of a gene refers to a molecular biological technique by which the gene in the organism is made inoperative, so that the expression of the gene is substantially reduced or eliminated. Alternatively, the activity of the enzyme may be upregulated. Also contemplated herein is downregulating activity of one or more enzymes while simultaneously upregulating activity of one or more enzymes to achieve the desired outcome.

Preferably, the genetically modified organism is a modified fungus, which is modified by having a reduction or elimination of enzymatic activities causing the formation of cellobionolactone/cellobionic acid and/or gluconolactone/gluconic acid. Enzymes causing the formation of cellobionolactone/cellobionic acid and/or gluconolactone/gluconic acid include: cellobiose dehydrogenase (CDH), but may also include: glucooligosaccharide dehydrogenase, glucose dehydrogenase, glucooligosaccharide oxidase, cellobiose oxidase, glucose oxidase and copper-dependent polysaccharide monooxygenases (or GH61 or polypeptides having cellulolytic enhancing activity). Such fungal strains that are lacking functional genes encoding enzymes causing the formation of cellobionolactone/cellobionic acid and/or gluconolactone/gluconic acid e.g., may be generated by gene deletion, gene disruption, gene silencing or mutation; or by deletion, disruption or mutation of gene expression regulatory sequences such as promoter sequences, terminator sequences, promoter activating sequences and sequences encoding transcription factors; or by random or site-directed mutation of the genes encoding the enzymes causing the formation of cellobionolactone/cellobionic acid and/or gluconolactone/gluconic acid.

Preferably the modified fungus is a modified fungus wherein the one or more genes encoding enzymes responsible for the production of one or more products selected from cellobionolactone, cellobionic acid, gluconolactone, and gluconic acid encode a cellobiose dehydrogenase (CDH) is deleted, disrupted or mutated. Preferably, the one or more genes encode an enzyme having an amino acid sequence of the cellobiose dehydrogenase (CDH) selected from a group of polypeptides having at least 90%, 95%, or 99% homology with any of the polypeptides of SEQ ID NOS: 4-6. The modified fungus may be a modified fungus wherein the gene encoding the cellobiose dehydrogenase (CDH) CDH1 (SEQ TD NO: 4), CDH2 (SEQ ID NO: 5), or CDH3 (SEQ ID NO: 6) is deleted, disrupted or mutated. Preferably, the modified fungus is a fungus wherein CDH activity is reduced from about 50% to about 100%, or at least 75%, 90%, or 95%, when measured by a ferricyanide reduction assay. Preferably the gene encoding CDH1 (SEQ ID NO:4) or encoding CDH2 (SEQ ID NO: 5) in *Myceliophthora thermophila* C1 is knocked out. More preferably, the genes encoding CDH1 and CDH2 in *Myceliophthora thermophila* C1 are both knocked out (double knock out). Fungal strains can be generated which lack functional genes encoding enzymes causing the formation of cellobionolactone, cellobionic acid, gluconolactone, or gluconic acid by any of a variety of genetic methods, such as gene deletion, gene disruption, or mutation.

A "xylo-oligomer" is defined herein as an oligomer that is produced after cleavage of the β-1,4 bond in the xylan backbone. Preferably, a xylo-oligmer is an, optionally substituted, β-(1→4)-linked xylan consisting of 2 to 50, or 2 to 30, or preferably of 2 to 15, or 2 to 10, or most preferably of 2 to 7 xylan residues. A substituted xylo-oligomer may be, but is not limited to, an arabino-, an acetyl-, a glucorono- and/or a methyglucurono-subsituted xylo-oligomer. An "oxidised xylo-oligomer" is a xylo-oligomer that is oxidised on the C1- and/or C4-carbon atom of the xylo-oligomer.

A "gluco-oligomer" is defined herein as an oligomer that is produced after cleavage of the β-1,4 bond in the cellulose backbone. Preferably, a gluco-oligmer is a β-(1→4)-linked glucan consisting of 2 to 50, or 2 to 30, or preferably of 2 to 15, or 2 to 10, or most preferably of 2 to 6 glucan residues. An "oxidised gluco-oligomer" is a gluco-oligomer that is oxidised on the C1- and/or C4-carbon atom of the gluco-oligomer.

The word "approximately" or "about" when used in association with a numerical value (approximately 10, about 10) preferably means that the value may be the given value of more or less 10% of the value.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

Detailed Description of the Invention

The present invention relates to a newly discovered enzyme activity, i.e. to oxidative cleavage of xylan by a lytic polysaccharide monooxygenase (LPMO). The inventors discovered that the LPMO shows cleavage of β-1,4 glycosyl bonds in xylan under the formation of oxidised xylo-oligomers, while it simultaneously cleaves between β-1,4 glucosyl units in cellulose forming oxidised gluco-oligomers. For this activity, the LPMO required molecular oxygen and an electron donor for its activity. Furthermore, the LPMO shows a strong synergistic effect with hydrolases such as endoglucanase I on the formation of oligomers from cellullose. The mode of action of the LPMO can be important for loosening the rigid xylan-cellulose polysaccharide matrix in plant biomass, enabling increased accessibility to the matrix from other enzymes. Such loosening may also improve cellulose hydrolysis from plant biomass.

In a first aspect, the present invention provides a method for degrading and/or modifying xylan in a xylan-comprising substrate, wherein said method comprises the step of contacting the xylan-comprising substrate with a lytic polysaccharide monooxygenase (LPMO). Preferably, the LPMO for use in the method of the invention is a LPMO of the AA9 family. Preferably, the LPMO is of the PMO1 subgroup, which has a divalent metal ion in the active site coordinated by His1 His68 and Tyr153. Furthermore, preferably the amino acids on positions 38, 126, 156 and 208 of the LPMO are cysteines. Preferably, the amino acid at position 191 is an asparagine. Preferably, the N-terminal histidine is methylated.

Preferably, the LPMO is obtainable from a fungus of the genus *Myceliophthora*. Preferably the fungus is of the species *M. thermophila*. Being "obtainable from" is to be understood herein as that the enzyme originates from the indicated organism, i.e. is naturally produced by the indicated organism as a native enzyme. More preferably, the LPMO originates from *M. thermophila* C1 fungus or derivatives thereof, such as a *M. thermophila* C1 fungus selected from Garg 27K, (Accession No. VKM F-3500D), UV13-6 (Accession No. VKM F-3632 D); NG7C-19 (Accession No. VKM F-3633 D); UV18-25 (Accession No. VKM F-3631 D); strain W1L (Accession No. CBS122189) or W1L#100L (Accession No. CBS122190), preferably a *M. thermophila* C1 (Accession No. VKM F-3500D).

Preferably, the LPMO for use in the method of the invention is an enzyme or protein as defined herein with an amino acid sequence of SEQ ID NO: 1, which is defined herein as MtLPMO9A. The amino acid sequence of MtLPMO9A including the signal sequence is defined by SEQ ID NO: 2. Also preferred for use in the method of the invention is a LPMO that comprises or consists of an amino acid sequence that is at least 50%, 60%, 70%, 80%, more preferably at least 90%, 91%, 92%, 93%, 94%, even more preferably at least 95%, 96%, 97%, 98%, or at least 99% identical to SEQ ID NO: 1. The LPMO for use in the method of the invention may be a homologue, variant or fragment of MtLPMO9A as defined herein. The LPMO for use in the method of the invention may a modified MtLPMO9A as defined herein. The homologue or variant may include related proteins from other organisms or modified forms of the given protein.

Preferably, the LPMO for use in the method of the invention is capable of oxidising a substrate with a β-1,4-linked xylan backbone, which is indicated herein as having xylan oxidizing activity. Preferably, the method of the invention is for xylan oxidation, i.e. preferably xylan degradation and/or modification of the method of the invention is xylan oxidation, preferably resulting in the production of oxidised xylo-oligomers.

Preferably, the LPMO for use in the method of the invention has at least 10%, 20%, 30%, 40%, preferably at least 50%, 60%, 70%, 80%, more preferably at least 90%, 91%, 92%, 93%, 94%, 95%, 96%, 97%, 98%, 99% or most preferably at least 100% of the xylan oxidizing activity of MtLPMO9A as assessed by a method known in the art for assessing xylan oxidizing activity, preferably by using an assay as exemplified herein. In brief, in said assay, the LPMO for which activity needs to be assessed is expressed in the protease/(hemi-) cellulase free C1-expression host (LC strain), produced under glucose limitation in a fed-batch process (pH 6.0; 32° C.), as described previously (27) resulting in a LPMO-rich crude enzyme extract from which the LPMO is purified with three successive chromatographic steps as described in SI (Supporting Information) Materials and Methods (provided herein in the Example Section) after which protein contents are analysed for all fractions obtained (SI Materials and Methods). Preferably, Regenerated amorphous cellulose (RAC) is used as substrate for assessing xylan oxidizing activity. Regenerated amorphous cellulose (RAC) is prepared from Avicel® PH-101 (Sigma-Aldrich; comprising 2% w/w xylan) by moistening Avicel (100 mg) with 0.6 mL of water, and slowly adding 10 mL of 86.2% ortho-phosphoric acid followed by rigorously stirring for 30 min until Avicel is completely dissolved. Thereafter, the dissolved cellulose is precipitated during step-wise addition of 40 mL water. By centrifugation (4000 g, 12 min at 4° C.) the pellet obtained is washed twice with water and neutralised with 2 M sodium carbonate. The pellet is washed again with water (three times) and the final pellet is suspended in water until the final dry matter content of 1.4±0.1 g per 100 g RAC suspension. Xylan oxidizing activity is assessed on this RAC by dissolving RAC (1-2 mg/mL) in 50 mM ammonium acetate buffer (pH 5.0), with addition of ascorbic acid (final concentration of 1 mM). The LPMO is added (12.5 μg/mg substrate) and incubated for 24 h at 50° C. in a head-over-tail rotator in portions of 1 mL total volume (Stuart® rotator, Bibby Scientific LTD, Stone, UK) at 20 rpm. The amount of oxidised xylo-oligomers is assessed by HPAEC and MALDI-TOF MS as described in SI Materials and Methods and compared to the amount of oxidised xylo-oligomers produced by performing the same assay with MtLPMO9A, which is expressed, produced and purified under the exact same conditions.

Preferably, the LPMO for use in the method of the invention that is an enzyme or protein that comprises or consists of an amino acid sequence that is at least 50%, 60%, 70%, 80%, more preferably at least 90%, 91%, 92%, 93%, 94%, even more preferably at least 95%, 96%, 97%, 98%, or at least 99% identical to SEQ ID NO: 1, has at least 10%, 20%, 30%, 40%, preferably at least 50%, 60%, 70%, 80%, more preferably at least 90%, 91%, 92%, 93%, 94%, 95%, 96%, 97%, 98%, 99% or most preferably at least 100% of the xylan oxidizing activity of MtLPMO9A.

The method of the invention is preferably performed under aerobic conditions. "Aerobic conditions" or "oxic conditions" are herein defined as conditions or a process run in the presence of oxygen and in which oxygen is consumed, preferably at a rate of at least 0.5, 1, 2, 5, 10, 20 or 50 mmol/L/h, and wherein organic molecules, reducing agents, and/or enzymes as indicated herein serve as electron donor and oxygen serves as electron acceptor.

Preferably, the method of the invention further comprises contacting the xylan-comprising substrate with an electron donor. Preferably, the electron donor is a reducing agent or an enzyme such as a cellobiose dehydrogenase (CDH). Encompassed within the method of the present invention is a method wherein the LPMO and the electron donor, i.e. the enzyme or reducing agent, are contacted with the xylan-comprising substrate either sequentially or simultaneously. Preferably, within the method of the invention, the LPMO and electron donor are contacted with the xylan-comprising substrate simultaneously. Also encompassed within the method of the present invention is a xylan-comprising substrate that already comprises said electron donor. The reducing agent for use as an electron donor may be selected from, but is not limited to, glutathion, ascorbate, lithium aluminum hydride ($LiAlH_4$), nascent (atomic) hydrogen, sodium amalgam, diborane, sodium borohydride ($NaBH_4$), compounds containing the $Sn^{2+}$ ion such as tin(II) chloride, sulfite compounds, hydrazine (Wolff-Kishner reduction), zinc-mercury amalgam (Zn(Hg)), diisobutylaluminum hydride (DIBAL-H), lindlar catalyst, oxalic acid ($C_2H_2O_4$), formic acid (HCOOH), ascorbic acid ($C_6H_8O_6$), phosphites, hypophosphites, and phosphorous acid, dithiothreitol (DTT), compounds containing the $Fe^{2+}$ ion such as iron(II) sulfate, carbon monoxide (CO), carbon (C), and Tris(2-carboxyethyl)phosphine HCl (TCEP). The reducing agent of a method of the invention may also be a combination of different reducing agents, preferably a combination of reducing agents as indicated herein.

The amount of electron donor for use in a method of the invention is understood to depend on the amount of LPMO present in the composition. Preferably, the amount of electron donor is sufficient in order not to be rate limiting for the LPMO oxidizing activity of the composition as defined herein. Preferably, the amount of the electron donor for use in a method of the invention is an amount that is equivalent to 0.1-20 mM, preferably equivalent to 0.1-10 mM, more preferably equivalent to 0.5-5 mM, most preferably equivalent to about 1 mM ascorbic acid ("about" is to be understood herein as being +/−10%). "Equivalent" being understood here as having comparable or similar reducing capacity.

In an embodiment, the method of the invention further comprises contacting the xylan-comprising substrate with cellulose, wherein preferably said cellulose is associated or is able to associate with xylan via hydrogen bonding, more preferably said cellulose is hemicelluloses-associated cellulose and/or amorphous cellulose, optionally regenerated amorphous cellulose (RAC). Preferably, the xylan-comprising substrate for use in a method of the invention is further contacted with said cellulose in an amount that results in the desired xylan- and/or glucan degradation and/or modification, which can be assessed using an assay as described herein. Preferably, the method of the invention comprises contacting the xylan-comprising substrate with said cellulose in case the xylan-comprising substrate of the method of the invention is free or only comprises a low amount of said cellulose. Within this embodiment, preferably said xylan-comprising substrate comprises xylan that is able to associate with said cellulose, preferably to form hydrogen bondings. Preferably, said xylan-comprising substrate comprises xylan that consists of large unsubstituted, linear xylan chains, preferably such as is present in oat spelt xylan and birchwood xylan as used in the Examples presented herein. Preferably, said xylan-comprising substrate does not consist only of, or preferably does not comprise mainly of, or even more preferably does not comprise, xylan that has arabinosyl-substituents present on the β-1,4-xylan backbone such as the branched xylan present in wheat arabinoxylan such as used in the Examples presented herein. Preferably, the xylan to be degraded and/or modified in the xylan-comprising substrate is xylan that consists of large unsubstituted, linear xylan chains, preferably such as is present in oat spelt xylan and birchwood xylan as used in the Examples presented herein. Preferably, the xylan to be degraded and/or modified in the xylan-comprising substrate is not xylan that has arabinosyl-substituents present on the β-1,4-xylan backbone such as the branched xylan present in wheat arabinoxylan as used in the Examples presented herein.

In another embodiment, the xylan-comprising substrate for use in a method of the invention comprises xylan associated with cellulose, preferably via hydrogen bonding. Preferably, said xylan-comprising substrate comprises cellulose associated with hemicellulose. Preferably, said xylan-comprising substrate comprises amorphous cellulose, optionally regenerated amorphous cellulose (RAC). In a preferred embodiment, the xylan to be degraded and/or modified in the method of the invention, and comprised within the xylan-comprising substrate as defined herein, is associated with cellulose, preferably via hydrogen-bonding. Preferably, said xylan is associated with cellulose associated with hemicellulose, and/or amorphous cellulose, optionally regenerated amorphous cellulose (RAC). Preferably, said xylan is comprised within regenerated amorphous cellulose (RAC), preferably wherein said RAC is obtainable as exemplified further herein. Preferably, said xylan-comprising substrate for use in a method of the invention comprises cellulose, xylan associated with cellulose as indicated herein, cellulose associated with hemicelluloses and/or amorphous cellulose, optionally regenerated amorphous cellulose (RAC), in an amount that results in the desired xylan- and/or glucan degradation and/or modification, which can be assessed using an assay as described herein.

Preferably, the xylan-comprising substrate for use in a method of the invention comprises or is further contacted with cellulose, cellulose associated with hemicellulose and/or amorphous cellulose, optionally regenerated amorphous cellulose (RAC) in an amount that results in the desired xylan- and/or glucan degradation and/or modification, which can be assessed using an assay as described herein.

Preferably, the xylan-comprising substrate of the method of the invention comprises or is further contacted with an electron donor and/or cellulose as defined herein.

Preferably, the method of the invention further comprises glucan degradation and/or modification. Preferably, the LPMO for use in the method of the invention oxidizes substrates with β-1,4-linked glucans in addition to substrates with a β-1,4-linked xylan backbone. Oxidizing substrates with β-1,4-linked glucans is indicated herein as having glucan oxidizing activity. Preferably, the LPMO for use in the method of the invention has at least 10%, 20%, 30%, 40%, preferably at least 50%, 60%, 70%, 80%, more preferably at least 90%, 91%, 92%, 93%, 94%, 95%, 96%, 97%, 98%, 99% or most preferably at least 100% of the glucan oxidizing activity of MtLPMO9A is assessed by using a method known in the art for assessing glucan oxidizing activity, preferably by using an assay as exemplified herein, i.e. the same assay as indicated above for assessing xylan oxidizing activity, wherein the amount of oxidixed gluco-oligomers is assessed by HPAEC and MALDI-TOF MS as described in *SI Materials and Methods* and compared to the amount of oxidised gluco-oligomers produced by performing the same assay with MtLPMO9A, which is expressed, produced and purified under the exact same conditions.

Preferably, the LPMO for use in the method of the invention that is an enzyme or protein that comprises or consists of an amino acid sequence that is at least 50%, 60%, 70%, 80%, more preferably at least 90%, 91%, 92%, 93%, 94%, even more preferably at least 95%, 96%, 97%, 98%, or at least 99% identical to SEQ ID NO: 1, has at least 10%, 20%, 30%, 40%, preferably at least 50%, 60%, 70%, 80%, more preferably at least 90%, 91%, 92%, 93%, 94%, 95%, 96%, 97%, 98%, 99% or most preferably at least 100% of the glucan oxidizing activity of MtLPMO9A.

Even more preferably, the LPMO for use in the method of the invention that is an enzyme or protein that comprises or consists of an amino acid sequence that is at least 50%, 60%, 70%, 80%, more preferably at least 90%, 91%, 92%, 93%, 94%, even more preferably at least 95%, 96%, 97%, 98%, or at least 99% identical to SEQ ID NO: 1, has at least 10%, 20%, 30%, 40%, preferably at least 50%, 60%, 70%, 80%, more preferably at least 90%, 91%, 92%, 93%, 94%, 95%, 96%, 97%, 98%, 99% or most preferably at least 100% of the xylan oxidizing activity of MtLPMO9A and at least 10%, 20%, 30%, 40%, preferably at least 50%, 60%, 70%, 80%, more preferably at least 90%, 91%, 92%, 93%, 94%, 95%, 96%, 97%, 98%, 99% or most preferably at least 100% of the glucan oxidizing activity of MtLPMO9A.

Preferably, the method of the present invention further comprises contacting the xylan-comprising substrate with one or more additional enzymes. Encompassed within the method of the present invention is a method wherein the LPMO and one or more additional enzymes are contacted with the xylan-comprising substrate either sequentially or simultaneously. In an embodiment, the LPMO and one or more additional enzymes are contacted with the xylan-comprising substrate simultaneously. In a further embodiment, the LPMO and one or more additional enzymes are contacted with the xylan-comprising substrate sequentially. Preferably, within this embodiment wherein the one or more additional enzymes are accessory enzymes and/or enzymes that are used in a pretreatment step, the one or more additional enzymes are contacted with the xylan-comprising substrate before contacting the xylan-comprising substrate to the LPMO. Also encompassed within the method of the present invention is a xylan-comprising substrate that already comprises said one or more additional enzymes.

Preferably, the xylan-comprising substrate of the method of the invention comprises or is further contacted with an electron donor and one or more additional enzymes defined herein. Preferably, the xylan-comprising substrate of the method of the invention comprises or is further contacted with one or more additional enzymes and a cellulose defined herein. Preferably, the xylan-comprising substrate of the method of the invention comprises or is further contacted with an electron donor, a cellulose and one or more additional enzymes defined herein. The inventors found a strong synergistic effect of MtLPMO9A and endoglucanase I originating from *Trichoderma viride* on the formation of oligomers form cellulose-associated hemicelluloses. Therefore, preferably, the additional enzyme or at least one of the additional enzymes is a glycosyl hydrolase as defined herein. Preferably, said glycosyl hydrolase is a cellulase as defined herein. More preferably, said cellulase is an endoglucanase as defined herein. Preferably, said endoglucanase is obtainable from a filamentous fungus from a genus selected from the group consisting of: *Chrysosporium, Thielavia, Rasamsonia, Neurospora, Aureobasidium, Filibasidium, Piromyces, Corynascus, Cryptococcus, Acremonium, Tolypocladium, Scytalidium, Schizophyllum, Sporotrichum, Penicillium, Gibberella, Myceliophthora, Mucor, Aspergillus, Fusarium, Humicola, Trichoderma, Talaromyces* and *Rasamsonia*. Preferably, said endoglucansase is endoglucanase I. Preferably, said endoglucanase I originates from *Trichoderma viride* or *Myceliophtora thermophila*, most preferably from *Myceliophtora thermophila*. Preferably, the endoglucanase for use in the method of the invention is an enzyme or protein with an amino acid sequence of SEQ ID NO: 3, which is defined herein as TvEG I. Also preferred is the use of an endoglucanase in the method of the invention, wherein said endoglucanase is an enzyme or protein comprising or consisting of an amino acid sequence that is at least 50%, 60%, 70%, 80%, more preferably at least 90%, 91%, 92%, 93%, 94%, even more preferably at least 95%, 96%, 97%, 98%, or at least 99% identical to SEQ ID NO: 3.

Preferably, the endoglucanase for use in the method of the invention is an enzyme or protein with an amino acid sequence of SEQ ID NO: 10, which is defined herein as MtEG VIII. Also preferred is the use of an endoglucanase in the method of the invention, wherein said endoglucanase is an enzyme or protein comprising or consisting of an amino acid sequence that is at least 50%, 60%, 70%, 80%, more preferably at least 90%, 91%, 92%, 93%, 94%, even more preferably at least 95%, 96%, 97%, 98%, or at least 99% identical to SEQ ID NO: 10.

Preferably, the endoglucanase for use in the method of the invention is an enzyme or protein with an amino acid sequence of SEQ ID NO: 14 (MtEG II), SEQ ID NO: 18 (MtEG I), SEQ ID NO: 22 (MtEG III), SEQ ID NO: 26 (MtEG V) or SEQ ID NO: 30 (MtEG VI). Also preferred is the use of an endoglucanase in the method of the invention, wherein said endoglucanase is an enzyme or protein comprising or consisting of an amino acid sequence that is at least 50%, 60%, 70%, 80%, more preferably at least 90%, 91%, 92%, 93%, 94%, even more preferably at least 95%, 96%, 97%, 98%, or at least 99% identical to SEQ ID NO: 14, 18, 22, 26 or 30. SEQ ID NO: 14, 18, 22, 26 and 30 are the amino acid sequences of the mature enzymes (MtEG II, MtEG I, MtEG III, MtEG V and MtEG VI, respectively). The amino acid sequences of these enzymes including the signal sequence are defined by SEQ ID NO: 13 for MtEG II, SEQ ID NO: 17 for MtEG I, SEQ ID NO: 21 for MtEG III, SEQ ID NO: 25 for MtEG V and SEQ ID NO: 19 for MtEG VI.

Preferably, the composition comprising both the LPMO and the endoglucanase as defined herein results in an increase in glucan degrading activity, preferably in cellulase degrading activity, as compared to the use of only the endoglucanase as defined herein at the same amount and/or concentration. Preferably, the glucan degrading activity is assessed by an assay known in the art, preferably by the assay as detailed herein above for assessing glucan oxidizing activity, wherein the amount of gluco-oligomers is assessed by HPAEC and MALDI-TOF MS as described in SI Materials and Methods. The amount of gluco-oligomers formed when using the combination of the LPMO and the endoglucanase for which activity is compared to the amount of gluco-oligomers produced by performing the same assay with the endoglucanase alone, under the exact same conditions, wherein preferably the amount of endoglucanase, either alone or in the composition comprising a LPMO, is 100 μg/g substrate. Preferably, the combination of the LPMO (10 mg/g substrate) and endoglucanase (100 μg/g substrate) results in an increase of at least 10%, 20%, 30%, 40%, preferably at least 50%, 60%, 70%, 80%, more preferably at least 90%, 100%, 110%, 120% or most preferably at least 130%, 140%, 150% or 160% of the gluco-oligomer production as compared to the use of the endoglucanase (100 μg/g substrate) alone.

Preferably, the method of the invention comprises degradation and/or modification of cellulose and/or cellulose associated with hemicellulose.

The "one more additional enzymes" for use in a method of the invention, may be comprised in a multi-enzyme composition. A "multi-enzyme composition" is defined herein as comprising at least a further enzyme suitable for use in a method of the invention as detailed herein below. Any combination of the proteins disclosed herein is suitable for use in the multi-enzyme compositions of a method of the present invention. It is to be understood that any of the enzymes described specifically herein can be combined with any one or more of the enzymes described herein or with any other available and suitable enzymes, to produce a multi-enzyme composition. The invention is not restricted or limited to the specific exemplary combinations listed below. One or more components of a multi-enzyme composition (other than proteins of the present invention) can be obtained from or derived from a microbial, plant, or other source or combination thereof, and will contain enzymes capable of performing oxidation-reduction reactions. Examples of enzymes included in the multi-enzyme compositions of a method of the invention include oxidases, oxygenases, monoxygenases, Baeyer-Villiger monooxygenases, dioxygenases, peroxidases, dehydrogenases, reductases that catalyze an oxidationreduction reaction.

The multi-enzyme composition may comprise enzymes for degrading a lignocellulosic and/or hemicellulosic material or a fragment thereof that has biological activity. The multi-enzyme composition may further comprise at least one cellobiohydrolase, at least one xylanase, at least one endoglucanase, at least one β-glucosidase, at least one β-xylosidase, and at least one accessory enzyme in the absence of enzymes which lead to the formation of cellobionolactone/cellobionic acid and/or gluconolactone/gluconic acid. A xylanase may be selected from the group consisting of: endoxylanases, exoxylanases, and β-xylosidases in the absence of enzymes which lead to the formation of cellobionolactone/cellobionic acid and/or gluconolactone/gluconic acid. Accessory enzymes include an enzyme selected from the group consisting of: cellulase, glucosidase, copper-dependent polysaccharide monooxygenase (or GH61 or polypeptide having cellulolytic enhancing activity), xylanase, xylosidase, ligninase, glucuronidase, arabinofuranosidase, arabinase, arabinogalactanase, ferulic acid esterase, lipase, pectinase, glucomannase, amylase, laminarinase, xyloglucanase, galactanase, galactosidase, glucoamylase, pectate lyase, chitosanase, exo-β-D-glucosaminidase, cellobiose dehydrogenase, and acetylxylan esterase in the absence of enzymes which lead to the formation of cellobionolactone/cellobionic acid and/or gluconolactone/gluconic acid. The multi-enzyme composition may further comprise at least one hemicellulase. A hemicellulase may be selected from the group consisting of a xylanase, an arabinofuranosidase, an acetyl xylan esterase, a glucuronidase, an endo-galactanase, a mannanase, an endo-arabinase, an exo-arabinase, an exo-galactanase, a ferulic acid esterase, a galactomannanase, a xyloglucanase, and mixtures thereof. A xylanase may be selected from the group consisting of endoxylanases, exoxylanases, and β-xylosidases in the absence of enzymes which lead to the formation of cellobionolactone/cellobionic acid and/or gluconolactone/gluconic acid. The multi-enzyme composition may further comprise at least one cellulase. The multi-enzyme composition may be a crude fermentation product. The multi-enzyme composition may be a crude fermentation product that has been subjected to a purification step. The multi-enzyme composition may further comprise one or more accessory enzymes. Accessory enzymes may include at least one enzyme selected from the group consisting of: cellulase, glucosidase, copper-dependent polysaccharide monooxygenase (or GH61 or polypeptide having cellulolytic enhancing activity), xylanase, xylosidase, ligninase, glucuronidase, arabinofuranosidase, arabinase, arabinogalactanase, ferulic acid esterase, lipase, pectinase, glucomannanase, amylase, laminarinase, xyloglucanase, galactanase, galactosidase, glucoamylase, pectate lyase, chitosanase, exo-β-D-glucosaminidase, cellobiose dehydrogenase, acetylxylan esterase and acetylesterase. The accessory enzyme may be added as a crude or a semi-purified enzyme mixture. In some embodiments, the accessory enzyme is produced by culturing at least one organism on a substrate to produce the enzyme. The multi-enzyme composition may further comprise at least one protein for degrading an arabinoxylan-containing material or a fragment thereof that has biological activity. The multi-enzyme composition may further comprise at least one endoxylanase, at least one β-xylosidase, and at least one arabinofuranosidase. An arabinofuranosidase may comprise an arabinofuranosidase with specificity towards single substituted xylose residues, an arabinofuranosidase with specificity towards double substituted xylose residues, or a combination thereof.

The multi-enzyme compositions of a method of the invention can also include cellulases, hemicellulases (such as xylanases, including endoxylanases, exoxylanases, and β-xylosidases; mannanases, including endomannanases, exomannanases, and β-mannosidases), ligninases, amylases, glucuronidases, proteases, esterases (including ferulic acid esterase), lipases, glucosidases (such as β-glucosidase), and xyloglucanases. While the multi-enzyme composition may contain many types of enzymes, mixtures comprising enzymes that increase or enhance sugar release from biomass are contemplated, which may include hemicellulases.

In one embodiment, the hemicellulase is selected from a xylanase, an arabinofuranosidase, an acetylxylan esterase, a glucuronidase, an endo-galactanase, a mannanase, an endo-arabinase, an exo-arabinase, an exo-galactanase, a ferulic acid esterase, a galactomannanase, a xyloglucanase, or mixtures of any of these. In particular, the enzymes can include glucoamylase, β-xylosidase and/or β-glucosidase.

Also preferred are mixtures that comprise enzymes that are capable of degrading cell walls and releasing cellular contents. The enzymes of the multi-enzyme composition can be provided by a variety of sources. In one embodiment, the enzymes can be produced by growing organisms such as bacteria, algae, fungi, and plants which produce the enzymes naturally or by virtue of being genetically modified to express the enzyme or enzymes. In another embodiment, at least one enzyme of the multi-enzyme composition is a commercially available enzyme. In some embodiments, the multi-enzyme compositions comprise an accessory enzyme. An accessory enzyme can have the same or similar function or a different function as an enzyme or enzymes in the core set of enzymes. These enzymes have been described elsewhere herein, and can generally include cellulases, xylanases, ligninases, amylases, lipidases, or glucuronidases, for example. Some accessory enzymes for example can include enzymes that when contacted with biomass in a reaction, allow for an increase in the activity of enzymes (e.g., hemicellulases) in the multi-enzyme composition. An accessory enzyme or enzyme mix may be composed of enzymes from (1) commercial suppliers; (2) cloned genes expressing enzymes; (3) complex broth (such as that resulting from growth of a microbial strain in media, wherein the strains secrete proteins and enzymes into the media); (4) cell lysates of strains grown as in (3); and, (5) plant material expressing enzymes capable of degrading lignocellulose. In some embodiments, the accessory enzyme is a glucoamylase, a pectinase, or a ligninase.

In an embodiment, the method of the invention is to obtain fermentable products, such as sugars, from degrading biomass and/or lignocellulosic material, preferably biomass rich in hemicellulose, as defined herein. Preferably, said lignocellulosic material is agro-waste or a residue produced by agriculture and forestry. The lignocellulosic material may be partially or completely degraded to fermentable sugars. Economical levels of degradation at commercially viable costs are contemplated. Due in part to the many components that comprise biomass and lignocellulosic materials, enzymes or a mixture of enzymes capable of degrading xylan, lignin, protein, and carbohydrates are needed to achieve saccharification. Preferably, the one or more additional enzymes include enzymes or compositions thereof with, for example, oxidoreductases, cellobiohydrolase, endoglucanase, β-glucosidase, xylanase and other hemicellulase activities. The xylan-comprising substrate in this embodiment preferably comprises or consists of biomass, preferably biomass rich in hemicellulose, preferably pulp, as defined herein.

Preferably, the method of the invention is to dissolve pulp for the production of chemicals such as, but not limited to, rayon, cellophane and several chemicals such as cellulose esters (acetates, nitrates, propionates and butyrates) and cellulose ethers (carboxymethyl cellulose and methyl and ethyl cellulose) and ethanol (for instance as bioethanol biofuel). Also preferred is the method of the invention for paper and pulp bleaching. The xylan-comprising substrate in this embodiment comprises or consists of paper or pulp, preferably soft and/or hardwood pulp. The method of the invention may be used to improve bleachability of pulp in the pulp and paper industry. The use of xylan degrading and/or modifying enzymes in the bleaching process is to reduce the consumption of bleaching chemicals, such as chloride containing chemicals, which leads to a reduced formation of environmentally undesired organo-chlorine compounds. Also as a direct result of the better bleachability of pulp after a xylanase treatment, it is possible to produce a product with a high final brightness where such brightness would otherwise be hard to achieve (such as totally chlorine free (TCF) bleaching using peroxide).

In a further embodiment, the invention provides a method for degrading Distillers Dried Grain (DDG), preferably, but not limited to, DDG derived from corn, to sugars. The method comprises contacting the DDG with the LPMO as defined herein. In certain embodiments, at least 10% of fermentable sugars are liberated. Preferably, at least 15% of the sugars are liberated, or at least 20% of the sugars are liberated, or at least 23% of the sugars are liberated, or at least 24% of the sugars are liberated, or at least 25% of the sugars are liberated, or at least 26% of the sugars are liberated, or at least 27% of the sugars are liberated, or at least 28% of the sugars are liberated. In this embodiment, the xylan-comprising substrate preferably comprises or consists of DDG.

Also provided are methods that comprise further contacting the lignocellulosic material with at least one accessory enzyme. Accessory enzymes have been described elsewhere herein. The accessory enzyme or enzymes may be added at the same time, prior to, or following the method of the present invention, or can be expressed (endogenously or overexpressed) in a genetically modified microorganism used in a method of the invention. When added simultaneously, the LPMO of the method of the invention will be compatible with the accessory enzymes selected. When the enzymes are added following the method of the present invention, the conditions (such as temperature and pH) may be altered to those optimal for the accessory enzyme before, during, or after addition of the accessory enzyme. Multiple rounds of enzyme addition are also encompassed. The accessory enzyme may also be present in the lignocellulosic material itself as a result of genetically modifying the plant. The nutrient medium used in a fermentation reaction can also comprise one or more accessory enzymes.

In some embodiments, the method of the invention comprises a pretreatment process. In general, a pretreatment process will result in components of the lignocellulose being more accessible for downstream applications such as digestion by enzymes. The pretreatment can be a chemical, physical or biological pretreatment. The lignocellulose may have been previously treated to release some or all of the sugars, as in the case of DDG. Physical treatments, such as grinding, boiling, freezing, milling, vacuum infiltration, and the like may also be used with the methods of the invention. In one embodiment, the heat treatment comprises heating the lignocellulosic material to 121° C. for 15 minutes. A physical treatment such as milling can allow a higher concentration of lignocellulose to be used in the methods of the invention. A higher concentration refers to about 20%, up to about 25%, up to about 30%, up to about 35%, up to about 40%, up to about 45%, or up to about 50% lignocellulose. The lignocellulose may also be contacted with a metal ion, ultraviolet light, ozone, and the like. Additional pretreatment processes are known to those skilled in the art, and can include, for example, organosolv treatment, steam explosion treatment, lime impregnation with steam explosion treatment, hydrogen peroxide treatment, hydrogen peroxide/ozone (peroxone) treatment, acid treatment, dilute acid treatment, and base treatment, including ammonia fiber explosion (AFEX) technology. Details on pretreatment technologies and processes can be found in Wyman et al., *Bioresource Tech.* 96:1959 (2005); Wyman et al., *Bioresource Tech.* 96:2026(2005); Hsu, "Pretreatment of biomass" In Handbook on Bioethanol: Production and Utilization, Wyman, Taylor and Francis Eds., p. 179-212 (1996); and Mosier et al., *Bioresource Tech.* 96:673 (2005).

In some embodiments, the methods may be performed one or more times in whole or in part. That is, one may perform one or more pretreatments, followed by one or more reactions with a composition of a method of the invention. The enzymes may be added in a single dose, or may be added in a series of small doses. Further, the entire process may be repeated one or more times as necessary. Therefore, one or more additional treatments with heat and enzymes are contemplated.

The methods described above result in the production of fermentable sugars. During, or subsequent to the method of the invention, the fermentable sugars may be recovered and/or purified by any method known in the art. The sugars can be subjected to further processing; e.g., they can also be sterilized, for example, by filtration.

In an additional embodiment, the invention provides a method for producing an organic substance, comprising saccharifying a lignocellulosic material with an effective amount of LPMO and/or one or more additional enzymes as defined herein for use of a method of the present invention, fermenting the saccharified lignocellulosic material obtained with one or more microorganisms, and recovering the organic substance from the fermentation. Sugars released from biomass can be converted to useful fermentation products including but not limited to amino acids, vitamins, pharmaceuticals, animal feed supplements, specialty chemicals, chemical feedstocks, plastics, solvents, fuels, or other organic polymers, lactic acid, and ethanol, including fuel ethanol. Specific products that may be produced by the methods of the invention include, but not limited to, bio fuels (including ethanol); lactic acid; plastics; specialty chemicals; organic acids, including citric acid, succinic acid, itaconic and maleic acid; solvents; animal feed supplements; pharmaceuticals; vitamins; amino acids, such as lysine, methionine, tryptophan, threonine, and aspartic acid; industrial enzymes, such as proteases, cellulases, amylases, glucanases, lactases, lipases, lyases, oxidoreductases, and transferases; and chemical feedstocks. The methods of the invention are also useful to generate feedstocks for fermentation by fermenting microorganisms. In one embodiment, the method further comprises the addition of at least one fermenting organism. As used herein, "fermenting organism" refers to an organism capable of fermentation, such as bacteria and fungi, including yeast. Such feedstocks have additional nutritive value above the nutritive value provided by the liberated sugars.

The one or more additional enzymes for use in a method of the present invention preferably also comprise enzyme combinations that break down or modify lignin material, reducing or preventing unwanted adsorption of other components of multi-enzyme compositions applied. Such enzyme combinations or mixtures can include a multi-enzyme composition that contains at least one protein of the host organism or one or more enzymes or other proteins from other microorganisms, plants, or similar organisms. Synergistic enzyme combinations and related methods are contemplated. The invention includes methods to identify the optimum ratios and compositions of enzymes with which to degrade each lignin and lignocellulosic material. These methods entail tests to identify the optimum enzyme composition and ratios for efficient conversion of any biomass substrate to its constituent sugars. The Examples below include assays that may be used to identify optimum ratios and compositions of enzymes with which to degrade lignocellulo sic materials.

In another embodiment, the method of the invention is for clarification and/or increasing the rate of filtration and/or decreasing haze formation of juices and/or beverages such as wine and beer. In this embodiment, the xylan-comprising substrate preferably comprises or consists of juice from fruit or vegetable such as, but not limited to, apple-, pineapple-, orange- and tomotato-, prune-, cranberry-juice, and/or cereals, such as, but not limited to barley, corn, wheat, rye, oats and maize. In this embodiment, the one or more additional enzymes for use in a method of the invention further preferably comprise pectinase, carboxymethylcellulase and/or amylase.

In a further embodiment, the method of the invention is for macerating vegetables and/or fruit. In this embodiment, the xylan-comprising substrate is a fruit and/or a vegetable. In this embodiment, the one or more additional enzymes for use in a method of the invention further preferably comprise pectinase, carboxymethylcellulase and/or amylase.

In another embodiment, the method of the invention is for extraction of coffee, plant oils, and starch.

In another embodiment, the method of the invention is used in the production of xylitol, a valuable sweetener that has applications in both the pharmaceutical and food industries.

In another embodiment, the method of the invention is for increasing digestibility and/or nutritional properties of animal feedstocks or animal food, such as, but not limited to, agricultural silage and grain feed. Preferably, the LPMO for use in a method of the invention may be present in a feed premix and/or an animal feedstock that is preferably for monogastric animals (e.g. poultry or swine). Said animal feedstock preferably contains cereals (e.g. barley, wheat, maize, rye or oats) or cereal by-products. Preferably, the xylan-comprising substrate in this embodiment comprises or consists of a cereal and/or cereal solution. The composition of the method of the invention as defined herein improves the break-down of plant cell walls which leads to better utilization of the plant nutrients by animal. This leads to improved growth rate and feed conversion. Also, the viscosity of the feeds containing xylan can be reduced. Preferably, in this embodiment, the xylan-comprising substrate comprises or consists of animal feedstock such as, but not limited to, agricultural silage and grain feed, preferably comprising cereals.

In another embodiment, the method of the invention is to increase the quality of bakery products and/or improve textual characteristics (break and shred quality and crumb quality) of the bakery products such as, but not limited to bread. Preferably, the method of the invention is applied in order to increase the volume of the bakery product, e.g. a high-rising and/or light loaf of whole meal bread. In this embodiment, the one or more additional enzymes for use in a method of the invention further preferably comprise a cellulase, such as beta-glucanase, cellulase, cellobiohydrolase and/or beta-glucosidase. Preferably, the cellulase preparation is a complex of cellulases and/or hemicellulases, preferably obtained from *Trichoderma* sp., more preferably from *T. reesei*. Also preferred are cellulase preparations obtained from *Aspergillus*, preferably obtained from *A. niger*. A suitable cellulase composition may be CELLUCLAST™ (available from Novozymes) or Bakezyme® XU, Bakezyme® XE, BakeZyme® X-cell or Bakezyme® W (all available from DSM). The one or more additional enzymes for use in a method of the invention may further comprise additional enzymes, e.g., glucoamylase, α-amylase, xylanase, protease, lipase, phospholipase may be used together with the LPMO in the dough or the composition. The additional enzyme may be of any origin, including mammalian and plant, and preferably of microbial (bacterial, yeast or fungal) origin. The glucoamylase for use in the present embodiment also include glucoamylases having a sequence identity of at least 50%, at least 60%, at least 65%, at least 70%, at least 75%, at least 80%, at least 85%, at least 90%, at least 95%, at least 96%, at least 97%, at least 98%, or at least 99% to the amino acid sequence of the *A. niger* G1 or G2 glucoamylase (Boel et al. (1984), EMBO J. 3(5), p. 1097-1102), the *A. awamori* glucoamylase disclosed in WO84/02921,or the *A. oryzae* glucoamylase (Agric. Biol. Chem. (1991), 55 (4), p. 941-949). The amylase may be fungal or bacterial, e.g. a maltogenic α-amylase from *B. stearothermophilus* or an α-amylase from *Bacillus*, e.g. *B. licheniformis* or *B. amyloliquefaciens*, a beta-amylase, e.g. from plant (e.g. soy bean) or from microbial sources (e.g. *Bacillus*), a glucoamylase, e.g. from *A. niger*, or a fungal α-amylase, e.g. from *A. oryzae*. Suitable commercial maltogenic α-amylases include NOVAMYLO (Novozymes A/S) and OPTICAKE® (Novozymes A/S). Suitable commercial fungal α-amylase compositions include, e.g., BAKEZYME P 300 (available from DSM) and FUNGAMYL 2500 SG, FUNGAMYL 4000 BG, FUNGAMYL 800 L, FUNGAMYL ULTRA BG and FUNGAMYL ULTRA SG (available from Novozymes A/S). The hemicellulase may be a pentosanase, e.g. a xylanase which may be of microbial origin, e.g. derived from a bacterium or fungus, such as a strain of *Aspergillus*, in particular of *A. aculeatus, A. niger, A. awamori*, or *A. tubigensis*, from a strain of *Trichoderma*, e.g. *T. reesei*, or from a strain of *Humicola*, e.g. *H. insolens*. Suitable commercially available xylanase preparations for use in the present invention include PENTOPAN MONO BG and PENTOPAN 500 BG (available from Novozymes), GRINDAMYL POWERBAKE (available from Danisco), and BAKEZYME BXP 5000 and BAKEZYME BXP 5001 (available from DSM). The protease may be from *Bacillus*, e.g. *B. amyloliquefaciens*. The lipase may be derived from a strain of *Thermomyces (Humicola), Rhizomucor, Candida, Aspergillus, Rhizopus*, or *Pseudomonas*, in particular from *T. lanuginosus (H. lanuginosa), Rhizomucor miehei, C. antarctica, A. niger, R. delemar, R. arrhizus* or *P. cepacia*. The phospholipase may have phospholipase A1, A2, B, C, D or lysophospholipase activity; it may or may not have lipase activity. It may be of animal origin, e.g. from pancreas, snake venom or bee venom, or it may be of microbial origin, e.g. from filamentous fungi, yeast or bacteria, such as *Aspergillus* or *Fusarium*, e.g. *A. niger, A. oryzae* or *F. oxysporum*. A preferred lipase/phospholipase from *F. oxysporum* is disclosed in WO 98/26057. Also, the variants described in WO 00/32758 may be used. The additional enzyme may be of any origin, including mammalian and plant, and preferably of microbial (bacterial, yeast or fungal) origin and may be obtained by techniques conventionally used in the art. Suitable phospholipase compositions are LIPOPAN F and LIPOPAN XTRA (available from Novozymes) or PANAMORE GOLDEN and PANAMORE SPRING (available from DSM). In this embodiment, the xylan-comprising substrate preferably comprises or consists of a baking composition or a dough, preferably comprising a flour such as whole meal flour. Whole meal flour is a flour which may be derived by grinding or mashing the whole cereal grain. When used in baking it is typically added to other more refined white flours to provide nutrients (especially fiber and protein), texture, and body to the finished product. The word "whole" refers to the fact that not only the starchy endosperm but also the bran and germ are used in making the flour.

In another embodiment, the method of the invention is used in the production of xylo-oligomers (XOs), or oxidised xylo-oligomers, which may be used in pharmaceutical, agriculture and feed products. XOs are known to have pre-biotic effects, as they are neither hydrolyzed nor absorbed in the upper gastrointestinal tract, and they affect the host by selectively stimulating the growth or activity of one or a number of bacteria in the colon, thus improving health. Furthermore, XOs are believed to reduce cholesterol levels, maintenance of gastrointestinal health, and improvement of the biological availability of calcium. Furthermore, XOs inhibit starch retrogradation, improving the nutritional and sensory properties of food. The LPMO as defined herein is highly suitable for XOs production because of the low exoxylanase and/or β-xylosidase activity. This is beneficial as exoxylanase and/or β-xylosidase activity results in production of xylose, which has inhibitory effects on XO production.

Typically, the amount of LPMO in a composition for use in a method of the invention will depend on the amount of xylan and/or glucan present in the substrate to be degraded and/or modified. In some embodiments, the amount of enzyme (herein to be understood as LPMO and/or further enzyme) may be from about 0.1 to about 200 mg enzyme or enzyme composition per gram of xylan and/or glucan; in other embodiments, from about 3 to about 20 mg enzyme or enzyme composition per gram of xylan and/or glucan. The invention encompasses the use of any suitable or sufficient amount of LPMO between about 0.1 mg and about 200 mg LPMO per gram xylan and/or glucan, in increments of 0.05 mg (i.e., 0.1 mg, 0.15 mg, 0.2 mg . . . 199.9 mg, 199.95 mg, 200 mg).

Furthermore, the amount of LPMO in a composition for use in a method of the invention may be between about 0.5 to about 1000 mg enzyme per kg dry matter of the xylan-comprising substrate, or 0.5-100 mg/kg, or 0.5-100 mg/kg or 0.5-50 mg/kg, or 1-25 mg/kg or 1-15 mg/kg, or 2-10 mg/kg enzyme/kg dry matter of the xylan-comprising substrate.

The invention also relates to methods for use in commercial processes, such as washing or treating of clothing or fabrics, detergent processes, animal feed, food, baking, beverage, biofuel, starch preparation, liquefaction, biorefining, de-inking and biobleaching of paper and pulp, oil and waste dispersing, and treatment of waste streams.

The LPMO for use in a method of the invention may be an enzyme or protein as defined herein. The LPMO for use in a method of the invention may also be a nucleic acid molecule, preferably a recombinant nucleic acid molecule and/or vector, encoding said LPMO as defined herein. In an embodiment, the LPMO for use in a method of the present invention is a part of a cell-free composition. In another embodiment, wherein the LPMO for use in a method of the invention is a nucleic acid molecule, said nucleic acid molecule is part of a host cell as defined herein, preferably a genetically modified organism as defined herein, which is preferably modified to recombinantly express the LPMO for use in a method of the invention. Preferably, the nucleic acid molecule encoding said LPMO as defined herein comprises a nucleotide sequence of encoding MtLPMO9A. Also preferred is a nucleic acid molecule that comprises a nucleotide sequence that encodes an LPMO as defined herein that has an amino acid sequence that is at least 50%, 60%, 70%, 80%, more preferably at least 90%, 91%, 92%, 93%, 94%, even more preferably at least 95%, 96%, 97%, 98%, or at least 99% identical to SEQ ID NO: 1. Preferably, said nucleic acid molecule comprises or consists of a nucleotide sequence that is at least 50%, 60%, 70%, 80%, more preferably at least 90%, 91%, 92%, 93%, 94%, even more preferably at least 95%, 96%, 97%, 98%, 99% or 100% identical to SEQ ID NO: 7, wherein SEQ ID NO: 7 represents the cDNA encoding MtLPMO9A. Preferably, said nucleic acid molecule comprises or consists of a nucleotide sequence that is at least 50%, 60%, 70%, 80%, more preferably at least 90%, 91%, 92%, 93%, 94%, even more preferably at least 95%, 96%, 97%, 98%, 99% or 100% identical to SEQ ID NO: 8, wherein SEQ ID NO: 8 represents the gDNA encoding MtLPMO9A, wherein the gDNA is to be understood as encompassing intron sequences.

Preferably, within this embodiment, the composition comprising a nucleic acid molecule encoding a LPMO further comprises one or more further nucleotide sequences encoding one or more further enzymes as defined herein, either within the same nucleic acid molecule and/or vector or on a distinct nucleic acid molecule and/or vector, as defined herein. Preferably, said further nucleotide sequence encodes a further enzyme that has the amino acid sequence of SEQ ID NO: 3 (encoding TvEG 1), SEQ ID NO: 10 (encoding MtEG VIII), SEQ ID NO: 14 (encoding MtEG 11), SEQ ID NO: 18 (encoding MtEG I), SEQ ID NO: 22 (encoding MtEG III), SEQ ID NO: 26 (encoding MtEG V) or SEQ TD NO: 30 (encoding MtEG VI). Also preferred is a further nucleotide sequence that encodes an endoglucanase as defined herein that has an amino acid sequence that is at least 50%, 60%, 70%, 80%, more preferably at least 90%, 91%, 92%, 93%, 94%, even more preferably at least 95%, 96%, 97%, 98%, or at least 99% identical to SEQ ID NO: 3, SEQ ID NO: 10, SEQ ID NO: 14, SEQ ID NO: 18, SEQ ID NO: 22, SEQ ID NO: 26 or SEQ ID NO: 30. Preferably, said further nucleotide sequence is at least 50%, 60%, 70%, 80%, more preferably at least 90%, 91%, 92%, 93%, 94%, even more preferably at least 95%, 96%, 97%, 98%, 99% or 100% identical to SEQ ID NO: 9, wherein SEQ ID NO: 9 represents the cDNA encoding TvEG I as defined herein. Preferably, said further nucleotide sequence is at least 50%, 60%, 70%, 80%, more preferably at least 90%, 91%, 92%, 93%, 94%, even more preferably at least 95%, 96%, 97%, 98%, 99% or 100% identical to SEQ ID NO: 9 (cDNA encoding TvEG I), SEQ ID NO: 11 (cDNA encoding MtEG VIII), SEQ ID NO: 15 (cDNA encoding MtEG II), SEQ ID NO: 19 (cDNA encoding MtEG I), SEQ ID NO: 23 (cDNA encoding MtEG III), SEQ ID NO: 27 (cDNA encoding MtEG V), SEQ ID NO: 31 (cDNA encoding MtEG VI). Preferably, said further nucleotide sequence is at least 50%, 60%, 70%, 80%, more preferably at least 90%, 91%, 92%, 93%, 94%, even more preferably at least 95%, 96%, 97%, 98%, 99% or 100% identical to SEQ ID NO: 12 (gDNA encoding MtEG VIII), SEQ ID NO: 16 (gDNA encoding MtEG II), SEQ ID NO: 20 (gDNA encoding MtEG I), SEQ ID NO: 24 (gDNA encoding MtEG III), SEQ ID NO: 28 (gDNA encoding MtEG V), SEQ ID NO: 32 (gDNA encoding MtEG VI).

In an embodiment, the invention provides a method for degrading and/or modifying xylan comprising cultivating a genetically modified microorganism of the present invention in a nutrient medium comprising the xylan-comprising substrate of the method of the invention.

The multi-enzyme compositions, in some embodiments, comprise microorganisms or a crude fermentation product of microorganisms. A crude fermentation product refers to the fermentation broth, which has been separated from the microorganism biomass (by filtration, for example). In general, the microorganisms are grown in fermenters, optionally centrifuged or filtered to remove biomass, and optionally concentrated, formulated, and dried to produce an enzyme(s) or a multi-enzyme composition that is a crude fermentation product. In other embodiments, enzyme(s) or multi-enzyme compositions produced by the microorganism (including a genetically modified microorganism as described below) are subjected to one or more purification steps, such as ammonium sulfate precipitation, chromatography, and/or ultrafiltration, which result in a partially purified or purified enzyme(s). If the microorganism has been genetically modified to express the enzyme(s), the enzyme(s) will include recombinant enzymes. If the genetically modified microorganism also naturally expresses the enzyme(s) or other enzymes useful for lignocellulosic saccharification or any other useful application mentioned herein, the enzyme(s) may include both naturally occurring and recombinant enzymes.

Preferably, the multi-enzyme composition for use in a method of the invention comprising at least about 500 ng, and preferably at least about 1 μg, and more preferably at least about 5 μg, and more preferably at least about 10 μg, and more preferably at least about 25 μg, and more preferably at least about 50 μg, and more preferably at least about 75 μg, and more preferably at least about 100 μg, and more preferably at least about 250 μg, and more preferably at least about 500 μg, and more preferably at least about 750 μg, and more preferably at least about 1 mg, and more preferably at least about 5 mg, of an enzyme, an (isolated) protein comprising any of the proteins or homologues, variants, or fragments thereof discussed herein. Such a multi-enzyme composition may include any carrier with which the protein is associated by virtue of the protein preparation method, a protein purification method, or a preparation of the protein for use in any method according to the present invention. For example, such a carrier can include any suitable buffer, extract, or medium that is suitable for combining with the protein of the present invention so that the protein can be used in any method described herein according to the present invention.

In one embodiment of the invention, one or more enzymes for use in a method of the invention are bound to a solid support, i.e., an immobilized enzyme. As used herein, an immobilized enzyme includes immobilized isolated enzymes, immobilized microbial cells which contain one or more enzymes of the invention, other stabilized intact cells that produce one or more enzymes of the invention, and stabilized cell/membrane homogenates. Stabilized intact cells and stabilized cell/membrane homogenates include cells and homogenates from naturally occurring microorganisms expressing the enzymes of the invention and preferably, from genetically modified microorganisms as disclosed elsewhere herein. Thus, although methods for immobilizing enzymes are discussed below, it will be appreciated that such methods are equally applicable to immobilizing microbial cells and in such an embodiment, the cells can be lysed, if desired. A variety of methods for immobilizing an enzyme are disclosed in Industrial Enzymology 2nd Ed., Godfrey, T. and West, S. Eds., Stockton Press, New York, N.Y., 1996, pp. 267-272; Immobilized Enzymes, Chibata, I. Ed., Halsted Press, New York, N.Y., 1978; Enzymes and Immobilized Cells in Biotechnology, Laskin, A. Ed., Benjamin/Cummings Publishing Co., Inc., Menlo Park, Calif., 1985; and Applied Biochemistry and Bioengineering, Vol. 4, Chibata, I. and Wingard, Jr., L. Eds, Academic Press, New York, N.Y., 1983.

In a second aspect, the invention provides a method for preparing a product from and/or comprising a xylan-comprising substrate, wherein said method comprises a method according to the first aspect, i.e. comprising at least the steps of a method of the first aspect of the invention. Encompassed within the present invention are products derivable, preferably directly derivable, from the method of the invention. Preferably, within this aspect, the xylan-comprising substrate comprises or consists of a biomass, a baking composition or dough, animal feed or a feed premix, a fruit or vegetable juice, a cereal juice, lignocellulosic material, paper or pulp, a vegetable, a fruit, a cereal and/or cereal solution. Possible products that can be formed by a method of the first aspect are indicated therein and may be, but are not limited to, oxidized XOs, oxidized GlcOs, GlcOs, fermentable sugars, organic compounds, a dough or baking composition, a bread improver, flour treatment agent, animal feed or a feed premix, a fruit-, vegetable- and/or cereal-juice, macerated fruit or vegetable, and a cereal solution. Sugars released from biomass can be converted to useful fermentation products including, but not limited to, amino acids, vitamins, pharmaceuticals, animal feed supplements, specialty chemicals, chemical feedstocks, plastics, solvents, fuels, or other organic polymers, lactic acid, and ethanol, including fuel ethanol. Specific products that may be produced by the methods of the invention include, but not limited to, biofuels (including ethanol); lactic acid; plastics; specialty chemicals; organic acids, including citric acid, succinic acid, itaconic and maleic acid; solvents; animal feed supplements; pharmaceuticals; vitamins; amino acids, such as lysine, methionine, tryptophan, threonine, and aspartic acid; xylitol; industrial enzymes, such as proteases, cellulases, amylases, glucanases, lactases, lipases, lyases, oxidoreductases, and transferases; and chemical feedstocks. The method of the invention may also be used to produce chemicals such as, but not limited to, rayon, cellophane and several chemicals such as cellulose esters (acetates, nitrates, propionates and butyrates) and cellulose ethers (carboxymethyl cellulose and methyl and ethyl cellulose and ethanol (for instance as bioethanol biofuel).

Also encompassed within the present invention are additional methods that comprise the steps of the method according to the first aspect. In some embodiments, the invention comprises, but is not limited to, additional methods comprising the method according to the first aspect, for use in diagnostic (analytical) kits; bleaching cotton; asymmetric syntheses of steroids, pharmaceuticals and other fine chemicals; biocatalysis; pollution control, and oxygenation of hydrocarbons; treatment of industrial waste waters (detoxification); soil detoxification; manufacturing of adhesives, and stimulating the immune system. Examples of such additional methods described above may also be found in the following references: *Trichoderma & Gliocladium*, Volume 2, Enzymes, biological control and commercial applications, Editors: Gary E. Harman, Christian P. Kubicek, Taylor & Francis Ltd. 1998, 393 (in particular, chapters 14, 15 and 16); Helmut Uhlig, Industrial enzymes and their applications, Translated and updated by Elfriede M. Linsmaier-Bednar, John Wiley & Sons, Inc 1998, p. 454 (in particular, chapters 5.1, 5.2, 5.3, 5.4, 5.5, 5.6, 5.7, 5.9, 5.10, 5.11, and 5.13). For saccharification applications: Hahn-Hägerdal, B., Galbe, M., Gorwa-Grauslund, M. F. Lidén, Zacchi, G. Bio-ethanol—the fuel of tomorrow from the residues of today, *Trends in Biotechnology*, 2006, 24 (12), 549-556; Mielenz, J. R. Ethanol production from biomass: technology and commercialization status, *Current Opinion in Microbiology*, 2001, 4, 324-329; Himmel, M. E., Ruth, M. F., Wyman, C. E., Cellulase for commodity products from cellulosic biomass, *Current Opinion in Biotechnology*, 1999, 10, 358-364; Sheehan, J., Himmel, M. Enzymes, energy, and the environment: a strategic perspective on the U.S. Department of Energy's Research and Development Activities for Bioethanol, *Biotechnology Progress*. 1999, 15, 817-827. For textile processing applications: Galante, Y. M., Formantici, C., Enzyme applications in detergency and in manufacturing industries, *Current Organic Chemistry*, 2003, 7, 1399-1422. For pulp and paper applications: Bajpai, P., Bajpai, P. K Deinking with enzymes: a review. *TAPPI Journal*, 1998, 81(12), 111-117; Viikari, L., Pere, J., Suurnakki, A., Oksanen, T., Buchert, J. Use of cellulases in pulp and paper applications. In: "*Carbohydrates from Trichoderma reesei and other microorganisms. Structure, Biochemistry, Genetics and Applications.*" Editors: Mark Claessens, Wim Nerinckx, and Kathleen Piens, The Royal Society of Chemistry 1998, 245-254. For food and beverage applications: Roller, S., Dea, I. C. M. Biotechnology in the production and modification of biopolymers for foods, *Critical Reviews in Biotechnology*, 1992, 12(3), 261-277. Additional references include, U.S. Pat. Nos. 5,529,926; 6,746,679; 7,732,178; 6,660,128; 6,093,436; 5,691,193; 5,785,811; 7,329,424.

In a third aspect, the invention provides a kit of parts for, or suitable for, use in a method according to the first and/or second aspect of the invention comprising or consisting of:
a) a first container containing the LPMO as defined in the first aspect of the invention; and at least one of,
b) a second container containing an electron donor; and,
c) a third container containing one or more additional enzymes as defined in the first aspect.

Also encompassed within the present invention is a kit of parts wherein comprising even further containers containing further one or more additional enzymes. Optionally, the first container containing the LPMO as defined herein, further comprises one or more additional enzymes as defined in the first aspects. The option of combinations of enzymes being in a single container depends on the compatibility of storage conditions, such as temperature and/or storage formulations, of these combinations. Multiple enzymes may be part of a single container if these enzymes have compatible storage condition requirements and if these enzymes can be admixed without losing activity as indicated herein.

In an embodiment, the first container comprises or consists of a liquid, paste or solid formulation comprising the LPMO according to the fourth aspect of the invention.

Preferably, the electron donor of the second container is a reducing agent or enzyme as defined in the first aspect of the invention. Preferably, the one or more additional enzymes of the third container are additional enzymes or is a multiple-enzyme composition as defined in the first aspect of the invention. Preferably at least one of the additional enzymes is glycosyl hydrolase, preferably an endoglucanase as defined in the first aspect.

In a preferred embodiment, the kit of parts further comprises or further consists of a fourth container comprising cellulose, preferably hemicelluloses-associated cellulose, amorphous cellulose and/or regenerated amorphous cellulose (RAC) as defined herein.

In an embodiment, the electron donor as defined herein for use in a method of the invention is present in the first, third and/or fourth container as defined herein. In a further embodiment, the cellulose as defined herein can be part of the first, second and/or fourth container as defined herein. The option of having combinations of enzymes, the electron donor and/or the cellulose as defined herein, in a single container depends on the compatibility of storage conditions of these combinations. Combinations as indicated herein may be part of a single container if the components of the combinations (i.e. enzymes, electron donor and/or cellulose), have compatible storage condition requirements and can be admixed without losing their structure and/or biological activity, such as enzymatic activity and reducing capacity.

Preferred concentrations and amounts are further detailed in the first aspect. Preferably the amounts and concentrations of the LPMO of the first container, the electron donor of the second container and optionally the one or more additional enzymes of the third container and/or the cellulose of the fourth container, are tuned to be optimal for use in a method of the invention, preferably in a single application, i.e. if the contents of all containers are admixed with a specific amount of xylan-comprising substrate as defined herein, optimal results as established by the skilled person are achieved.

In an embodiment, the contents of each of the containers of the kit of parts are administered to the xylan-comprising substrate separately. In an alternative embodiment, the content of the first and second container, and optionally the third and fourth container, stored separately, and admixed just before administration. Preferably, "just before" is to be understood herein as less than 120, 60, 30, 15, 5, 4, 3, 2 or 1 minute(s) before administration, preferably less than 5 minutes before administration. Said first, second and optionally third and fourth container may be any container, bottle, tube, ampoule, container, flask or the like, suitable for storing said the indicated contents of the containers. Preferably, the volume of any of the containers is at most 500 mL, preferably between 0.1 and 500 mL, preferably between 1 and 100 mL, more preferably of about 5, 10, 50, 20 or 100 mL.

In a fourth aspect, the invention provides a liquid, paste or solid formulation comprising the LPMO as defined herein for use, or suitable for use, in a method according to the first and/or second aspect of the invention. Preferably, the liquid, paste or solid formulation according to this aspect further comprises an electron donor, one or more additional enzymes and/or a cellulose, as defined in the first aspect. Preferably, the solid formulation is a solid formulation that has the physical appearance of a granulate or a powder. A preferred formulation is a formulation comprising or consisting of coated or uncoated granules or micro-granules. The liquid, paste or solid formulation may be formulated in accordance with methods known in the art, preferably using methods known in the art of formulating enzymes and/or multi-enzyme compositions, feedstocks, animal feedstocks, chemical feedstocks, feed premixes, food supplements, bread improvers, flour treatment agents and/or pharmaceutical products as defined herein. Preferably, the liquid, past or solid formulation according to this aspect is a multi-enzyme composition, feedstock, chemical feedstock, animal feedstock, feed premix, food supplement, bread improver, flour treatment agent and/or pharmaceutical product, wherein preferably said composition comprises one or more further compounds known in the art to be suitable for use in such composition.

The LPMO and/or one or more additional enzymes to be included in the liquid, paste or solid formulation according to this aspect may be stabilized in accordance with methods known in the art. For instance, in case the LPMO of the formulation is a protein as defined herein, by stabilizing the protein in the composition by adding an antioxidant or reducing agent to limit oxidation or the polypeptide of it may be stabilized by adding polymers such as PVP, PVA, PEG or other suitable polymers known to be beneficial to the stability of polypeptides in solid or liquid compositions. When formulating a composition comprising a LPMO and optionally further enzymes as a granulate or agglomerated powder the particles particularly have a narrow particle size distribution with more than 95% (by weight) of the particles in the range from 25 to 500 p.m. Granulates and agglomerated powders may be prepared by conventional methods, e.g. by spraying a LPMO and optionally further enzymes onto a carrier in a fluid-bed granulator. The carrier may consist of particulate cores having a suitable particle size. The carrier may be soluble or insoluble, e.g. a salt (such as NaCl or sodium sulfate), a sugar (such as sucrose or lactose), a sugar alcohol (such as sorbitol), starch, rice, corn grits, or soy. Hence the invention also provides a granule comprising a composition comprising a LPMO, and optionally further enzymes, as defined herein.

The LPMO in the formulation may be an enzyme or protein as defined herein, e.g. a crude fermentation product, or a protein preparation that has been purified or partially purified (e.g., from a microorganism) using protein purification procedures known in the art, or an enzyme, protein or peptide that can be produced synthetically (e.g., chemically, such as by peptide synthesis) or recombinantly. The LPMO in the formulation may also be a nucleic acid molecule as defined herein, e.g. a recombinant nucleic acid molecule and/or vector and/or host cell encoding said LPMO enzyme as defined herein. The LPMO comprising formulation may be a cell-free composition or a composition comprising a host cell which comprises a nucleic acid molecule encoding the LPMO as defined herein, which is preferably capable of expressing the LPMO as defined herein. The same description applies to reference to other enzymes, proteins or peptides described herein and to other microbial sources for such proteins or peptides.

In a fifth aspect, the invention provides a composition comprising a xylan-comprising substrate and a LPMO as defined in the first aspect present invention and/or a liquid, paste or solid formulation comprising a LPMO according to the fourth aspect of the present invention. Preferably, the xylan-comprising substrate is as defined in the first aspect of the invention. Preferably, the composition of this aspect is for use, or suitable for use, in a method as defined in the first aspect of the invention. Preferably, the composition comprises the LPMO in an amount or concentration suitable, or preferably optimal, for use in a method according to the first aspect. The composition may comprise an electron donor, one or more additional enzymes, and/or a cellulose, as defined in the first aspect.

In an embodiment, the composition of this aspect comprises a cellulose as defined in the first aspect, i.e. a cellulose that is interacting with hemicellulose, preferably via hydrogen-bonding. Preferably, said cellulose is cellulose associated with hemicellulose and/or amorphous cellulose, optionally regenerated amorphous cellulose (RAC). The cellulose comprised in the composition of this aspect may be a cellulose that is part of the xylan-comprising substrate of the composition of the aspect. In an alternative embodiment, the cellulose may be added in addition to the xylan-comprises, apart from optional further components as indicated herein, to result in the composition of this aspect. Preferably, a cellulose as defined herein is added to the composition of this aspect in addition and apart from the xylan-comprising substrate in case the xylan-comprising substrate of the method of the invention is free or only comprises a low amount of said cellulose. The amount of said cellulose optionally added in addition to the xylan-comprising substrate is an amount that results in the desired xylan- and/or glucan degradation and/or modification, which can be assessed using an assay as described herein.

Preferably, said one or more additional enzymes, optionally comprised within a multi-enzyme composition, are suitable (combinations) for use in a method of the invention as indicated and defined in the first aspect. Preferably, the composition of this aspect further comprises enzymes with oxidoreductases, cellobiohydrolase, endoglucanase, β-glucosidase, xylanase and other hemicellulase activities, preferably a multi-enzyme composition as defined herein.

In this aspect, the xylan-comprising substrate preferably comprises or consists of a biomass, a dough and/or baking composition, animal food, a fruit, vegetable and/or a cereal juice, lignocellulosic material, paper or pulp, a vegetable, a fruit, a cereal and/or cereal solution. Preferably, the xylan-comprising substrate comprises or consists of a biomass and/or lignocellulosic material and/or pulp and/or DDG as defined herein, preferably rich in hemicelluloses, more preferably rich in cellulose-associated hemicellulose.

In a further preferred embodiment, the xylan-comprising substrate comprises or consists of a fruit juice, a cereal juice, a beverage such as wine or beer. In this embodiment, the xylan-comprising substrate preferably comprises or consists of a (juice of) fruit and/or vegetables such as, but not limited to, apple, pineapple, orange, tomato, grape, prune and/or cranberry, and/or cereals, such as, but not limited to barley, corn, wheat, rye, oats and maize. Preferably, the composition of this aspect further comprises a pectinase, carboxymethylcellulase and/or amylase.

In a further preferred embodiment, the composition comprises a xylan-comprising substrate that comprises or consists of fruit or vegetable. Preferably, within this embodiment, the composition further comprises a pectinase, carboxymethylcellulase and/or amylase.

In a further preferred embodiment, the xylan-comprising substrate comprises or consists of an animal feedstock. Preferably, said animal feedstock comprises at least a cereal as defined herein. Said animal feedstock may be, but is not limited to, fodder including hay, straw, silage, compressed and pelleted feeds, oils and mixed rations, sprouted grains, legumes and feed grains such as, but not limited to, maize, soybean and cereal, wheat, oats, barley, and rice.

In a further preferred embodiment, the xylan-comprising substrate comprises or consists of a feed supplement composition, preferably a livestock feed supplement composition or feed premixes. Preferably, the (livestock) feed supplement composition or feed premix generally contains required vitamins, minerals and optionally chemical preservatives, antibiotics, fermentation products and/or further nutrients for the livestock. Preferably, the livestock feed supplement composition consists of dried grains, selected nutritional supplements and a moisture laden component such as condensed distillers solubles, corn steep liquor, or the like. In a particularly preferred embodiment, the livestock feed supplement composition includes from about 25% to about 65% (by weight) of dried grains; from about 5% to about 45% (by weight) of a premixed base of selected nutritional supplements; and from about 20% to about 45% (by weight) of condensed distillers solubles. In this embodiment, the mixture has a moisture content selected to give a highly palatable urea-free mixture having a granular, formable consistency with a total moisture content of about 18% to about 30%. Preferably, the dried grains are provided in the form of fermented dried grains, and more preferably in the form of fermented distiller's solubles. Optionally, the livestock feed supplement composition can be provided in the form of fermented moist grains which comprise about 50% to about 70% (by weight) of the product, the moisture content of which is about 20% to about 40%, and a premixed base of selected nutritional supplements.

In another embodiment, the xylan-comprising substrate comprises or consists of a baking composition and/or a dough. Preferably said baking composition or dough at least comprises flour. Preferably, the baking composition and/or dough comprise whole meal flour. Whole meal flour may be derived from grinding of cereal grains and is defined as flour comprising the components of the starchy endosperm, germ and bran in substantially the same relative proportions as they exist in the intact cereal grains. The production of whole meal flour may include temporary separation of the grains constituents for later recombination. Preferably the dough comprises at least 90%, at least 80%, at least 70%, at least 60%, at least 50%, at least 40%, at least 30% percent whole meal flour as determined in % of total amount of flour. Accordingly, a whole meal bread comprises at least 90%, at least 80%, at least 70%, at least 60%, at least 50%, at least 40%, at least 30% percent whole meal flour as determined in % of total amount of flour. The whole meal flour may be derived from any cereal grain, including wheat, barley, rye, oat, corn, sorghum, rice and millet. In a preferred embodiment the whole meal flour is derived from wheat. In such a preferred embodiment the dough comprises at least 90%, at least 80%, at least 70%, at least 60%, at least 50%, at least 40%, at least 30% percent whole wheat flour as determined in % of total amount of flour. Accordingly, a whole wheat bread is a bread that comprises at least 90%, at least 80%, at least 70%, at least 60%, at least 50%, at least 40%, at least 30% percent whole meal flour as determined in % of total amount of flour. In addition the dough may comprise types of refined flour or starch such as wheat flour, corn flour, corn starch, rye flour, oat flour, soy flour, sorghum flour, potato meal, potato flour or potato starch. The dough of the invention may be fresh, frozen or par-baked. The dough of the invention is normally a leavened dough or a dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae*. The dough may also comprise other conventional dough ingredients, e.g.: proteins, such as milk powder, gluten, and soy; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate. The dough may comprise fat (triglyceride) such as granulated fat or shortening, but the invention is equally applicable to a dough where less than 1% by weight of fat (triglyceride) is added, and particularly to a dough which is made without addition of fat. The dough may further comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin.

In a sixth aspect, the invention provides the use of a LPMO as defined herein, a kit of parts according to the third aspect, past or solid formulation according to the fourth aspect, and/or a composition according to the fifth aspect of the invention, in xylan degradation and/or modification, preferably in a method according to the first and/or second aspect of the invention. Preferably, the LPMO is as defined in the first aspect. Preferably, the LPMO is for use in the non-limiting list of degrading cellulose-associated hemicelluloses, obtaining fermentable products, obtaining a biofuel, dissolving and/or bleaching pulp, degrading DDG, clarification and/or increasing the rate of filtration and/or decreasing haze formation of juices and/or beverages such as wine and beer, macerating fruit, extracting coffee, plant oils and starch, increasing digestibility and/or nutritional properties of animal feedstocks, increasing the quality of bakery products and/or improving textual characteristics (break and shred quality and crumb quality) of the bakery products, and/or producing xylo-oligomers and/or gluco-oligomers, preferably oxidised xylo-oligomers and/or oxidised gluco-oligomers. Furthermore, the LPMO of the invention is for use in a multi-enzyme composition, preferably a multi-enzyme composition indicated herein as suitable for use in a method of the invention, a feed premix, a bread improver, a flour treatment agent, a pharmaceutical composition and/or a food supplement, as defined herein.

Further Aspect:

Provided is a method for degrading and/or modifying xylan in a xylan-comprising substrate, wherein said method comprises the step of contacting the xylan-comprising substrate with a lytic polysaccharide monooxygenase (LPMO) of family AA9, wherein the LPMO may be obtainable from *Myceliophthora*, preferably from *Myceliophthora thermophila* C1. The LPMO may be an enzyme that comprises or consists of an amino acid sequence that is at least 70% identical to SEQ ID NO: 1. The xylan-comprising substrate may comprise, or is further contacted with, an electron donor and/or cellulose. The method may further comprise glucan degradation and/or modification. The xylan-comprising substrate may comprise or may further be contacted with one or more additional enzymes, wherein preferably at least one of the additional enzymes is a glycosyl hydrolase, preferably an endoglucanase. The method may comprise degradation and/or modification of cellulose and/or cellulose associated with hemicellulose.

The invention also relates to a method for preparing a product from a xylan-comprising substrate, wherein said method comprises degrading and/or modifying xylan in a xylan-comprising substrate as defined herein above, and wherein the xylan-comprising substrate may comprise or consist of a biomass, a baking composition or dough, animal feed or a feed premix, a fruit or vegetable juice, a cereal juice, lignocellulosic material, paper or pulp, a vegetable, a fruit, a cereal and/or cereal solution.

Also provided is a kit of parts for use in a method for degrading and/or modifying xylan in a xylan-comprising substrate as defined herein above, wherein said kit comprises:
(i) a first container containing the LPMO as defined above; and at least one of,
(ii) a second container containing an electron donor; and,
(iii) a third container containing one or more additional enzymes, wherein said at least one of additional enzymes may be a glycosyl hydrolase, preferably an endoglucanase.

Also provided is a liquid, paste or solid formulation for use in a method for degrading and/or modifying xylan in a xylan-comprising substrate as defined herein above, wherein said formulation comprises the LPMO as defined above, preferably further comprising an electron donor and/or one or more additional enzymes, wherein preferably said at least one of the one or more additional enzymes is a glycosyl hydrolase, preferably an endoglucanase. The liquid, paste or solid formulation may be a granulate or a powder.

Also provided is a composition comprising a xylan-comprising substrate and the LPMO as defined above, and/or a liquid, paste or solid formulation as defined above. The xylan-comprising substrate may at least comprise a flour, and said composition may be baking composition. The xylan-comprising substrate may further at least comprise cellulose-associated hemicellulose, and said composition may be a biomass or lignocellulosic material. The xylan-comprising substrate may also at least comprises a cereal, and said composition may be feed or feed premix.

Also provided is a use of a LPMO, a kit of parts, a liquid, paste or solid formulation, and/or a composition as defined above, in a method for degrading and/or modifying xylan in a xylan-comprising substrate as defined above.

BRIEF DESCRIPTION OF THE DRAWINGS

FIG. 9: HPAEC elution pattern of wheat arabinoxylan (WAX), birchwood (BiWX) and oat spelt xylan (OSX) (2 mg/mL) before and after incubation with MtLPMO9A (12.5 mg/g substrate). Samples were incubated in a 50 mM ammonium acetate buffer (pH 5.0) for 24 h at 52° C. either with ascorbic acid addition (1 mM) or without. A—WAX, BiWX and OSX before and after incubation with MtLPMO9A and ascorbic acid addition (1 mM). Incubation with MtLPMO9A results in the formation of non-oxidized linear XOS, single substituted (black arrow) and multiple substituted (black dashed arrow). B—D—WAX, BiWX and OSX after incubation with MtLPMO9A in the presence or absence of regenerated amorphous cellulose (RAC; 2 mg/mL). C—D—In the presence of ascorbic acid, next to non-oxidized GlcOS and XOS, numerous products, which are not present if MtLPMO9A is incubated with xylan substrates or RAC only, are determined. Masses were further analysed by MALDI-TOF MS (FIG. 4).

REFERENCE LIST

Figure 1:
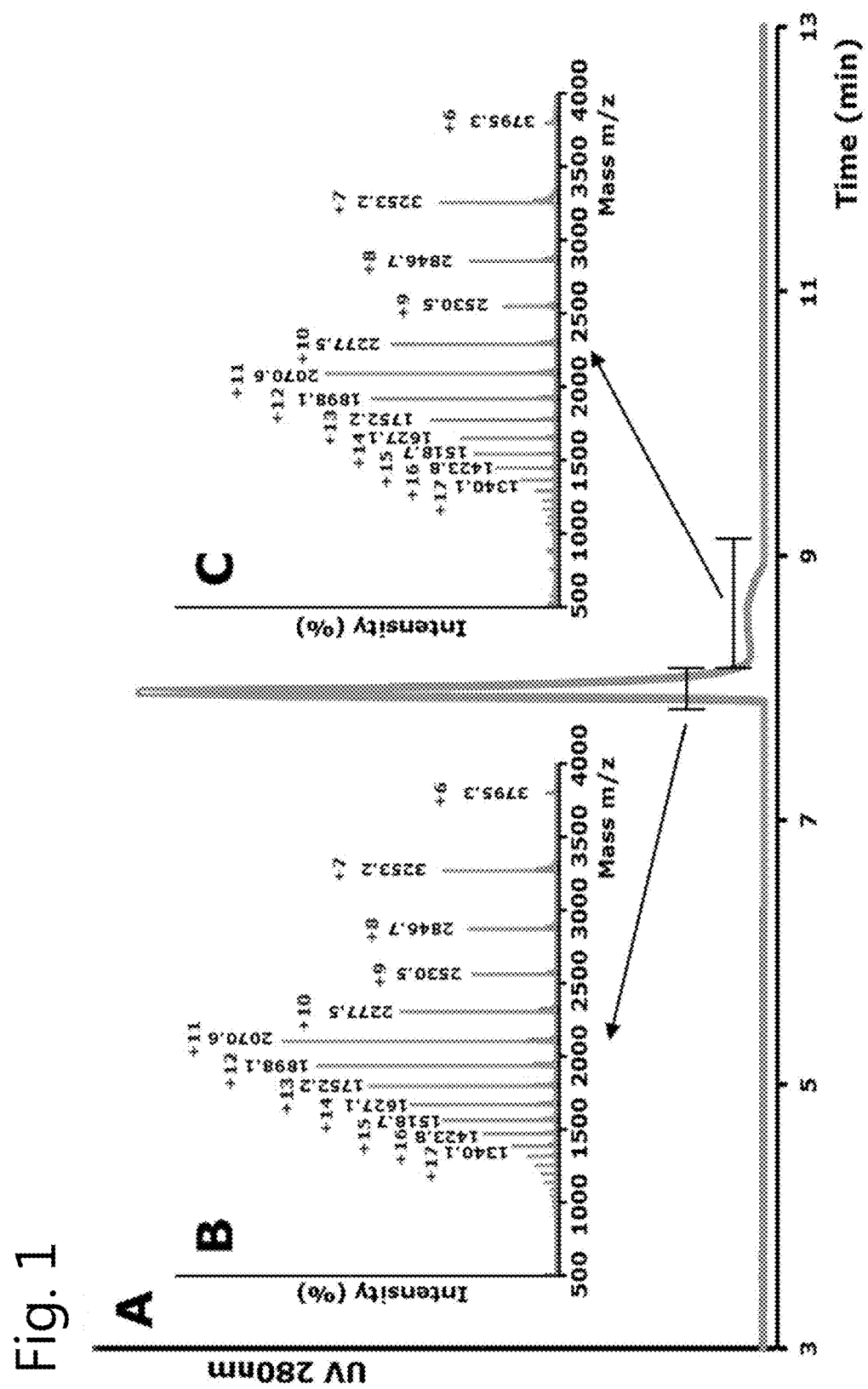
FIG. 1: Purified MtLPMO9A analyzed by LC/UV/ESI-MS using an ACQUITY UPLC separation system and a SYNAPT ion mobility mass spectrometer. A—Chromatographic profile of purified MtLPMO9A (UV 280 nm). B and C—ESI MS spectra of the main peak (B) and a shoulder (C) observed by UV. The main peak and shoulder showed identical mass spectra corresponding to the same protein with an m/z of 22765 Da. The two main peaks together featured about 99.5% of the total area measured in the UV trace at 214 nm and 94.7% of the total area measured in the total ion current (TIC) mass chromatogram (See Materials and Methods). Blue—Different charge states of MtLPMO9A.

1. Lynd L R (1996) Overview and evaluation of fuel ethanol from cellulosic biomass: Technology, Economics, the Environment, and Policy. Annual Review of Energy and the Environment 21(1):403-465.
2. Hinz S W A, et al. (2009) Hemicellulase production in *Chrysosporium lucknowense* C1. Special section: Enzymes in grain processing. Journal of Cereal Science 50(3):318-323.
3. Vincken J P, de Keizer A, Bcldman G, & Voragen A G J (1995) Fractionation of xyloglucan fragments and their interaction with cellulose. Plant Physiology 108(4):1579-1585.
4. Lam T B T, Kadoya K, & Iiyama K (2001) Bonding of hydroxycinnamic acids to lignin: ferulic and p-coumaric acids are predominantly linked at the benzyl position of lignin, not the β-position, in grass cell walls. Phytochemistry 57(6):987-992.
5. Kabel M A, van den Borne H, Vincken J-P, Voragen A G J, & Schols H A (2007) Structural differences of xylans affect their interaction with cellulose. Carbohydrate Polymers 69(1):94-105.
6. Ebringerová A, Hromádková Z, & Heinze T (2005) Hemicellulose. Advance in Polymer Science 186:1-67.
7. Yang B & Wyman C E (2004) Effect of xylan and lignin removal by batch and flowthrough pretreatment on the enzymatic digestibility of corn stover cellulose. Biotechnology and Bioengineering 86(1):88-95.
8. Jcoh T, et al. (2007) Cellulase digestibility of pretreated biomass is limited by cellulose accessibility. Biotechnology and Bioengineering 98(1):112-122.
9. CAZy (2014) Glycoside Hydrolase family classification. (www.cazy.org).
10. Levasseur A, Drula E, Lombard V, Coutinho P M, & Henrissat B (2013) Expansion of the enzymatic repertoire of the CAZy database to integrate auxiliary redox enzymes. Biotechnology for Biofuels 6:41.
11. Vu V V, Beeson W T, Phillips C M, Cate J H, & Marletta M A (2014) Determinants of regioselective hydroxylation in the fungal polysaccharide monooxygenases. Journal of the American Chemical Society 136(2):562-565.
12. Isaksen T, et al. (2014) A C4-oxidizing lytic polysaccharide monooxygenase cleaving both cellulose and cello-oligosaccharides. The Journal of Biological Chemistry 289(5):2632-2642.
13. Agger J W, et al. (2014) Discovery of LPMO activity on hemicelluloses shows the importance of oxidative processes in plant cell wall degradation. Proceedings of the National Academy of Sciences of the United States of America 111(17):6287-6292.
14. Forsberg Z, et al. (2014) Comparative study of two chitin-active and two cellulose-active AA10-type lytic polysaccharide monooxygenases. Biochemistry 53(10): 1647-1656.
15. Vu V V, Beeson W T, Span E A, Farquhar E R, & Marietta M A (2014) A family of starch-active polysaccharide monooxygenases. Proceedings of the National Academy of Sciences of the United States of America 111(38):13822-13827.
16. Westereng B, et al. (2011) The putative endoglucanase PcGH61D from *Phanerochaete chrysosporium* is a metal-dependent oxidative enzyme that cleaves cellulose. PloS one 6(11):e27807.
17. Harris P V, et al. (2010) Stimulation of lignocellulosic biomass hydrolysis by proteins of glycoside hydrolase family 61: structure and function of a large, enigmatic family. Biochemistry 49(15):3305-3316.
18. Hemsworth G R, Davies G J, & Walton P H (2013) Recent insights into copper-containing lytic polysaccharide mono-oxygenases. Current Opinion in Structural Biology 23(5):660-668.
19. Phillips C M, Beeson W T, Cate J H, & Marietta M A (2011) Cellobiose dehydrogenase and a copper-dependent polysaccharide monooxygenase potentiate cellulose degradation by *Neurospora crassa*. ACS Chemical Biology 6(12):1399-1406.
20. Beeson W T, Phillips C M, Cate J H, & Marietta M A (2012) Oxidative cleavage of cellulose by fungal copper-dependent polysaccharide monooxygenases. Journal of the American Chemical Society 134(2):890-892.
21. Kim S, Stahlberg J, Sandgren M, Paton R S, & Beckham G T (2014) Quantum mechanical calculations suggest that lytic polysaccharide monooxygenases use a copper-oxyl, oxygen-rebound mechanism. Proceedings of the National Academy of Sciences of the United States of America 111(1):149-154.
22. Guillotin S E, Van Kampen J, Boulenguer P, Schols H A, & Voragen A G J (2006) Degree of blockiness of amide groups as indicator for difference in physical behavior of amidated pectins. Biopolymers 82(1):29-37.
23. Van Gool M P (2012) Targeted discovery and functional characterisation of complex-xylan degrading enzymes. Wageningen University, Wageningen, The Netherlands.
24. Beldman G, Voragen A G J, Rombouts F M, Searle-van Leeuwen M F, & Pilnik W (1987) Adsorption and kinetic behavior of purified endoglucanases and exoglucanases from *Trichoderma viride*. Biotechnology and Bioengineering 30(2):251-257.
25. Vincken J-P, Beldman G, & Voragen A G J (1997) Substrate specificity of endoglucanases: what determines xyloglucanase activity? Carbohydrate Research 298(4): 299-310.
26. Van Gool M P, et al. (2011) Screening for distinct xylan degrading enzymes in complex shake flask fermentation supernatants. Bioresource Technology 102(10):6039-6047.
27. Visser H, et al. (2011) Development of a mature fungal technology and production platform for industrial enzymes based on a *Myceliophthora thermophila* isolate, previously known as *Chrysosporium lucknowense* C1. Ind. Biotechnol. 7:214-223.
28. Punt P, J, et al. (2010) WO/2010/107303.
29. Zhang Y H P, Cui J, Lynd L R, & Kuang L R (2006) A transition from cellulose swelling to cellulose dissolution by o-phosphoric acid: Evidence from enzymatic hydrolysis and supramolecular structure. Biomacromolecules 7(2):644-648.
30. Sali A (1995) Comparative protein modeling by satisfaction of spatial restraints. Molecular Medicine Today 1(6):270-277.
31. Eswar N, et al. (2007) Comparative protein structure modeling using MODELLER. Current Protocols in Protein Science. Chapter 2:Unit 2 9.

The invention is further explained in the following examples. These examples do not limit the scope of the invention, but merely serve to clarify the invention.

EXAMPLES

Materials and Methods

Enzyme expression, production and purification. MtLPMO9A from *Myceliophthora thermophila* C1 (SEQ ID NO: 1 represents MtLPMO9A without signal sequence; SEQ ID NO: 2 represents MtLPMO9A with signal sequence) was over-expressed in a protease/(hemi-)cellulase reduced C1-expression host (LC strain) (27, 28). Enzyme production was performed under glucose limitation in a fed-batch process (pH 6.0; 32° C.), as described previously (27) and resulted in an MtLPMO9A-rich crude enzyme extract. The MtLPMO9A was purified with three successive chromatographic steps as described in *SI Materials and Methods*. Protein contents were analysed for all fractions obtained (*SI Materials and Methods*). The confirmation of the sequence and purity of MtLPMO9A was established with LC/MS of tryptic-digests, SDS-PAGE gel electrophoresis, and UPLC-Synapt MS as described in *SI Materials and Methods*.

Substrates incubated with MtLPMO9A. Oat spelt xylan, birchwood xylan, Avicer® PH-101, xylo-oligomers (DP1-5) and gluco-oligomers (DP1-5) were obtained from Sigma-Aldrich. Wheat arabinoxylan (medium viscosity), β-glucan from barley (medium viscosity) and β-glucan from oat spelt (medium viscosity) and galactomannan (guar, medium viscosity) were purchased from Megazyme (Bray, Ireland). Xyloglucan (XG; from tamarind seed) was obtained from Dainippon Sumitomo Pharma (Osaka, Japan). Regenerated amorphous cellulose (RAC) was prepared from Avicel by adapting a method described elsewhere (29). Briefly, Avicel (100 mg) was moistened with 0.6 mL of water, and 10 mL of 86.2% ortho-phosphoric acid was slowly added followed by rigorously stirring for 30 min until Avicel was completely dissolved. The dissolved cellulose precipitated during stepwise addition of 40 mL water. By centrifugation (4000 g, 12 min at 4° C.) the pellet obtained was washed twice with water and neutralised with 2 M sodium carbonate. The pellet was washed again with water (three times) and the final pellet was suspended in water until the final dry matter content of 1.4±0.1 g per 100 g RAC suspension.

MtLPMO9A activity assays. Substrates (1-2 mg/mL, see figure-captions), were dissolved in 50 mM ammonium acetate buffer (pH 5.0), with or without addition of ascorbic acid (final concentration of 1 mM). MtLPMO9A was added (12.5 µg/mg substrate) and incubated for 24 h at 50° C. in a head-over-tail rotator in portions of 1 mL total volume (Stuart® rotator, Bibby Scientific LTD, Stone, UK) at 20 rpm. Products were analysed by HPAEC and MALDI-TOF MS as described in *SI Materials and Methods*.

Structural modelling. An alignment was made of the amino acid sequence of MtLPMO9A and the amino acid sequence of PMO1 from *Thielavia terrestris*, which scored highest in a Blast search using the MtLPMO9A sequence against the Protein Data Bank (75% amino acid identity). Using this alignment and the available structure of TtPMO1 (PDB-id: 3eii) as template, structural models were obtained for MtLPMO9A using the Modeller program version 9.14 (30). Thirty comparative models were generated, after which the model with lowest corresponding DOPE score (31) was selected for image generation using Pymol (Pymol, The PyMOL Molecular Graphics System, Version 1.5.0.4 Schrödinger, LLC, NY, USA).

Results

Enzyme Purification. From the *Myceliophthora thermophila* C1 genome, protein MtLPMO9A was predicted to be a LPMO belonging to the family AA9 (10). Addition of LPMOs to a cellulase cocktail is known to considerably increase the release of glucose from cellulose (16, 17). The present inventors now expressed and producedMtLPMO9A in a protease/(hemi-) cellulase-free *Myceliophthora thermophila* C1 strain (27, 28) with Dyadic technology (27; Dyadic N L, Wageningen, The Netherlands). MtLPMO9A was purified to apparent homogeneity using multiple chromatographic separation steps (see Materials and Methods for details). The purified enzyme showed a single band in SDS-PAGE with an apparent molecular mass of 23±1 kDa (FIG. 6), which is in good agreement with the predicted mass of MtLPMO9A (22.7 kDa; without signal peptide).

To further analyse mass and purity of MtLPMO9A, the enzyme was subjected to LC/UV/ESI mass spectrometry. The elution pattern (FIG. 1) showed one main peak comprising ±99.5% of the total protein based on UV (214 nm) and 94.7% of the total content based on total ion current (TIC) in the full mass range. MS-analysis of the peak resulted in a mass (m/z) of 22765.3±0.1 Da. In conclusion, MtLPMO9A was obtained in an extremely pure form and suitable to use for the analysis of its mode-of-action towards various polysaccharides.

Figure 2:
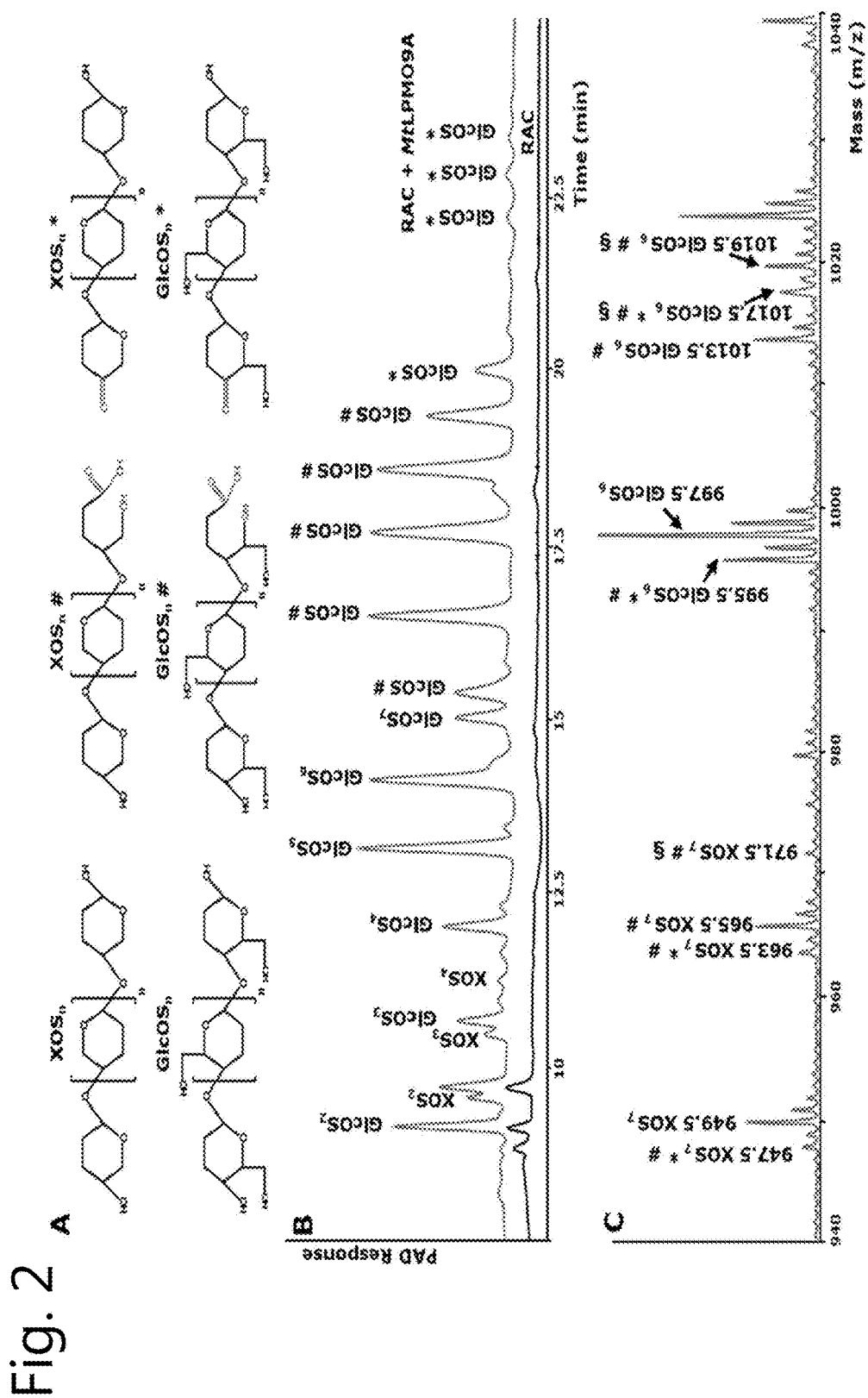
FIG. 2: A—Structure and nomenclature used throughout this report: XOSn and GlcOSn, non-oxidized xylo- and gluco-oligomers; XOSn# and GlcOSn#, xylo- and gluco-oligomers oxidized at the C1-carbon atom; XOSn* and GlcOSn*, xylo—and gluco-oligomers oxidized at the C4-cabon atom. B—HPAEC elution patterns of regenerated amorphous cellulose (RAC) before and after incubation with MtLPMO9A (5 mg/g substrate). Samples were incubated in a 50 mM ammonium acetate buffer (pH 5.0) for 24 h at 52° C. with ascorbic acid addition (1 mM). In the presence of ascorbic acid, oxidized GlcOS are formed by MtLPMO9A (marked either with # or *), of which the masses were further analyzed by MALDI-TOF MS. Using RAC as a substrate, small amounts of XOS are detected by HPAEC. C—MALDI-TOF mass spectrum of RAC incubated with MtLPMO9A with ascorbic acid. Clusters of oxidized GlcOS are determined as their lithium (Li) adducts. The insert shows masses of XOS and GlcOS oxidized either at C4 leading to a keto-group (*−2 Da) or C1 leading to a lactone (#−2 Da). The δ-lactones are instable in water and hydrolyse to the corresponding aldonic acids (#+16 Da). Double Li-adducts (one Li-adduct and one additional Li exchanged for H on the acid-group) are C1 oxidized products (§).
Figure 7:
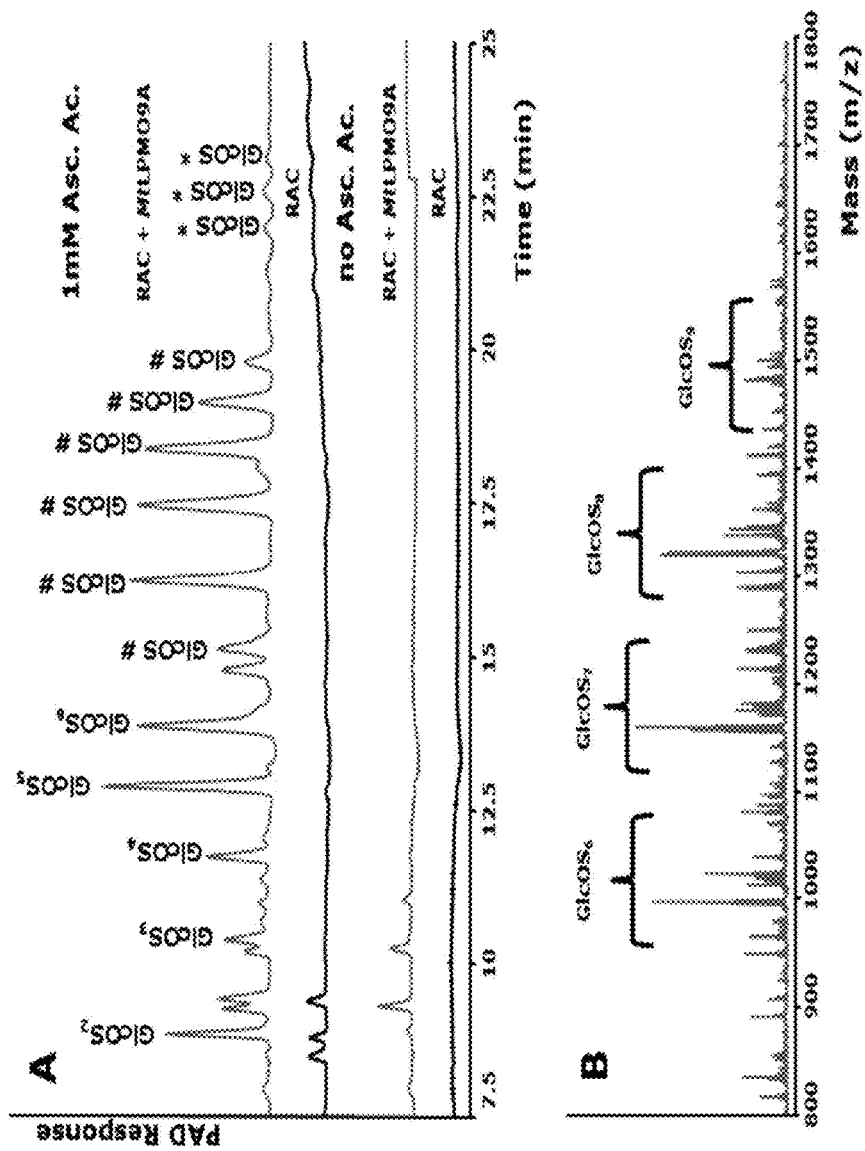
FIG. 7: A—HPAEC elution patterns of regenerated amorphous cellulose (RAC; 2 mg/mL) before and after incubation with MtLPMO9A (12.5 mg/g substrate). Samples where incubated in a 50 mM ammonium acetate buffer (pH=5) for 24 h at 52° C., either with ascorbic acid addition (1 mM) or without. In the presence of ascorbic acid, oxidized GlcOS are formed by MtLPMO9A from RAC (marked either with # or *). B—MALDI-TOF mass spectrum of RAC incubated with MtLPMO9A with ascorbic acid. Clusters of oxidized GlcOS are determined as their lithium (Li) adducts. See FIG. 3 for more details.

Activity of MtLPMO9A on amorphous cellulose. The activity of MtLPMO9A was assayed on regenerated amorphous cellulose (RAC), in the absence and presence of the external electron donor ascorbic acid. From HPAEC and MALDI-TOF MS analysis (FIG. 2) it can be concluded that in the presence of ascorbic acid, RAC is degraded by MtLPMO9A and that both C1 and C4 oxidized glucooligomers (GlcOS) and non-oxidized GlcOS are formed. Furthermore, in the absence of ascorbic acid no oxidized and non-oxidized oligomers are found, which indicates that hydrolytic activity towards RAC is absent (FIG. 7A). The identification by HPAEC of oxidized GlcOS was performed using the published elution pattern of C1- and C4-oxidized GlcOS formed by NCU01050 or NCU08760 from *Neurospora crassa* (11, 19). In addition, the formation of oxidized GlcOS was confirmed by the masses identified with MALDI-TOF MS, based on previously proposed LPMO cleaving mechanisms (19-21). In short, oxidation at C1 of the pyranose ring leads to formation of an unstable δ-lactone, which in the presence of water hydrolyses to an aldonic acid. Lactone formation results in a 2 Da lower mass compared to the non-oxidized substrate, while aldonic acid formation results in a 16 Da higher mass (FIGS. 2B and C, marked with #). Some of these acid groups may exchange an H-ion for a Li-ion, leading to a double Li-adduct corresponding to an additional mass of 6 Da (FIG. 2C, marked with §). Such double adducts have also been described for galacturonic acid oligomers in MALDI-TOF MS (22). Similarly, oxidation at the C4 position leads to a 4-ketoaldose, which is rather stable (FIG. 2C, marked with *) and corresponds like the lactone to a 2 Da lower mass compared to the non-oxidized GlcOS (12, 20).

Besides oxidized GlcOS, masses of oxidized xylo-oligomers (XOS) are observed (FIG. 2), although Avicel is known to contain only around 2% (w/w) of xylan based on the amount of xylosyl residues determined in Avicel (23). This striking observation suggests that MtLPMO9A is capable of oxidatively cleaving xylan next to cellulose.

Figure 8:
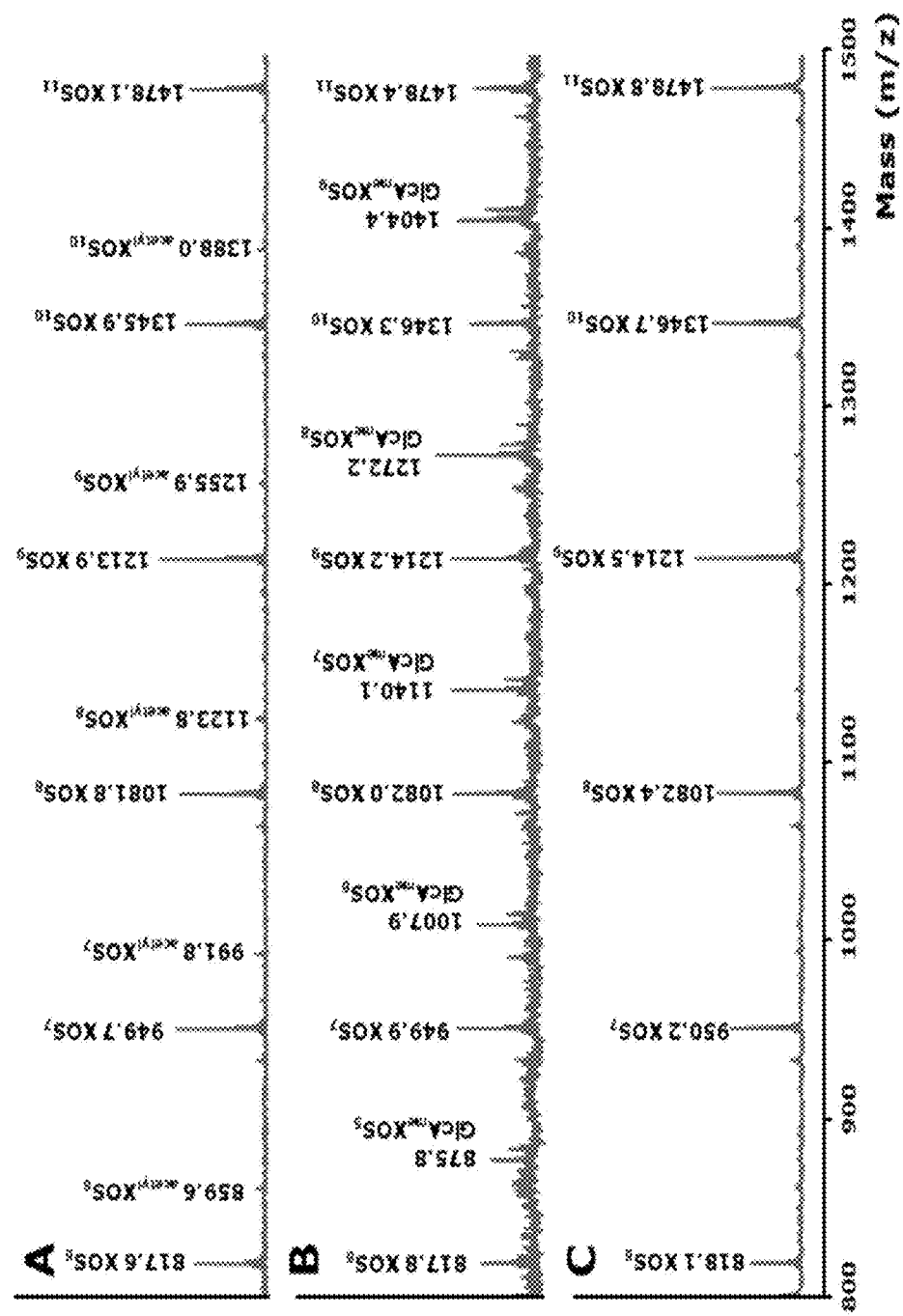
FIG. 8: MALDI-TOF MS analysis of wheat arabinoxylan (WAX; A), birchwood (BiWX; B), and oat spelt (OSX; C) xylan (2 mg/mL), after incubation of MtLPMO9A (12.5 mg/g substrate). Samples were incubated in a 50 mM ammonium acetate buffer (pH 5.0) for 24 h at 52° C. with ascorbic acid addition (1 mM). In all three incubations, MtLPMO9A released linear XOS. A—incubation of WAX with MtLPMO9A; formation of linear XOS and traces of acetylated XOS (+42 m/z). B—incubation of BiWX with MtLPMO9A; formation of linear XOS and XOS substituted with 4-O-methyl-glucoronic acid (+191 m/z). C—incubation of OSX with MtLPMO9A releases linear XOS only. Masses represents lithium adducts only.

Activity of MtLPMO9A on three types of xylans. The observation that MtLPMO9A generates oxidized XOS from RAC next to oxidized GlcOS is new and such an action of LPMOs has not been described for other LPMOs. Therefore, wheat arabinoxylan (WAX), birchwood glucuronoxylan (BiWX) and rather linear oat spelt xylan (OSX) were incubated with MtLPMO9A in the absence or presence of 1 mM ascorbic acid. The products formed were determined by using HPAEC and MALDI-TOF MS (FIGS. 8-9). Surprisingly, both in the absence and presence of ascorbic acid, no oxidized XOS were observed. However, non-oxidized XOS were released on all tested substrates, most likely pointing at the presence of a minor xylanase impurity of the MtLPMO9A fraction.

Figure 3:
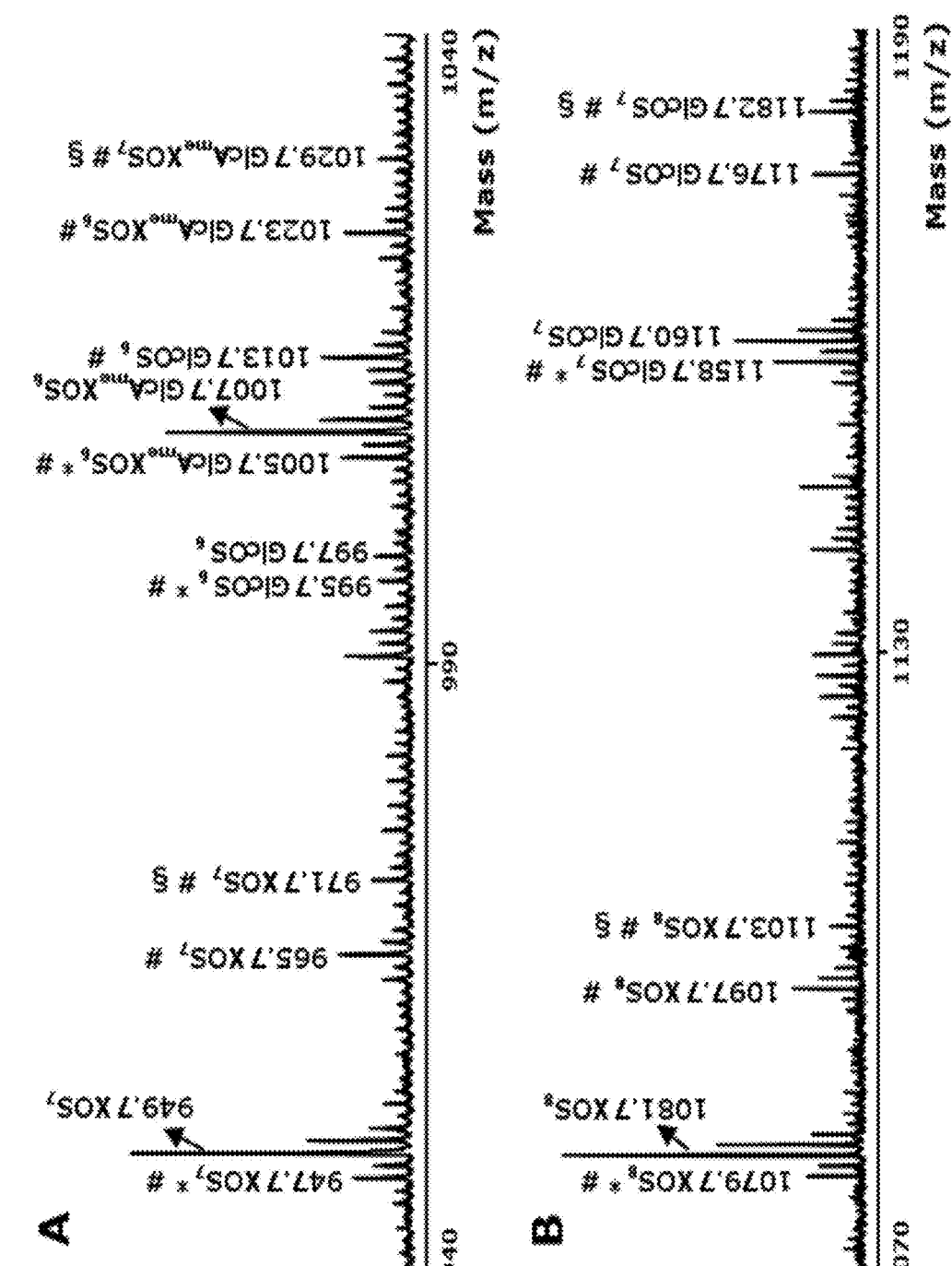
FIG. 3: MALDI-TOF MS analysis of birchwood xylan (BiWX; A; 2 mg/mL) and oat spelt xylan (OSX; B; 2 mg/mL) in the presence of regenerated amorphous cellulose (RAC; 2 mg/mL) after incubation of MtLPMO9A (10 mg/g substrate) with ascorbic acid addition (1 mM). MtLPMO9A incubation of BiWX and OSX with RAC addition releases non-oxidized and oxidized XOS and GlcOS (*, #). Figures A and B shows the presence of C4-oxidized XOS (*), and XOS oxidized at C1 to an aldonic acid (#+16 Da). Non-oxidized GlcOS and oxidized GlcOS are less detectable due to abundance of XOS present. From BiWX also 4-O-methylglucoronic acid containing non-oxidized XOS (GlcAmeXOS) and oxidized XOS containing one 4-O-methylglucuronic acid (GlcAmeXOS *, #) are formed. Masses represent lithium-adducts only. Double Li-adducts are determined for C1 oxidized products (§+6 Da). MALDI-TOF MS analysis of BiWX and OSX in the presence of RAC after incubation of MtLPMO9A without ascorbic acid does not release detectable amounts of oxidized products (data not shown).

Activity of MtLPMO9A on xylan together with RAC. Since MtLPMO9A generates oxidized XOS from RAC next to oxidized GlcOS, but not if xylan as substrate is used alone, the mode-of-action of MtLPMO9A on xylan and xylan-rich cellulosic plant biomass was further investigated. Hereto, RAC was mixed with wheat arabinoxylan (WAX), birchwood glucuronoxylan (BiWX) or oat spelt xylan (OSX). MtLPMO9A was added in the absence and presence of 1 mM ascorbic acid. The products were determined using HPAEC and MALDI-TOF MS (FIGS. 3, 9). In the presence of ascorbic acid, the OSX-RAC- and BiWX-RAC-combinations incubated with MtLPMO9A showed formation of oxidized XOS and oxidized GlcAme-XOS (4-O-methylglucuronic acid attached to XOS) as well as oxidized GlcOS (FIG. 3). In addition, non-oxidized XOS were also observed, most likely pointing at the presence of a minor xylanase impurity. MALDI-TOF MS confirmed the formation of XOS oxidized at C4 (*−2 Da) and at C1 (#+16 Da). From the WAX-RAC-combination no oxidized XOS were observed in the presence of ascorbic acid.

Figure 4:
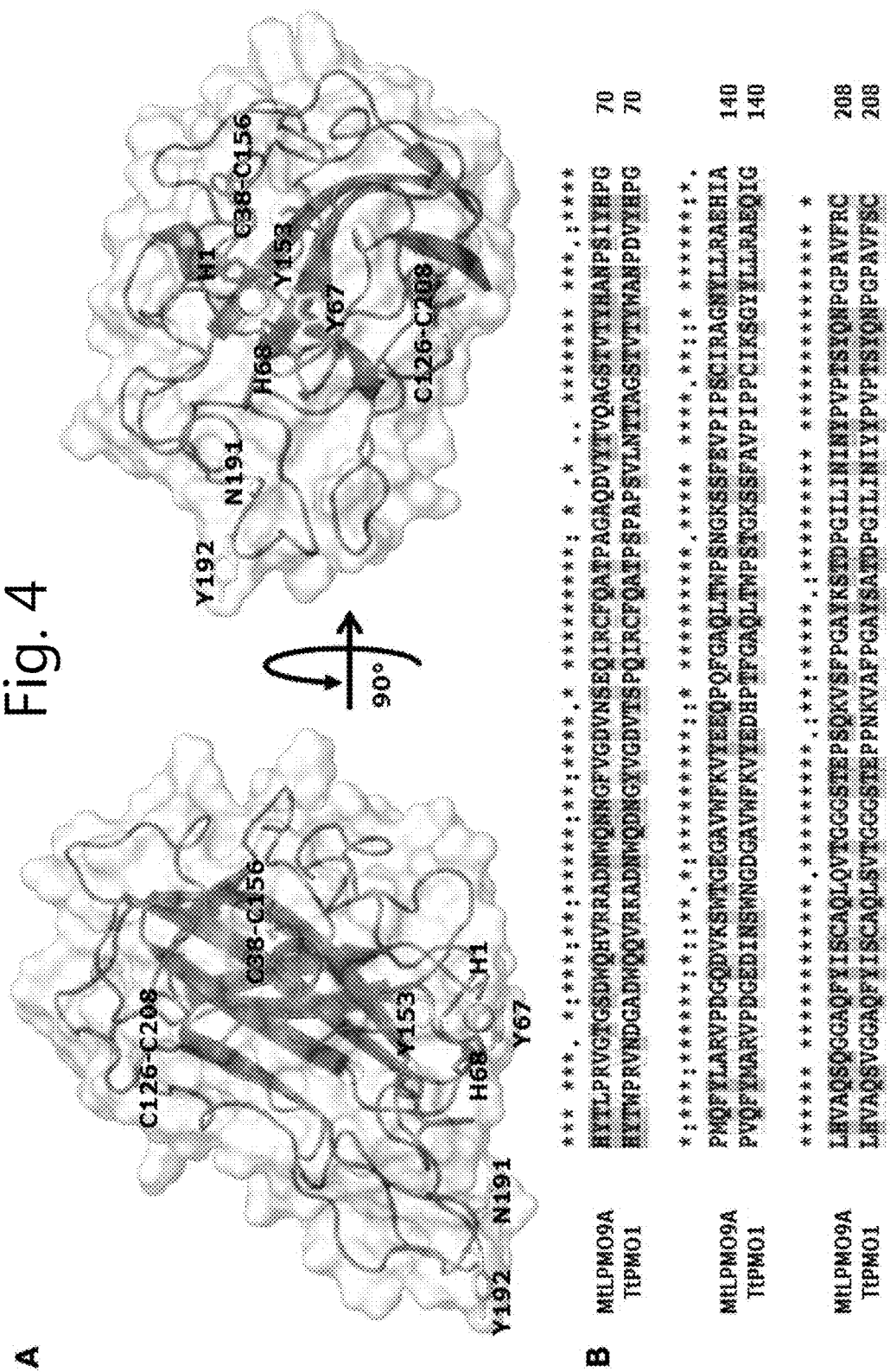
FIG. 4: A-Structural model of MtLPMO9A generated using the available template structure of PMO1 from *Thielavia terrestris* (PDB-id: 3eii) (17). The divalent metal ion (orange) in the flat face is coordinated by two histidines (His1 and His68; blue) and one tyrosine (Tyr153, magenta), which is typical for LPMOs belonging to family AA9 of the CAZy database (18). Compared to TtPMO1, Tyr191 is replaced by Asn191 in the flat face. Two disulfide bridges Cys126-Cys208 and Cys38-Cys156 are conserved and expected to be crucial for the thermo-tolerance of MtLPMO9A. B—Sequence alignment of MtLPMO9A and TtPMO1 (PDB-id: 3eii), which scored the highest in a Blast search using the MtLPMO9A sequence against the Protein Data Bank (75% amino acid identity).

Structural model of MtLPMO9A. A structural model of MtLPMO9A was generated based on the available structure of a PMO1 from *Thielavia terrestris* (17) (Protein Data Bank entry: 3eii). MtLPMO9A and TtPMO1 share 75% amino acid sequence identity. The MtLPMO9A model (FIG. 4) shows a highly conserved β-sheet core, whereas the loops differ from the reported TtPMO1 structure. The conserved disulfide bridges Cys126-Cys208 and Cys38-Cys156 are expected to be crucial for the thermo-tolerance of MtLPMO9A. The divalent metal ion in the active site is coordinated by His1, His68 and Tyr153, which is typical for the PMO1 subgroup of the AA9 family (18). Of the amino acids proposed to form the flat area of the TtPMO1 substrate-binding site, only one tyrosine is replaced by an asparagine in MtLPMO9A (Asn191). This tyrosine is also not conserved in other LPMO structures available in the Protein Data Bank. Based on the structural model of MtLPMO9A and comparing the predicted mass (amino acid sequence without signal peptide) with the actual mass determined by ESI-MS, MtLPMO9A is expected to contain a methylated N-terminal histidine.

Figure 5:
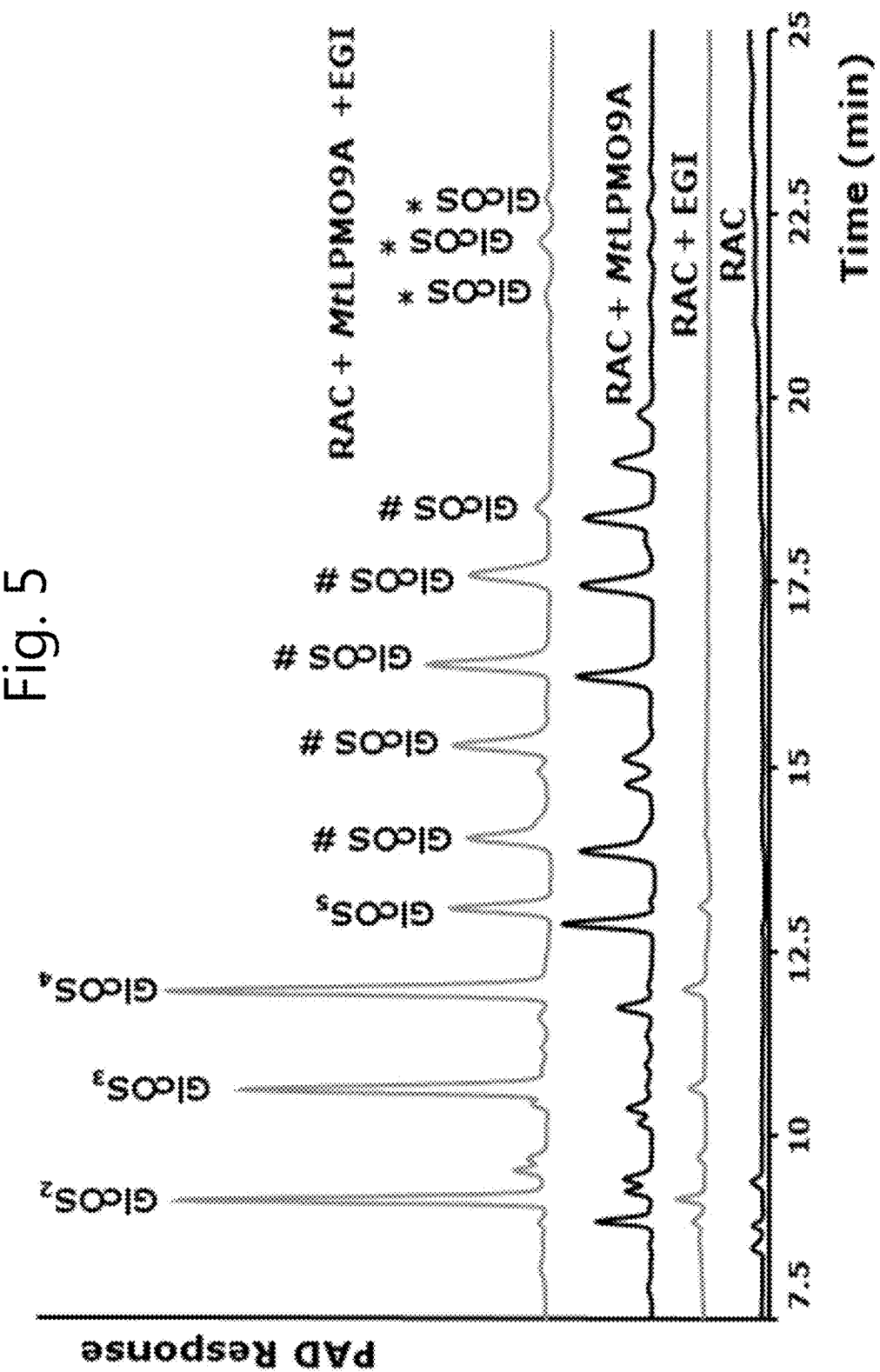
FIG. 5: HPAEC elution patterns of regenerated amorphous cellulose (RAC, 2 mg/mL) before and after incubation with MtLPMO9A (10 mg/g substrate) and endoglucanase I from *T. viride* (TvEG I, indicated as EGI) (100 µg/g substrate). Samples were incubated in a 50 mM ammonium acetate buffer (pH 5.0) for 24 h at 52° C. with ascorbic acid addition (1 mM). In the presence of ascorbic acid, mainly oxidized GlcOS are formed by MtLPMO9A from RAC (marked either with # for C1 or * for C4 oxidation). Addition of TvEG I to RAC results in hardly detectable GlcOS (DP2-5). TvEG I combined with MtLPMO9A addition results in a 16-fold higher release of GlcOS (based on comparison of the AUC of GlcOS2-4 determined by HPAEC) from RAC compared to TvEG 1 incubated with RAC only.

Synergy with EG I. The synergy of MtLPMO9A with a pure TvEG I (SEQ ID NO: 3) (24, 25) in degrading RAC is shown in FIG. 5. The release of GlcOS by TvEG I in the presence of MtLPMO9A is around 16 times higher (based on the total HPAEC-area of GlcOS$_{2-4}$) compared to the activity of pure TvEG I. The observed strong synergy of a LPMO with a hydrolase acting on cellulose has not been reported before.

Discussion

LPMOs constitute a new class of oxidative enzymes, which are expected to play a crucial role in the degradation of chitin and lignocellulosic biomass. LPMOs are known to oxidize β-(1→4)-glucosyl bonds in cellulose, chitin, β-(1→4)-linked substituted and non-substituted glucosyl units of hemicellulose and α-(1→4)-glucosyl units in starch (12-15). We purified a new LPMO from the commercially applied fungus Myceliophthora thermophila C1 and investigated its degradation capacity on a wide range of substrates (Table 1). We show for the first time that in the presence of the electron donor ascorbic acid a LPMO is able to oxidize substrates with a β-(1→4)-linked xylan backbone in addition to β-(1→4)-linked glucans.

In addition to RAC, (oxidized) XOS and (oxidized) GlcOS formation on three types of xylan, either in the absence or in combination with RAC, were investigated. The formation of oxidized XOS by MtLPMO9A was found in case RAC was present. We considered the idea that formation of glycyl radical intermediates of RAC by MtLPMO9A (19, 20) might have oxidized the xylan backbone. However, MtLPMO9A also forms oxidized XOS from RAC alone (FIG. 2C), which has not been reported for any other LPMO. Hence, we hypothesise that MtLPMO9A uses the cellulose to bind while oxidizing neighbouring xylan-chains. This idea is strengthened by the observation that the addition of RAC is essential for the formation of oxidized XOS by MtLPMO9A incubated with BiWX and OSX, while oxidized XOS are not formed if WAX is added to RAC. BiWX is a linear beta-1,4-xylan mainly substituted with 4-O-methylglucuronic acid and OSX is a linear beta-1,4-xylan with a rather low amount of substituents. Unlike WAX, both these xylans consist of large unsubstituted xylan chains, which may lead to self-association explaining their rather low solubility in water (Table 1). The low amount of substitution or a block-wise distribution of substituents (3, 5) could lead to a strong association with cellulose via hydrogen-bonding. WAX, however, is completely water soluble due to the amount and distribution of arabinosyl-substituents present on the beta-1,4-xylan backbone (26). It has been described that linear xylans, like OSX and BiWX, associate better with cellulose fibrils and are therefore closer to the neighbouring cellulose-chains, compared to more branched xylans like WAX (5).

Figure 10:
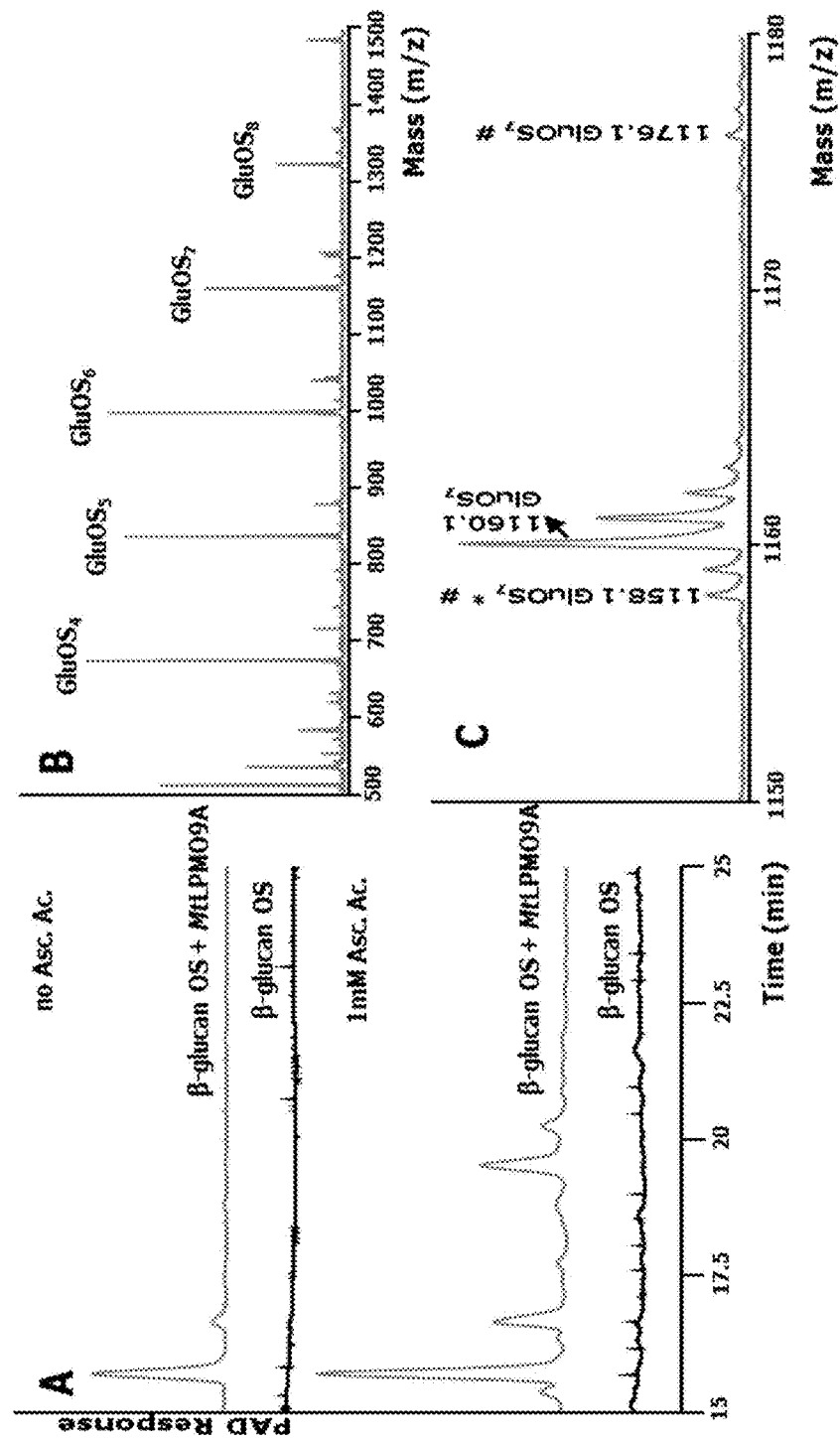
FIG. 10: HPAEC elution pattern of oat spelt β-glucan before and after incubation with partially purified MtLPMO9A (12.5 mg/g substrate), with addition of 1 mM ascorbic acid or without (0 mM). A—In the presence of ascorbic acid, oxidized products are formed by MtLPMO9A. B—MALDI-TOF mass spectrum of partially purified MtLPMO9A incubated with oat spelt β-glucan in the presence of 1 mM ascorbic acid. Clusters of oxidized GlcOS are determined and the insert (C) shows the presence of GlcOS oxidized at C1 with an aldonic acid (#) and at C4 with a keto-group (*). Masses represent lithium-adducts only.
Figure 11:
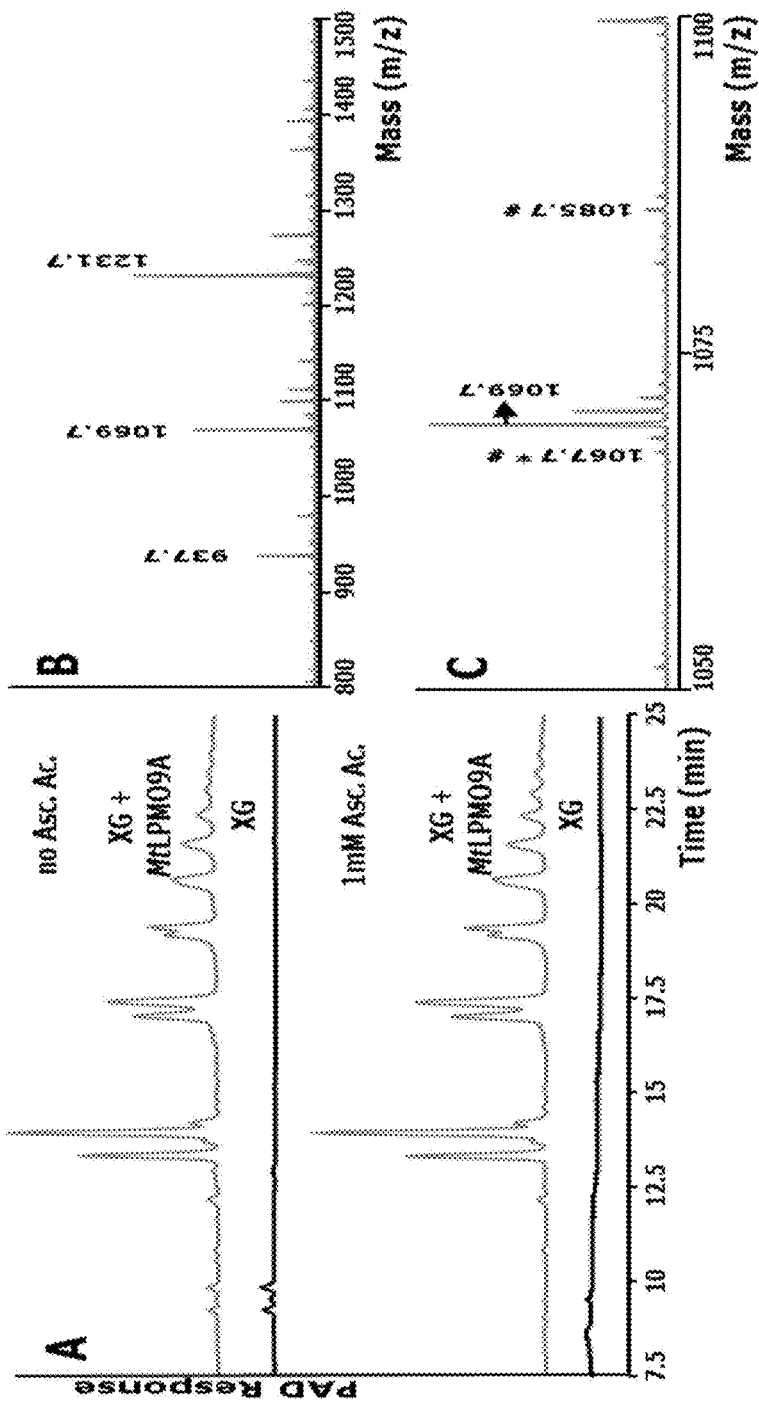
FIG. 11: A—HPAEC elution pattern of xyloglucan from tamarind seed (2 mg/mL) after incubation with partially purified MtLPMO9A (12.5 mg/g substrate). Samples were incubated in 50 mM ammonium acetate buffer (pH 5.0) for 24 h at 52° C., either with ascorbic acid addition (1 mM) or without. Numerous substituted non-oxidized β-D-glycosyl residues of xyloglucan-derived oligomers are formed if xyloglucan is incubated with MtLPMO9A, either with ascorbic acid addition (1 mM) or without. Masses were further analysed by MALDI-TOF MS. B—MALDI-TOF mass spectrum of xyloglucan incubated with MtLPMO9A with 1 mM ascorbic acid addition. At least one un-substituted glucose molecule is needed for hydrolytic cleavage of the glucan backbone. In the presence of ascorbic acid, oxidized products are formed by MtLPMO9A. Clusters of oxidized xyloglucan-oligomers are determined as their lithium (Li) adducts (C—enlargement of B). The insert shows the presence of xyloglucan-oligomers oxidized at C1 with an aldonic acid (#) and at C4 with a keto-group (*). Masses represent lithium-adducts only.
Figure 12:
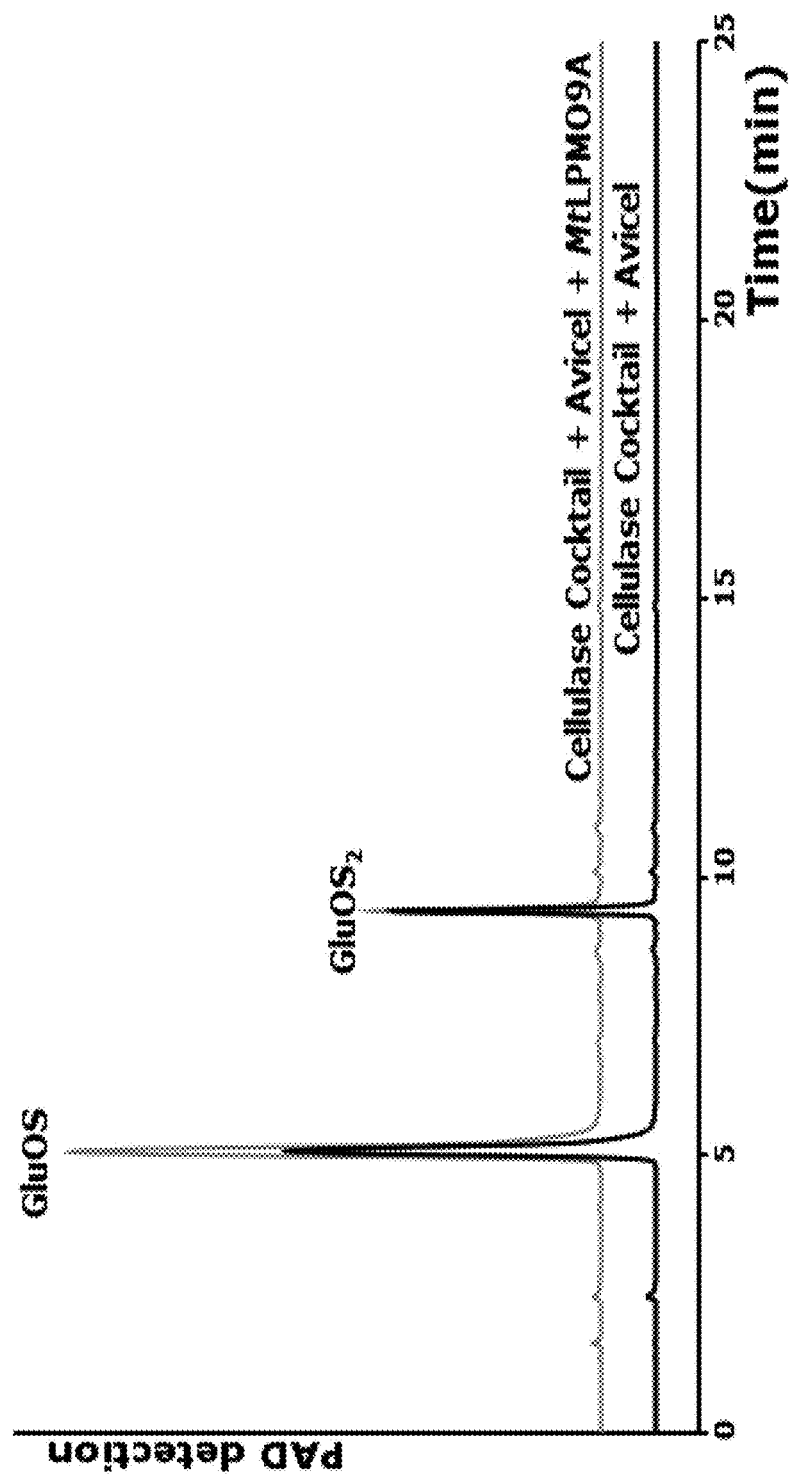
FIG. 12: HPAEC elution patterns of incubations of Avicel with an cellulase enzyme cocktail with and without partially purified MtLPMO9A addition. The addition of MtLPMO9A to a cellulase cocktail results in a 60% higher release of gluco-oligomers (based on HPAEC-area). Samples were incubated in 50 mM acetate buffer (pH 5.0) at 52° C. with ascorbic acid addition (1 mM). The concentration was 5 mg protein/g Avicel for the cellulase cocktail and 2.5 mg/g Avicel for the cellulose cocktail with MtLPMO9A.

Recently, NcLPMO9D from N. crassa expressed in P. pastoris was described to have an activity on hemicellulosic β-(1→4)-linked glucans (13). We found that MtLPMO9A showed a similar mode-of-action on hemicellulosic xyloglucans and β-glucans (FIGS. 10-11). However, formation of oxidized XOS so far has only been observed for MtLPMO9A. Analysis of the protein mass of MtLPMO9A indicated methylation of the N-terminal histidine, whereas the His1 is non-methylated in NcLPMO9D. The role of the post-translational modification of His1 is not clear, but it can be hypothesised that the introduced methyl group has a role in the redox reaction catalysed by LPMOs (18), or alters the flexibility of His1.

Recently, LPMOs of the AA9 class were further divided into subgroups PMOI, PMOII and PMOIII based on their amino acids in the substrate binding site (18). MtLPMO9A shows most similarity with subgroup PMOI and has the highest amino acid sequence identity with TtPMOI (75%). Like TtPMOI, MtLPMO9A considerably enhances glucose release from cellulose (60%) when added to a cellulase-cocktail (17). Additionally, MtLPMO9A shows a strong synergistic effect with TvEG I on amorphous cellulose as shown in the present study. During enzyme purification, the oxidative activity of MtLPMO9A was separated from a strong hydrolytic activity towards cellulose. Probably, MtLPMO9A and the enzyme responsible for this hydrolytic activity are closely working together in vivo. It has already been shown that fungi can express a variety of hydrolases as well as oxidases when grown on lignocellulosic biomass. Therefore, it is likely that more oxidases will have a synergistic effect with hydrolases to enhance the degradation of biomass. Possibly, during the evolution of fungi, the development of enzymes containing both oxidative activities and synergism with hydrolases enabled a more efficient and wider degradation of substrates present in nature.

SI Materials and Methods

Figure 6:
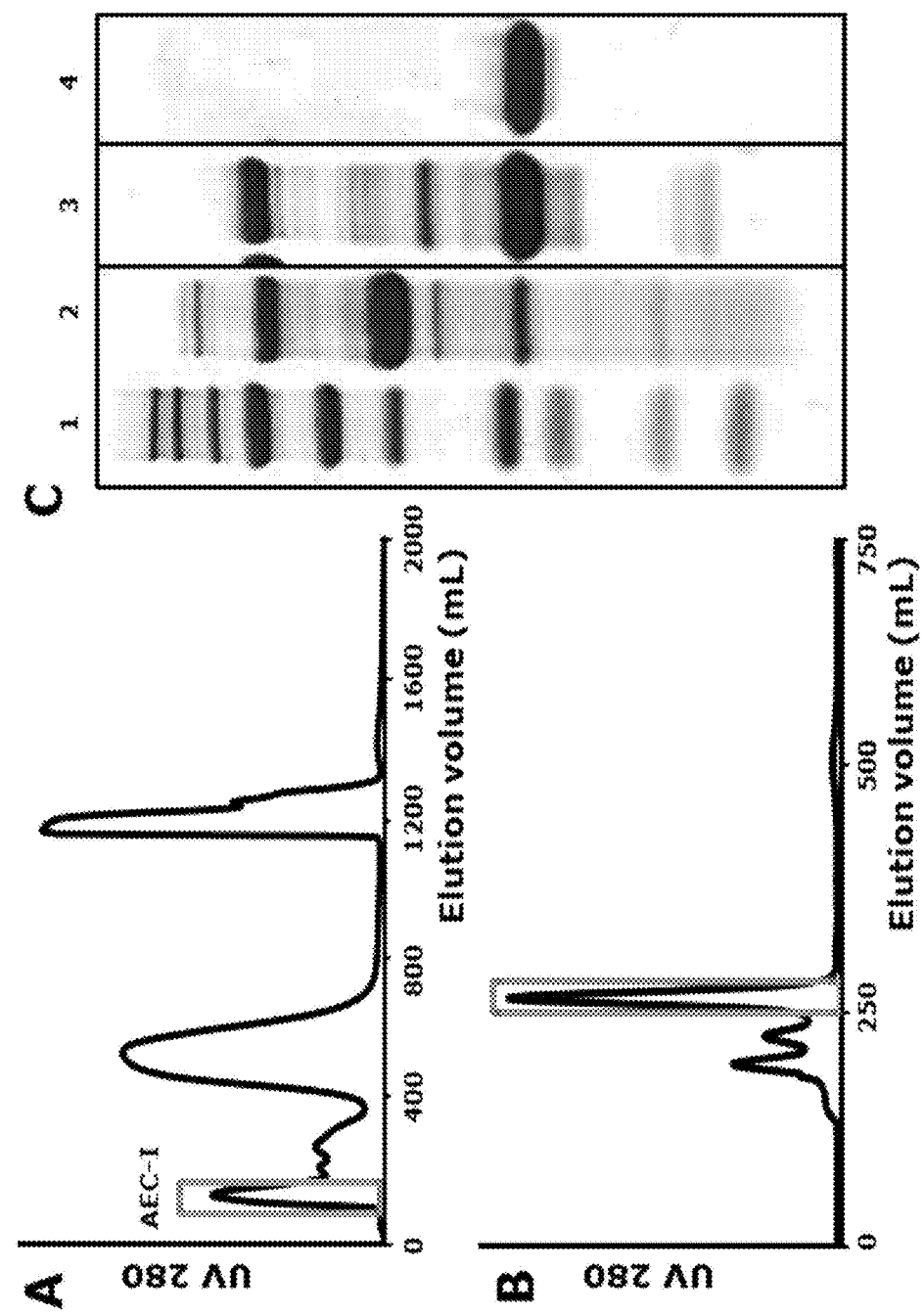
FIG. 6: Purification of LPMO9A from *Myceliophthora thermophila* C1. A—AEC elution profile (step 1) of crude enzyme extract containing expressed MtLPMO9A. B—SEC elution profile of Pool AEC-I (step 2). The red columns indicate the MtLPMO9A-containing fractions pooled and concentrated for further analysis. C—SDS-PAGE of the crude enzyme extract (lane2), Pool AEC-9A (lane 3) and (partially) pure MtLPMO9A (lane 4). Protein bands of MtLPMO9A are indicated by an arrow. For more details about protein purification see Materials and Methods. Lane 1, marker (Precision Plus Protein™, Bio-Rad).

Enzyme production and purification. MtLPMO9A from Myceliophtora thermophila C1 (SEQ ID NO: 1 represents MtLPMO9A without signal sequence; SEQ ID NO: 2 represents MtLPMO9A with signal sequence) was over-expressed in a specially designed C1-expression host (LC strain) (27). The C1-strain was grown aerobically in 2-L fermentors using a medium containing glucose and ammonium sulphate, and enriched with essential salts (28). Next, the enzyme production was performed under glucose limitation in a fed-batch process (pH=6.0; 32° C.). Growth was performed as described previously (28) and delivered a MtLPMO9A-rich crude enzyme extract. The crude enzyme extract was dialysed against 10 mM potassium phosphate buffer (pH 7.0). MtLPMO9A was purified using an AKTA-Explorer preparative chromatography system (GE Healthcare, Uppsala, Sweden). As first step, 3 g of the dialysed crude enzyme mixture (50 mg mL$^{-1}$) was subjected to a self-packed Source 15Q column (100 mm×70 mm internal diameter, GE Healthcare), pre-equilibrated in 10 mM potassium phosphate buffer (pH 7.0). After protein application, the column was washed with 3 volumes of starting buffer. Elution was performed with a linear gradient of 0-1M NaCl in 20 mM potassium phosphate buffer (pH 7.0) over five column volumes. Elution was monitored at 220 and 280 nm. Fractions of 20 mL were collected and immediately stored on ice. Peak fractions were pooled and concentrated using ultrafiltration (Amicon® Ultra, molecular mass cut-off of 3 kDa, Merck Millipore LTD, Cork, Ireland.) at 4° C. The concentrated pools were subjected to SDS-PAGE (FIG. 6). For further purification (2$^{nd}$ step), the MtLPMO9A-containing pool was loaded on a self-packed Superdex™-75 column (100 cm×30 mm internal diameter, GE Healthcare and eluted with a 10 mM potassium phosphate buffer (pH 7.0), containing 150 mM NaCl. Fractions of 5 mL were immediately stored on ice. Pooled fractions were concentrated by ultrafiltration as described above.

The MtLPMO9A preparation thus obtained was further subjected (3$^{rd}$ step) to a Resource™ Q column (30 mm×16 mm internal diameter, GE Healthcare), pre-equilibrated in 20 mM potassium phosphate buffer (pH 7.0). After protein application, the column was washed with 10 column volumes of starting buffer. Elution was performed with a linear gradient of 0-1M NaCl in 20 mM potassium phosphate buffer (pH 7.0) over 20 column volumes. Elution was monitored at 220 and 280 nm. Fractions of 3 mL were immediately stored on ice. Pooled fractions were concentrated by ultrafiltration as described above.

Protein content analysis. To analyse protein contents the BCA™ Protein Assay Kit (Thermo Scientific, Rockford, Ill., USA) was used with bovine serum albumin (BSA) as calibration. The relative subunit molecular mass of the proteins was determined by using sodium dodecyl sulphate polyacrylamide gel electrophoresis (SDS-PAGE). Therefore, proteins were reduced with β-mercaptoethanol, heated for 10 min and loaded on 12% polyacrylamide gels (Mini-PROTEAN TGX Gels, Bio-Rad Laboratories, Hempel Hempstead, UK). In addition, a protein marker (Protein All Blue Standards, Bio-Rad Laboratories Ltd.) was loaded for mass calibration. Gels were stained with the EZBlue™ Gel Staining Reagent (Sigma Aldrich, Steinheim, Germany).

LC/ESI-MS. Purified MtLPMO9A (2.5 mg mL$^{-1}$ in 0.1% (v/v) trifluoroacetic acid (TFA) in $H_2O$) was analysed by liquid chromatography/electrospray ionization-mass spectrometry (LC/ESI-MS) using an ACQUITY UPLC® separation system (Waters, Milford, Mass., USA) equipped with a C4-reversed phase column (UPLC® BEH C4 1.7 μm, 2.1×100 mm, Waters) coupled to a PLC LG 500 photodiode array detector (Waters) and to a SYNAPT G2-Si High Definition Mass Spectrometer (Waters). Gradient elution between eluent A ($H_2O$+1% (v/v) acetonitrile+0.1% (v/v) TFA) and eluent B (acetonitrile+0.1% (v/v) TFA) was performed according to the following steps: from 0 to 2 min isocratic 90% A, from 2 to 12 min gradient from 90% A to 25% A, from 12 to 15 min gradient from 25% A to 100% B, from 12 to 15 min isocratic at 100% B, then re-equilibration to the initial conditions. Flow 0.35 mL/min. Injection volume 2 μL. The photodiode array detector was operated at a sampling rate of 40 points/sec in the range 200-400 nm, resolution 1.2 nm. The SYNAPT mass spectrometer was operated in the positive ion mode (resolution mode), capillary voltage 3 kV, sampling cone 30V, source temperature 150° C., desolvation temperature 500° C., cone gas flow ($N_2$) 200 L/hr, desolvation gas flow ($N_2$) 800 L/hr, acquisition in the full scan mode, scan time 0.3 sec, interscan time 0.015 sec, acquisition range 150-4000 m/z.

RAC preparation. RAC was prepared from Avicel by swelling it in phosphoric acid, which destroyed its original supramolecular structure resulting in a fibrous un-ordered and highly amorphous substrate (29).

Oligomer analysis. Oligosaccharides were analysed by high performance anion-exchange chromatography (HPAEC) with pulsed amperometric detection (PAD). The HPAEC system (ICS-5000, Dionex, Sunnyvale, Calif., USA) was equipped with a combination of a CarboPac PA1 guard column (50 mm×2 mm i.d., Dionex) and a CarboPac PA1 analytical column (250 mm×2 mm i.d., Dionex). The flow rate was 0.3 mL/min (20° C.). Samples were kept at 6° C. in the autosampler and the injection volume was 10 μL. Elution was performed by using two mobile phases: 0.1M NaOH and 1M NaOH in 1M NaOAc. The gradient elution program was as follows: 0-30 min, linear gradient 0-400 mM NaOAc; 30-40 min linear gradient 400-1000 mM NaOAc; followed by a cleaning step and equilibration (15 min) of the column with the starting conditions. Soluble GlcOS and XOS (degree of polymerisation 1-5) as well as glucuronic and gluconic acid were used as standards (Sigma-Aldrich).

MALDI-TOF MS. For matrix-assisted laser desorption ionization—time of flight mass spectrometry (MALDI-TOF MS), an Ultraflex workstation using flexControl 3.3 (Bruker Daltonics) equipped with a nitrogen laser of 337 nm was used. The pulsed ion extraction was set on 80 ns. Ions were accelerated to a kinetic energy of 25 kV and detected in positive reflector mode with a set reflector voltage of 26 kV. The lowest laser energy required was used to obtain a good signal-to-noise ratio. A total of 200 spectra were collected for each measurement. The mass spectrometer was calibrated by using a mixture of maltodextrins in a mass range (m/z) of 500-2500. The peak spectra were processed by using FlexAnalysis software version 3.3 (Bruker Daltonics). Prior to analysis, samples were desalted by adding AG® 50W-X8 Resin (Bio-Rad Laboratories). To obtain lithium (Li)-adducts, the supernatant was dried under nitrogen and re-suspended in 20 mM LiCl (16). Each lithium enriched sample of a volume of 1 μL was mixed with 1 μL of matrix solution (12 mg/mL 2,5-dihydroxy-benzoic acid (Bruker Daltonics) in 30% (v/v) acetonitrile in $H_2O$), applied on a MTP 384 massive target plate (Bruker Daltonics) and dried under a stream of warm air.

TABLE 1

MtLPMO9A oxidation on various polysaccharide substrates

| | | Oxidation | | | |
| | | no ascorbic acid | | 1 mM ascorbic acid | |
| Substrate[1] | Solubility[2] | GlcOS | XOS[3] | GlcOS | XOS[3] |
| --- | --- | --- | --- | --- | --- |
| Cellulose | | | | | |
| Cellulose | − | − | − | + | + |
| RAC | − | − | − | + | + |
| Hemicellulose[4] | | | | | |
| Glucan | | | | | |
| Xyloglucan[5] | +/− | − | − | + | − |
| β-glucan barley | + | − | − | + | − |
| β-glucan oat spelt | + | − | − | + | − |
| Xylan | | | | | |
| OSX | +/− | − | − | − | − |
| BiWX | +/− | − | − | − | − |
| WAX | + | − | − | − | − |
| Oligosaccharides | | | | | |
| Gluco-oligomers[6] | + | − | − | − | − |
| Xylooligomers[6] | + | − | − | − | − |
| Galactomannan Guar[7] | + | − | − | − | − |
| RAC + Hemicellulose | | | | | |
| RAC + BiWX | +/− | − | − | + | + |
| RAC + OSX | +/− | − | − | + | + |
| RAC + WAX | +/− | − | − | − | − |

[1]RAC, OSX, BiWX, WAX
[2]Substrate-solubility in $H_2O$: completely soluble (+), partly soluble (+/−), unsoluble (−)
[3]Gluco-oligomers [GlcOS], xylooligomers [XOS]
[4]Hemicellulose separated into β-(1-4)-linked glucan and xylan
[5]Xyloglucan from tamarind seed
[6]Degree of polymerisation 2-5
[7]β-(1-4)-linked-D-mannosyl backbone

The invention claimed is:

1. A method for degrading xylan in a xylan-comprising substrate, wherein said method comprises:
   (a) contacting the xylan-comprising substrate with a stabilized liquid, paste, or solid formulation comprising a lytic polysaccharide monooxygenase (LPMO) that comprises an amino acid sequence that is at least 90% identical to SEQ ID NO:1 and has xylan-oxidizing activity, wherein said xylan-comprising substrate further comprises, or is further contacted with, an electron donor and cellulose, whereby xylo-oligomers and/or oxidized xylo-oligomers are produced; and
   (b) isolating the xylo-oligomers and/or oxidized xylo-oligomers.

2. The method of claim 1, wherein the LPMO comprises an amino acid sequence that is at least 95% identical to SEQ ID NO:1.

3. The method of claim 1, wherein said LPMO comprises the amino acid sequence of SEQ ID NO:1.

4. The method of claim 1, wherein said method further comprises glucan degradation and/or modification.

5. The method of claim 1, wherein the stabilized liquid, paste, or solid formulation further comprises one or more additional enzymes.

6. The method of claim 1, wherein said method comprises degradation and/or modification of cellulose and/or cellulose associated with hemicellulose.

7. The method of claim 5, wherein the one or more additional enzymes comprise a complex of cellulases and/or hemicellulases obtained from *Trichoderma*.

8. The method of claim 5, wherein the one or more additional enzymes comprise an endoglucanase.

9. The method of claim 8, wherein the endoglucanase comprises an amino acid sequence that is at least 90% identical to SEQ ID NO:3.

10. The method of claim 1, wherein oxidized xylo-oligomers are produced in step (a) and isolated in step (b).

11. The method of claim 2, wherein oxidized xylo-oligomers are produced in step (a) and isolated in step (b).

12. The method of claim 1, wherein xylo-oligomers are produced in step (a) and isolated in step (b).

13. The method of claim 2, wherein xylo-oligomers are produced in step (a) and isolated in step (b).

* * * * *